US012053685B2

(12) United States Patent
Lockhart et al.

(10) Patent No.: US 12,053,685 B2
(45) Date of Patent: Aug. 6, 2024

(54) SYSTEMS AND METHODS FOR PHYSICAL THERAPY

(71) Applicant: PENUMBRA, INC., Alameda, CA (US)

(72) Inventors: Arthur John Lockhart, San Ramon, CA (US); Seppo Helava, Oakland, CA (US); Gaurav Mathur, Alameda, CA (US); David Hill, Alameda, CA (US); Albert Hing-Yin Chen, Alameda, CA (US); Joseph White, Alameda, CA (US)

(73) Assignee: Penumbra, Inc., Alameda, CA (US)

(*) Notice: Subject to any disclaimer, the term of this patent is extended or adjusted under 35 U.S.C. 154(b) by 708 days.

(21) Appl. No.: 17/262,063

(22) PCT Filed: Jul. 22, 2019

(86) PCT No.: PCT/US2019/042884
§ 371 (c)(1),
(2) Date: Jan. 21, 2021

(87) PCT Pub. No.: WO2020/023421
PCT Pub. Date: Jan. 30, 2020

(65) Prior Publication Data
US 2021/0322853 A1    Oct. 21, 2021

Related U.S. Application Data

(60) Provisional application No. 62/702,279, filed on Jul. 23, 2018.

(51) Int. Cl.
*A63B 71/06*    (2006.01)
*A63B 24/00*    (2006.01)
(Continued)

(52) U.S. Cl.
CPC ...... *A63B 71/0622* (2013.01); *A63B 24/0059* (2013.01); *A63B 24/0062* (2013.01);
(Continued)

(58) Field of Classification Search
None
See application file for complete search history.

(56) References Cited

U.S. PATENT DOCUMENTS 6,425,764 B1    7/2002 Lamson
10,130,311 B1    11/2018 De Sapio et al.
(Continued)

OTHER PUBLICATIONS

SR and Written Opinion in PCT/US19/42884 dated Dec. 6, 2019.
(Continued)

*Primary Examiner* — Malina D. Blaise
*Assistant Examiner* — Andrew Bodendorf
(74) *Attorney, Agent, or Firm* — Haley Guiliano LLP

(57) ABSTRACT

A system and method for facilitating physical therapy that may include a wearable display, wearable sensors disposed at varying positions on a user, a processor comprising executable instructions configured to provide a virtual reality environment, virtual characters, and therapeutic activities on the wearable display, wherein the virtual characters interact with the user to provide at least form feedback and positive reinforcement. A new instance of the virtual reality environment, with identifiable differences, may be generated in response to a measured completion or partial completion of a therapeutic activity. Changes in the virtual reality environment may offer users continued indications of progression throughout the duration of a physical therapy program. The system may include a connectable device comprising a display that duplicates a portion of the wearable displays image, enables interaction within the virtual
(Continued)

reality environment, and allows for the selection and modification of therapeutic activities.

36 Claims, 36 Drawing Sheets

(51) Int. Cl.
*G06F 3/01* (2006.01)
*G16H 20/30* (2018.01)
(52) U.S. Cl.
CPC .............. *G06F 3/013* (2013.01); *G16H 20/30* (2018.01); *A63B 2024/0096* (2013.01); *A63B 2220/803* (2013.01); *A63B 2220/836* (2013.01); *A63B 2230/62* (2013.01)

(56) References Cited

U.S. PATENT DOCUMENTS

| | | | | |
|---|---|---|---|---|
| 10,204,525 | B1* | 2/2019 | Tillis | G09B 5/02 |
| 10,839,706 | B2* | 11/2020 | Tanaka | G06F 3/017 |
| 11,179,065 | B2* | 11/2021 | Slepian | A61B 5/6847 |
| 11,857,335 | B1* | 1/2024 | Tadi | A63F 13/213 |
| 2008/0191864 | A1 | 8/2008 | Wolfson | |
| 2012/0101346 | A1* | 4/2012 | Scott | G16H 40/60 600/300 |
| 2012/0245492 | A1* | 9/2012 | Lee | A61B 5/1114 600/595 |
| 2012/0315986 | A1* | 12/2012 | Walling | A63F 13/332 463/31 |
| 2013/0278631 | A1 | 10/2013 | Border et al. | |
| 2013/0317634 | A1* | 11/2013 | French | A63B 24/0087 700/91 |
| 2014/0114119 | A1* | 4/2014 | Wiest | A61M 21/02 600/27 |
| 2014/0121018 | A1* | 5/2014 | Burdea | A63F 13/211 463/36 |
| 2014/0188009 | A1* | 7/2014 | Lange | A61B 5/1127 600/595 |
| 2014/0287389 | A1* | 9/2014 | Kallmann | G16H 20/30 434/247 |
| 2014/0347392 | A1* | 11/2014 | Odessky | A61B 5/1121 345/633 |
| 2015/0079560 | A1 | 3/2015 | Cowan | |
| 2015/0133820 | A1* | 5/2015 | Zohar | G16H 20/30 600/595 |
| 2016/0038075 | A1* | 2/2016 | Burdea | A63F 13/24 434/258 |
| 2017/0025026 | A1* | 1/2017 | Ortiz Catalan | G06F 3/017 |
| 2017/0038829 | A1* | 2/2017 | Lanier | G06T 19/006 |
| 2017/0084189 | A1* | 3/2017 | Rubalcaba | G09B 7/04 |
| 2017/0148339 | A1 | 5/2017 | Van Curen et al. | |
| 2017/0258370 | A1* | 9/2017 | Plotnik-Peleg | A61B 5/744 |
| 2017/0326333 | A1* | 11/2017 | Giap | A61B 6/037 |
| 2017/0361217 | A1* | 12/2017 | Burdea | G16H 50/30 |
| 2018/0121728 | A1* | 5/2018 | Wells | A61B 5/1116 |
| 2018/0161626 | A1* | 6/2018 | Fung | G16H 40/63 |
| 2018/0189568 | A1 | 7/2018 | Powderly et al. | |
| 2018/0190376 | A1 | 7/2018 | Hill et al. | |
| 2018/0228430 | A1* | 8/2018 | Perez Marcos | A61B 5/0077 |
| 2018/0304118 | A1* | 10/2018 | French | A63B 24/0006 |
| 2018/0315247 | A1* | 11/2018 | Van Andel | G06F 3/017 |
| 2018/0336973 | A1* | 11/2018 | Tadi | G06T 19/003 |
| 2018/0348863 | A1* | 12/2018 | Aimone | A61B 5/378 |
| 2019/0015033 | A1* | 1/2019 | Sahin | G16H 20/70 |
| 2019/0088152 | A1* | 3/2019 | Adamovich | A61B 5/1128 |
| 2019/0126145 | A1* | 5/2019 | Lowery | G16H 40/67 |
| 2019/0279519 | A1* | 9/2019 | Somareddy | G06F 3/014 |
| 2019/0346915 | A1* | 11/2019 | Somareddy | G06F 3/013 |
| 2020/0016363 | A1* | 1/2020 | Macri | G06F 3/015 |
| 2020/0185097 | A1* | 6/2020 | Orr | G16H 40/67 |
| 2020/0401214 | A1* | 12/2020 | Orr | G06T 11/00 |

OTHER PUBLICATIONS

Aristidou et al., "Real-time marker prediction and CoR estimation in optical motion capture", The Visual Computer ; International Journal of Computer Graphics, 29(1): 7-26 (2012).

Camporesi et al., "VR solutions for improving physical therapy", 2013 IEEE Virtual Reality (VR), IEEE, Mar. 18, 2013.

Knight et al., "Transradial Prosthesis Performance Enhanced With the Use of a Computer Assisted Rehabilitation Environment," Pervasive Technologies Related to Assistive Environments, ACM, pp. 59-62 Jun. 21, 2017.

Lupu et al., "A virtual reality system for post stroke recovery," 2016 20th International Conference on System Theory, Control and Computing (ICSTCC), IEEE, pp. 300-305 (Oct. 13-15, 2016).

Morales-Rodriguez et al. "Design of an emotional and social interaction paradigm for the animation of 3D characters: the case of a therapy for brain injured people (the mirror neuron paradigm)", Virtual Reality, 11(2-3): 175-184 (2006).

* cited by examiner

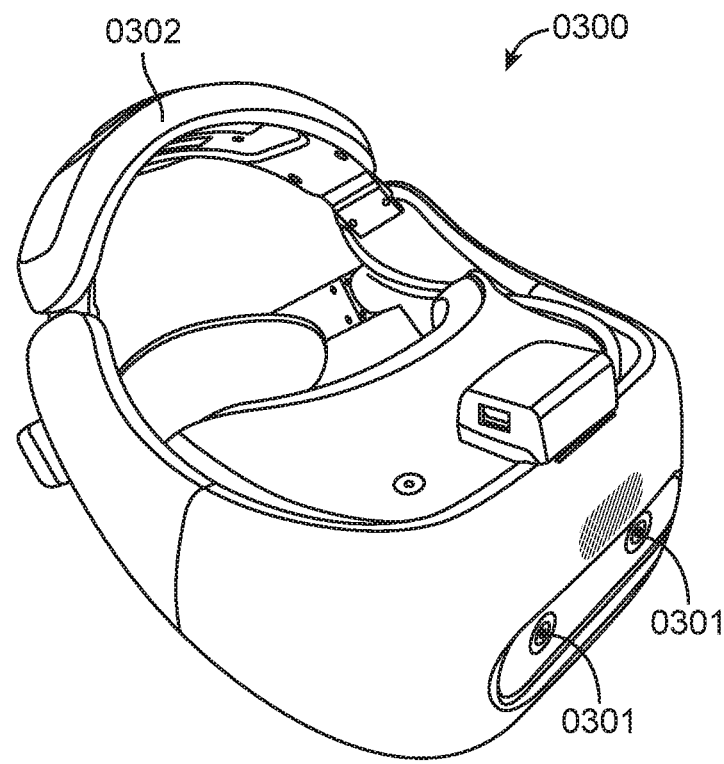
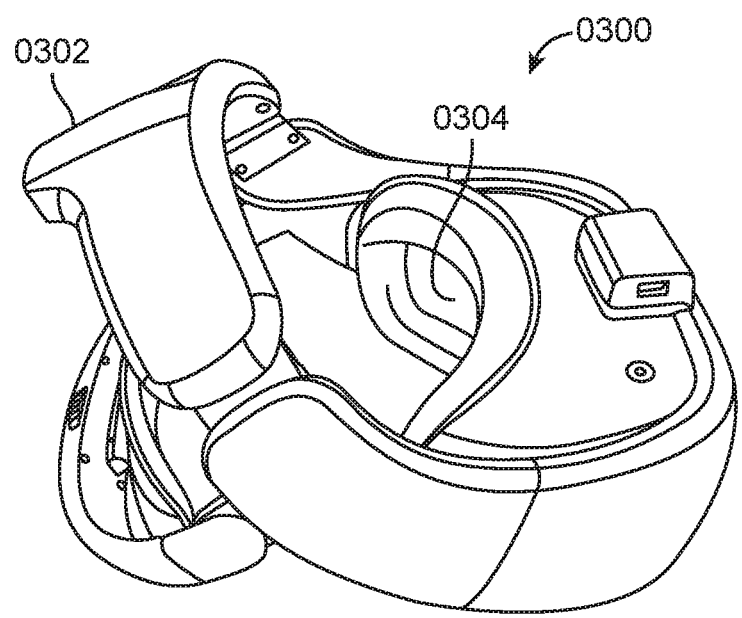
FIG. 3

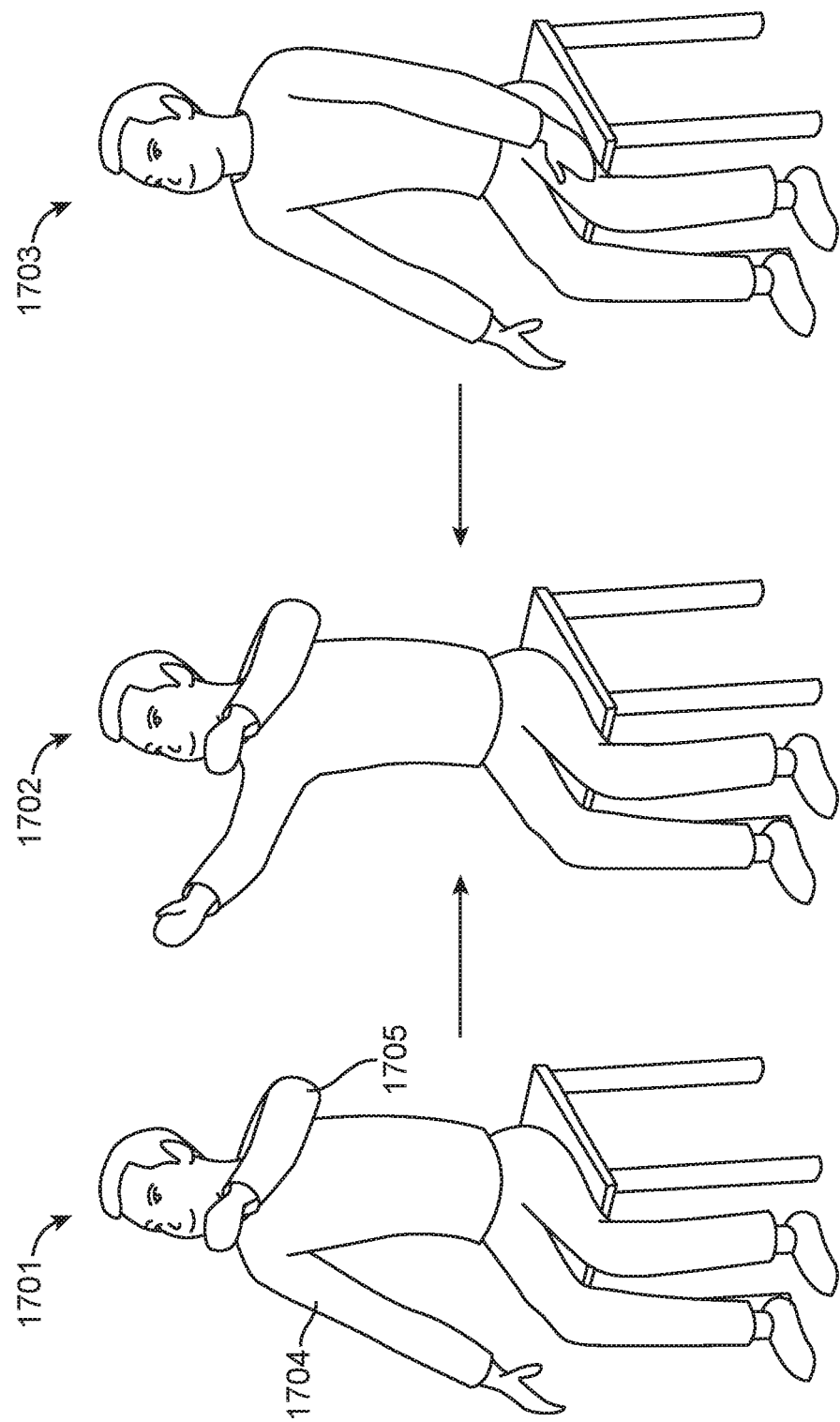

SYSTEMS AND METHODS FOR PHYSICAL THERAPY

CROSS-REFERENCE

This application is a national stage application under 37 U.S.C. § 371 of International Application PCT/US2019/042884, filed Jul. 22, 2019, which claims the benefit of U.S. Provisional Application No. 62/702,279, filed Jul. 23, 2018, which are incorporated herein by reference in their entireties.

BACKGROUND

Stroke is a significant cause of disability and is a growing problem for global healthcare. More than 700,000 people in the United States alone suffer a stroke each year. Of those who survive a stroke, roughly 90% will suffer long term impairment of movement, sensation, memory, or reasoning, ranging from mild to severe. The total cost to the U.S. healthcare system is estimated to be over $50 billion per year, and, adding indirect costs, stroke is estimated to cost the U.S. more than $70 billion per year.

Stroke may be caused from a rupture of a cerebral artery (referred to as a "hemorrhagic stroke"), or by a blockage or occlusion in a cerebral artery resulting from a thromboembolism (referred to as an "ischemic stroke"). Roughly 80% of strokes are classified as ischemic. When a patient experiences an ischemic stroke, the occlusion prevents blood flow to vital brain tissue, thereby depriving the tissue of oxygen, causing nerve cell damage and potentially cell death. After an event the recovery process can be arduous. Conditions and symptoms of cerebral palsy, stroke, orthopedic injury, neurodegenerative disease, acute pain, and similar conditions can also be arduous to recover from. The arduous nature of the recovery can be very discouraging and may prevent victims from following through with recover activities, such as physical therapy. Thus, there is a need to encourage and increase participation in recovery activities. Aspects of the present invention satisfy this need.

SUMMARY

The present application relates to systems and methods of providing therapy which may be beneficial to a patient recovery after an event such as cerebral palsy, stroke, orthopedic injury, neurodegenerative disease, acute pain, and similar conditions. In such cases, it may be necessary to rebuild patient mobility and cognition via the use of physical therapy.

In an aspect, the present disclosure provides a system for facilitating physical therapy. The system may comprise: a wearable visual display; one or a plurality of wearable sensors configured to be disposed at varying positions on a user, wherein a real-world motion of the user is tracked by the one or a plurality of wearable sensors; a processor comprising executable instructions configured to provide: a virtual reality environment on the wearable visual display with one or a plurality of virtual characters; at least one therapeutic activity within the virtual reality environment, wherein the therapeutic activity is directed to produce a therapeutic outcome; and an interaction between the one or plurality of virtual reality characters and the user within the virtual reality environment, wherein the interaction comprises at least one of an indication to change a real-world motion of the user to conform to the therapeutic activity or an indication of successful conformity.

In some embodiments, the interaction is configured to promote performance of a portion of the treatment plan. In some embodiments, the indication comprises a change to a direction or a speed of motion. In some embodiments, the indication comprises an indication to correct posture or balance or both. In some embodiments, the interaction occurs in response to a measured completion of the therapeutic activity by the user. In some embodiments, the interaction occurs in response to a measured non-completion or partial completion of the therapeutic activity by the user. In some embodiments, the one or the plurality of virtual characters mimics or mirrors the motion of the user. In some embodiments, the one or the plurality of virtual characters solicits help from the user in the form of one or more therapeutic activities. In some embodiments, the interaction of the one or the plurality of virtual characters comprises cheering, praising, celebrating, or awarding one or more of the therapeutic activities of the user.

In some embodiments, at least one of the sensors includes an emitter, wherein the emitter and the at least one sensor are configured to track movements of the user. In some embodiments, the processor further comprises instructions to display an avatar that represents the user, wherein the avatar is configured to display at least a portion of a movement of the user in the virtual reality environment. In some embodiments, the processor includes executable instructions for a mid-line mirror protocol that measures a movement of a first side of the user and displays that movement on a first side of the avatar and a mirror of that movement on a second side of the avatar. In some embodiments, the processor includes executable instructions for an anti-gravity protocol that causes arms and hands of the avatar to float upwards as if at least a portion of the avatar was not restrained by gravity. In some embodiments, a displayed motion of the avatar is different from the real-world motion, and a difference between the displayed motion and the real-world motion being varied to induce the user to perform the therapeutic activity.

In some embodiments, the one or more therapeutic activities is selected from the group consisting of: straight arm raises, arm reaches, catching or blocking projectiles, picking up and placing objects, turning and looking, gazing at targets, dodging, cane raise exercises, rotator cuff abductor and adductor exercises, leaning, twisting, core balance exercises, and arm swinging exercises. In some embodiments, the one or more therapeutic activities are presented as a game and are selected from the group consisting of: a hide-n-seek game, requiring the user to turn and look, a sun rise game, requiring the user to raise their arms, a bird sorting game, requiring the user to reach and place, a fish toss game, requiring the user to block and dodge, and a hot air balloon game requiring the user to balance, lean, or bend. In some embodiments, the virtual reality environment changes in response to a measured completion or partial completion of the therapeutic activity. In some embodiments, the virtual characters respond to completed therapeutic activities by starting a building project, wherein a completed version of the building project appears when the user logs into the virtual reality environment for a follow-up physical therapy session.

In some embodiments, the one or more therapeutic activities are comprised of one or more repetitions, and wherein at least a portion of the one or more repetitions results in a display of visual cues to the user. In some embodiments, the visual cues include at least one from among: a sun rises or sets, a vegetable grows, a fruit grows, a balloon moves, a bird moves, wind blows, ice melts, water flows, a building is built, or a location becomes cleaner or messier. In some embodiments, the visual cues include indications of whether a most recent of the one or more repetitions was executed correctly by the user, and wherein the one or more repetitions are measured for correct posture, correct balance, or both. In some embodiments, the one or a plurality of wearable sensors are configured to collect range of motion data for each of the one or more repetitions, wherein the display of the visual cues are mediated by a range of motion of the one or more repetitions, and wherein the display of visual cues is complete for a complete repetition and the display of visual cues is partial for a partial repetition. In some embodiments, the range of motion required for the complete repetition is adjustable by the user or a practitioner. In some embodiments, the one or a plurality of wearable sensors are configured to determine a maximum extension achieved for each of the one or more repetitions, wherein the display of the visual cues is mediated by the maximum extension, and wherein the display of the visual cues is complete for a full extension and the display of the visual cues is partial for a partial extension.

In some embodiments, the one or more virtual characters are displayed in danger, wherein the user is able to rescue the one or more virtual characters through the performance of the therapeutic activity, whereby the danger provides motivation to perform the therapeutic activity. In some embodiments, the system includes a tablet computer configured to display at least a portion of a view of the user within the virtual reality environment. In some embodiments, the one or more virtual characters are further configured to interact with the user when the user gazes at the one or more virtual characters or when the user is idle. In some embodiments, the one or more virtual characters further interacts by acknowledging the user, gesturing to the user, approaching the user, or hiding from the user.

In another aspect, a system for facilitating physical therapy is provided. The system may comprise: a wearable visual display; one or a plurality of wearable sensors configured to be disposed at varying positions on a user, wherein a real-world motion of the user is tracked by the one or a plurality of wearable sensors; a processor comprising executable instructions configured to generate a virtual reality environment on the wearable visual display with one or a plurality of virtual characters and provide a therapeutic activity within the virtual reality environment; and a connectable device, wherein the connectable device is configured to provide to a practitioner an indication of a status of the user, and wherein the connectable device is configured to prompt the processor to provide the therapeutic activity.

In some embodiments, the connectable device comprises a display comprising an image, the image on the connectable device comprising at least a portion of an image shown on the wearable visual display. In some embodiments, the connectable device is configured to provide instructions to the processor, the instructions comprising one or more of: providing or changing a therapeutic activity, providing a game, changing a difficulty of the therapeutic activity or the game, and providing an indication of a status of the user with respect to a treatment plan, and providing an indication of a type of quality of the motion of the user. In some embodiments, the connectable device is configured to facilitate an interaction between the practitioner and the user in virtual reality. In some embodiments, the interaction between the practitioner and the user in virtual reality comprises playing a game together. In some embodiments, the game is one or more of playing catch, a fish toss game, requiring the user to block and dodge, hide-n-seek, requiring the user to turn and look, a sun rise game, requiring the user to raise their arms, a bird sorting game, requiring the user to reach and place, and a hot air balloon game requiring the user to balance, lean, or bend.

In some embodiments, the connectable device is a tablet computer. In some embodiments, the connectable device is a second wearable visual display. In some embodiments, the connectable device is configured to control an action of the one or a plurality of virtual characters. In some embodiments, the connectable device is configured to control an interaction between the one or the plurality of virtual reality characters and the user. In some embodiments, the interaction comprises an indication to change the real-world motion of the user to conform to the therapeutic activity. In some embodiments, the interaction comprises a change to a direction or a speed of motion. In some embodiments, the interaction comprises an indication to correct posture or balance or both.

In some embodiments, the one or more therapeutic activities is selected from the group consisting of: straight arm raises, arm reaches, catching or blocking projectiles, picking up and placing objects, turning and looking, gazing at targets, dodging, cane raise exercises, rotator cuff abductor and adductor exercises, leaning, twisting, core balance exercises, and arm swinging exercises. In some embodiments, the virtual reality environment changes in response to a measured completion or partial completion of the therapeutic activity. In some embodiments, the virtual characters respond to a measured completion of one or more therapeutic activities by starting a building project, wherein a completed version of the building project appears when the user logs into the virtual reality environment for a follow-up physical therapy session.

In some embodiments, the one or more therapeutic activities is comprised of one or more repetitions, wherein at least a portion of the one or more repetitions results in a display of visual cues to the user. In some embodiments, the visual cues include at least one from among: a sun rises or sets, a vegetable grows, a fruit grows, a balloon moves, a bird moves, wind blows, ice melts, water flows, a building is built, or a location becomes cleaner or messier. In some embodiments, the visual cues include indications of whether a most recent of the one or more repetitions was executed correctly by the user, wherein the one or more repetitions are measured for correct posture, correct balance, or both. In some embodiments, the one or a plurality of wearable sensors are configured to collect range of motion data for each of the one or more repetitions, wherein the display of the visual cues are mediated by a range of motion of the one or more repetitions, and wherein the display of visual cues is complete for a complete repetition and the display of visual cues is partial for a partial repetition. In some embodiments, the range of motion required for the complete repetition is adjustable by the practitioner on the connectable device. In some embodiments, the one or a plurality of wearable sensors are configured to determine a maximum extension achieved for each of the one or more repetitions, wherein the display of the visual cues is mediated by the maximum extension, wherein the display of the visual cues is complete for a full extension and the display of the visual cues is partial for a partial extension.

In another aspect, a system for facilitating physical therapy is provided. The system may comprise: a wearable visual display; one or a plurality of wearable sensors configured to be disposed at varying positions on a user, wherein a real-world motion of the user is tracked by the one or a plurality of wearable sensors; and a processor comprising executable instructions configured to provide: a first virtual reality environment on the wearable visual display with one or a plurality of virtual characters; a therapeutic activity within the first virtual reality environment, wherein the therapeutic activity comprises a portion of a treatment plan; and a second virtual reality environment generated in response to a measured completion or partial completion of the therapeutic activity.

In some embodiments, the processor is configured to update the treatment plan based on the motion of the user during performance of the therapeutic activity. In some embodiments, the processor is configured to provide a second therapeutic activity within the second virtual reality environment. In some embodiments, the second environment displays a second one or a plurality of virtual characters. In some embodiments, the second environment displays one or a plurality of virtual structures, virtual characters, or virtual items different, or in different locations, from the first environment. In some embodiments, the second environment displays a virtual landscape different from the first environment. In some embodiments, a building project begins in response to the measured completion or partial completion of the therapeutic activity. In some embodiments, the one or a plurality of virtual characters are shown to build one or a plurality of virtual structures. In some embodiments, the wearable visual display provides the second virtual environment during a follow-up session. In some embodiments, the second virtual reality environment is different from the first environment in at least one of the following: a sun rises or sets, a vegetable grows, a fruit grows, a balloon moves, a bird moves, wind blows, ice melts, water flows, a building is built, or a location becomes cleaner or messier.

In some embodiments, the one or more therapeutic activities is selected from the group consisting of: straight arm raises, arm reaches, catching or blocking projectiles, picking up and placing objects, turning and looking, gazing at targets, dodging, cane raise exercises, rotator cuff abductor and adductor exercises, leaning, twisting, core balance exercises, and arm swinging exercises. In some embodiments, the one or more therapeutic activities is presented as a game and is selected from the group consisting of: a hide-n-seek game, requiring the user to turn and look, a sun rise game, requiring the user to raise their arms, a bird sorting game, requiring the user to reach and place, a fish toss game, requiring the user to block and dodge, and a hot air balloon game requiring the user to balance, lean, or bend.

In some embodiments, a degree of difference between the first virtual environment and a second virtual environment reflects a degree of progress by the user along the treatment plan. In some embodiments, the degree of progress relates to at least one of an improvement in form, an improvement in strength, an improvement in range of motion, a frequency of return sessions, or an improvement in cognitive function. In some embodiments, a degree of difference between the first environment and the second environment is configured to be adjustable by a practitioner.

In another aspect, a computer implemented method for facilitating a therapeutic activity of a user is provided. The computer implemented method may comprise: providing a first virtual reality environment comprising one or a plurality of virtual characters on a visual display worn by the user; receiving a real-world motion of a user from one or a plurality of sensors worn by the user; providing the therapeutic activity within the first virtual reality environment, wherein the therapeutic activity comprises a portion of a treatment plan; and adapting the virtual reality environment, wherein the adapting is in response to a measured completion or partial completion of the therapeutic activity.

In some embodiments, the step of adapting comprises displaying a second one or a plurality of virtual characters. In some embodiments, the step of adapting comprises displaying one or a plurality of virtual structures, virtual characters, or virtual items different, or in different locations, from the first environment. In some embodiments, step of adapting comprises displaying a virtual landscape different from the first environment. In some embodiments, the step of adapting comprises beginning a building project in response to the measured completion or partial completion of the therapeutic activity. In some embodiments, the one or a plurality of virtual characters are shown to build one or a plurality of virtual structures. In some embodiments, the method further comprises displaying the adapted virtual environment during a follow-up session. In some embodiments, the adapted virtual reality environment is different from the first environment in at least one of the following: a sun rises or sets, a vegetable grows, a fruit grows, a balloon moves, a bird moves, wind blows, ice melts, water flows, a building is built, or a location becomes cleaner or messier.

In another aspect, a computer implemented method for facilitating a therapeutic activity of a user is provided. The method may comprise: providing a first virtual reality environment comprising one or a plurality of virtual characters on a visual display worn by the user; receiving a real-world motion of a user from one or a plurality of wearable sensors worn by the user; providing the therapeutic activity within the first virtual reality environment, wherein the therapeutic activity comprises a portion of a treatment plan; and directing the one or a plurality of virtual characters provide a user interaction, wherein the user interaction is in response to a measured completion or partial completion of the therapeutic activity, wherein the interaction comprises an indication to change the real-world motion of the user to conform to the therapeutic activity or an indication of successful conformity.

In some embodiments, the interaction is configured to promote performance of a portion of the treatment plan. In some embodiments, the indication comprises a change to a direction or a speed of motion. In some embodiments, the indication comprises an indication to correct posture or balance or both. In some embodiments, the interaction occurs in response to a measured completion of the therapeutic activity by the user. In some embodiments, the interaction occurs in response to a measured non-completion or partial completion of the therapeutic activity by the user. In some embodiments, the one or the plurality of virtual characters mimics or mirrors the motion of the user. In some embodiments, the one or the plurality of virtual characters solicits help from the user in the form of one or more therapeutic activities. In some embodiments, the interaction of the one or the plurality of virtual characters comprises cheering, praising, celebrating, or awarding one or more of the therapeutic activities of the user.

In one aspect, the present disclosure provides a system for providing therapy. The system may comprise a head mounted display; a wearable emitter and/or one or a plurality of wearable sensors for tracking real-world motion; and a processor comprising executable instructions.

The processor's executable instructions may be configured to provide a plurality of images, wherein the images elicit a response from a subject, and the response comprises one or a plurality of therapeutic actions. The processor may further comprise executable instructions configured to generate a virtual reality environment with one or a plurality of virtual characters; at least one therapeutic activity within the virtual reality environment, wherein the therapeutic activity is directed to produce a therapeutic outcome; and an interaction between the one or the plurality of virtual reality characters and the user, wherein an interaction between a user and a virtual character comprises an indication to change the real-world motion of the user to conform to a therapeutic activity or an indication of successful conformity. An interaction with one or the plurality of virtual characters may comprise positive reinforcement, such as cheering, praising, celebrating, or awarding one or more of the therapeutic activities of the user.

The processor may further comprise instructions to display an avatar that represents the user, wherein the avatar is configured to display at least a portion of a movement of the user in the virtual reality environment. In one example, a displayed motion of the avatar is different from the real-world motion, and a difference between the displayed motion and the real-world motion being varied to induce the user to perform the therapeutic activity.

In one example, a second virtual reality environment is generated in response to a measured completion or partial completion of the therapeutic activity, which may be comprised of one or a plurality of virtual structures, virtual characters, or virtual items different, or in different locations, from the first environment. Such a new instance of the virtual reality environment may offer users continued indications of progression throughout the duration of a physical therapy program. In one example, the processor includes instructions for generating a second virtual environment, which may be presented during a follow-up session.

The system may include a connectable device comprising a display that may duplicate a portion of the wearable display's image, enable interaction within the virtual reality environment, and allow for the selection and modification of therapeutic activities. The connectable device may be configured to prompt the processor to provide the therapeutic activity and configured to provide a practitioner with an indication of user status. In one example, the connectable device allows a practitioner to play a game with the user in virtual reality. In one example, the connectable device is a tablet computer.

In another aspect, the present disclosure provides a method of providing therapy. The method may comprise providing to a subject a head mounted display and one or a plurality of wearable sensors; displaying an image to the subject, wherein the image elicits a subject response comprising a therapeutic action; recording the subject response to the image, the response comprising at least one of a position or a motion of at least one of the plurality of sensors; and displaying a second image to the subject, wherein the second image comprises a difference between a prescribed outcome of the therapeutic action and the recorded response or the image indicates successful adherence to the prescribed outcome. The method may further include presenting therapeutic exercises as virtual reality games.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 illustrates a head mounted display ("HMD"), in accordance with some embodiments.

FIG. 17 illustrates an avatar rendered to not match the position of the player, in accordance with some embodiments.

DETAILED DESCRIPTION

Figure 1:
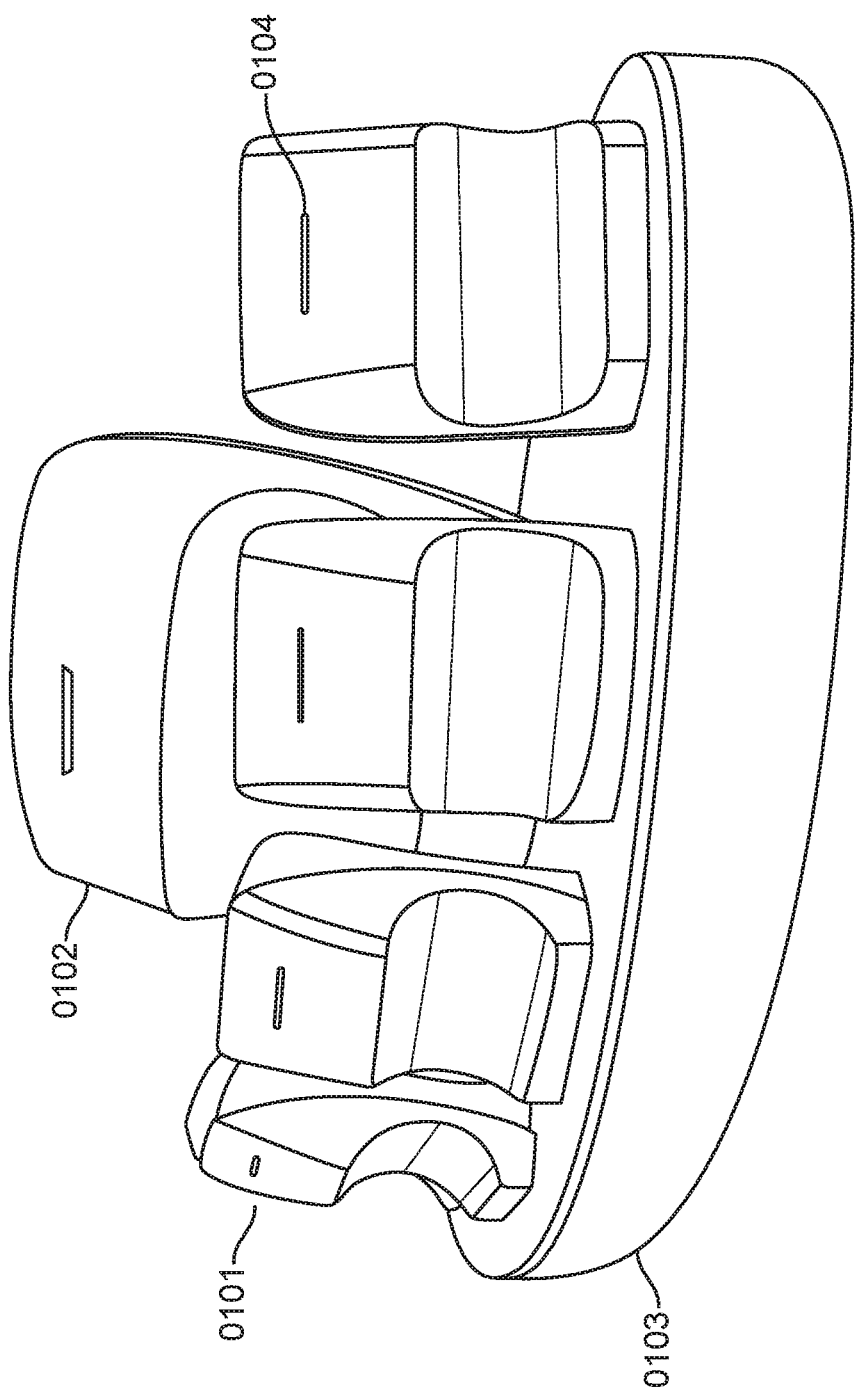
FIG. 1 illustrates sensors for tracking movements and their charging station, in accordance with some embodiments.

In one embodiment, the presentation invention is a virtual reality (VR) game for stroke victim exercise mobility therapy. Therapy exercises may be tracked by up to eleven electromagnetic sensors that track the movement of the player's limbs, torso, and head. The exercises are typically presented as activities and games within a virtual reality environment. The activities and games are set within the Happy Valley, which is a virtual reality environment that evolves and transforms as the player progresses through the games. The player's view in VR may be at least partially duplicated on a tablet computer, for use by an attending physical therapist (PT), occupational therapist (OT), or practitioner. The tablet may provide the practitioner with an interface for controlling the game.

The exercises provide the player with both short-term and long-term feedback. Short-term feedback may be provided during each repetition ("rep") of a therapeutic exercise, after a therapeutic exercise is completed, after a portion of a therapeutic exercise is completed, or some combination thereof. Short-term feedback may include visual indications of rep quality and for rep completion, such as a scoreboard that keeps count of the reps, virtual characters that mimic or mirror the player's movements, animations of the virtual characters that cheer, sing, play music, and/or otherwise motivate the player to continue, physical changes in the virtual reality environment, such as the sun rising, food growing, ice melting, wind blowing, or construction projects—initiated by villagers the player helps—in the virtual reality environment. Small changes to the virtual reality environment may build up over time providing indications of long-term feedback. Other forms of long-term feedback may include a stamp card that keeps track of the number of completed exercises or unlocking new areas in the virtual reality environment that can also be built up. A player may be offered a birds-eye view of the Happy Valley to show the progress that player has caused by performing activities there. Building the village is analogous to the player rebuilding themselves. The novel virtual reality environment of the Happy Valley provides an immersive environment that encourages participation, elicits excitement, and may increase exercise effort. The system may include a cell phone app with a village viewer, text alerts for exercise schedule notifications, progress reports, and goal reaching encouragement.

In one embodiment, a player may obtain items, currency, decorations, or achievements for completing therapeutic exercises. The rewards a player has obtained and the state of the player's version of the Happy Valley may viewable within a downloadable app and optionally shareable on social media. Such rewards and feedback are all designed to encourage participation. This type of encouragement is especially valuable in the most critical stage of stroke therapy, early therapy, because progress is often slow and imperceptible to the patient.

Project Hardware
Computing Environment

In the present invention, a computing environment comprises one or more printed circuit boards (PCBs). The computing environment may function as a single device or across several devices. In general terms, the computing environment tracks, models, and displays a visual representation of a user in physical space. The computing environment tracks a user's surroundings and movements in physical space, generates a 3-D model of the user in virtual space, and displays a visual representation of the model for the user. For instance, the visual representation may be an avatar displayed on a screen, where the avatar's motion is controlled by the user by mapping a user's motion in physical space to the avatar's motion in virtual space.

The one or more PCBs include software and hardware components that enable the computing environment to execute applications that allow a user and/or the computing environment to play games and various types of media and allow the user and/or computing environment to control and manipulate non-game applications and operating systems. The printed circuit board may include one or more sensors, processors, graphic processing units (GPU), video encoder/video codec, sound cards, transmitter modules, network interfaces, and light emitting diodes (LED). These components may be housed on a PCB or be in wired or wireless connection. Connections between components may be facilitated by one or more buses (e.g. peripheral component interconnects (PCI) bus, PCI-Express bus, or universal serial bus (USB). With such buses, the computing environment is capable of integrating numerous components and numerous PCBs. One or more system management controllers may provide data transmission management functions between the buses and the components they integrate. Such management controllers facilitate the computing environment's orchestration of these components that each require specific instructions within specific time frames to properly execute desired applications. The network interface may include an Ethernet connection or a component that forms a wireless 802.11b, g, a, or n connection to a local area network (LAN), wide area network (WAN), intranet, or internet.

Sensor(s)

The present invention optionally uses electromagnetic tracking, optical tracking, infrared tracking, accelerometers, magnetometers, gyroscopes, myoelectric tracking, other tracking techniques known in the art, or a combination of one or more of such tracking methods. Electromagnetic sensors may be comprised of EM receivers, EM emitters, or both. The tracking systems exist on the one or more PCBs where they monitor one or more users to capture, analyze, and track their movements. The system preferably utilizes more than one tracking method to improve reliability, accuracy, and precision.

Figure 2A:
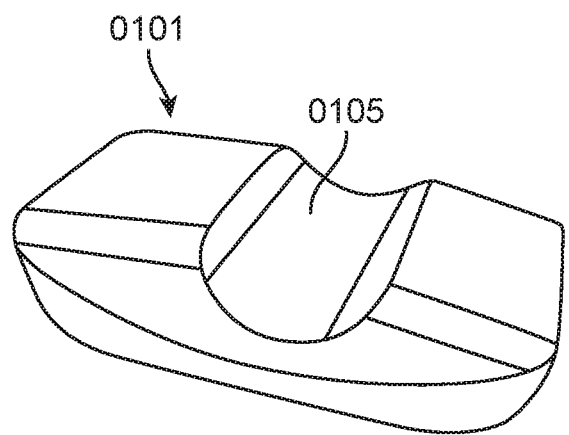
FIGS. 2A-2C illustrate an individual sensor and its attachment means, in accordance with some embodiments.
Figure 2B:
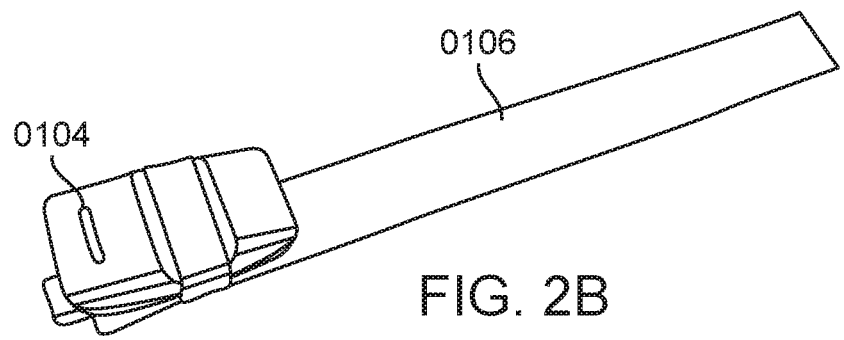
Figure 2C:
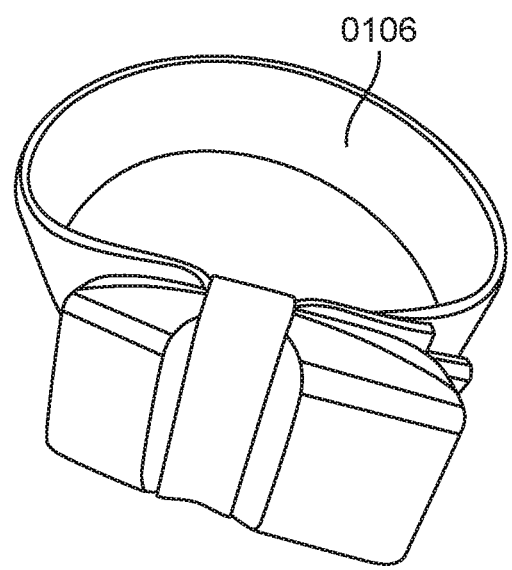

FIG. 1 illustrates an example of wearable electromagnetic sensors 0101, 0102 and their charging station 0103. In this example, the wearable sensor 0101 includes an EM receiver and the wearable sensor 0102 includes an EM receiver and an EM emitter. The wearable sensors may include a light 0104 indicating charge status, such as blue or green for charged or charging and red for charge needed. The wearable sensors may be wireless, small, and nonintrusive as illustrated in FIGS. 2A-2C. To attach the sensors, the sensors may include a recess 0105 that accommodates a cloth and Velcro strap 0106 that can be used to attach the wearable sensors to a user. This attachment method beneficially does not require the player to hold anything and leaves the hands of the player free during performance of therapeutic exercises. Therapeutic exercises are performed more easily when a user does not have to hold a controller and the user is not attached by wiring.

Electromagnetic, IMU, Optical, and Myoelectric Tracking

In general, electromagnetic tracking may be enabled by running alternating current through one or more ferrite cores with three orthogonal (x, y, z) coils, thereby transmitting three dipole fields at three orthogonal frequencies. The alternating current generates a dipole, continuous wave electromagnetic field. With multiple ferrite cores, differentiation between cores may be achieved using frequency division multiplexing. U.S. Pat. No. 8,520,010 & 10,162, 177 provide additional details. In short, the cores function to emit and/or receive EM signals from each other, ferrous objects around the user, and/or the earth's magnetic field to determine the position and orientation of the core and thus the sensor.

Tracking may be enhanced by inertial measurement units (IMUs). IMUs may include accelerometers, magnetometers, and gyroscopes. Accelerometers measure the rate of change of the velocity of a given PCB undergoing movement in physical space. Magnetometers characterize magnetic field vectors by strength and direction at a given location and orientation. Gyroscopes utilize conservation of angular momentum to determine any rotations of a given PCB. The individual components of an IMU serve to supplement, verify, and improve the tracking data captured by electromagnetic sensors. In one example, the wearable sensors 0101, 0102 utilize a combination of electromagnetic tracking and IMU tracking to capture, analyze, and track a user's movements.

Optical tracking and infrared tracking may be achieved with one more capture devices employing an RGB camera, time-of-flight analysis, structured light analysis, stereo image analysis, or similar techniques. In one example of time-of-flight, the capture device emits infrared (IR) light and detects scattered and reflected IR light. By using pulsed IR light, the time-of-flight between emission and capture for each individual photon indicates the distance the photon traveled and hence the physical distance of the object being imaged. This allows the camera to analyze the depth of an image to help identify objects and their locations in the environment. Similar techniques analyze reflected light for phase shifts, intensity, and light pattern distortion (such as bit maps). Stereo image analysis utilizes two or more cameras separated by some distance to view a similar area in space. Such stereo cameras capture any given object at one or more angles, which enables an analysis of the object's depth. Optical tracking may also identify an object or location in physical space to serve as an anchor, e.g. (0, 0, 0). The tracking system then determines global movements in reference to the anchor. Such an anchor is particularly useful for use in conjunction with electromagnetic tracking, which is typically self-referential and does not necessarily track movements in global coordinates. FIG. 3 illustrates examples of a head mounted display (HMD) of the present invention that includes two cameras 0301.

Myoelectric tracking may be achieved using multiple sensors capable of sensing nerve impulse (EMG) signals. The sensors may be attached with a band, with leads, or with a needle electrode. The EMG signals being decoded into a model of intended movements by a learned algorithm executed, at least, in part by a processor as discussed below. Monitoring EMG activity can be useful for measuring the neural activity associated with neuroplasticity.

In one specific example, the electromagnetic sensors each include a receiver (RX) module having three orthogonal coils that are configured to receive an electromagnetic field generated by a transmitter (TX), which also includes three orthogonal coils. The magnetic field data collected at each coil is processed by a Discrete Fourier Transformation (DFT). With three coils on each module, the signal received by a module is representable by a 3×3 signal matrix ("Sigmat"), which is a function of a transmitter-to-sensor radius vector and a transmitter-to-sensor rotation matrix (a.k.a. directional cosines or projection matrix). An IMU and camera system may be used to correct for errors in electromagnetic tracking. In one example, a dipole field approximation allows for the determination of position and orientation (PnO) according to Equation 1, as described in U.S. Pat. No. 4,737,794.

$$X = N^t B(r) \qquad \text{Equation 1:}$$

X—3×3 Sigmat Matrix (as sensed in RX coordinates)

N—3×3 orthonormal orientation (in TX coordinates) Transmitter to sensor rotation matrix (6 values received from IMUs)

r—3×1 position vector (in TX coordinates) (transmitter to sensor radius vector)

B—3 magnetic fields at r as the columns of a 3×3 matrix (in TX coordinates)

Distortion and interference may be compensated for by adding E(r) to the equation. E(r) is a result calculated from the super position of the theoretic dipole fields and is represented as a 3×3 matrix of unknown magnetic field distortion or interference. E(r) may be described as an error matrix in that is compensates for errors in calculated PnO, as described in U.S. Pat. No. 9,459,124.

$$X = N^t(B(r) + E(r)) \qquad \text{Equation 2:}$$

E(r) may be calculated using data from IMUs and a camera system (as explained in more detail below). Each IMU typically includes an accelerometer, a gyroscope, and a magnetometer. These components help correct for error, noise, and phase ambiguity in PnO calculations, as described in U.S. Pat. No. 10,234,306. For example, assume Sigmat is being distorted by a nearly uniform EM field generated by a large wire loop on the floor. To model distortion, the direction of the distortion field (v) and the gains per frequency (P) must be determined.

$$E(r) = v \cdot P \qquad \text{The Distortion field:}$$

v—3×1 direction of the distortion field (same for all three frequencies)

P—1×3 gains for the distortion field per frequency (scalar)

$$X = N^t(B(r) + v \cdot P) \qquad \text{Equation 3:}$$

Position and orientation may also be corrected by a gravity equation derived from a fusion of the IMU's accelerometer and gyroscope by means of a Kalman filter sensor fusion, as detailed in US Patent Application 2016/0377451A1.

$$N \cdot G_{rx} = G_{tx} \qquad \text{Gravity equation:}$$

A portion of the gravity equation can be substituted for direction of the distortion field ("v"). This substitution simplifies the distortion field to the roll about gravity, which reduces the number of unknown variables and makes the equation more easily solved. The equation is easier to solve because it reduces the degrees of freedom (DOF) of N (orientation) from 3 angles to just 1 (roll about gravity). See U.S. Pat. No. 10,162,177 for more information. Substituting the direction of the distortion field ("v") in equation 3 with Grx yields equation 4:

$$X = N^r B(r) + G_{rx} \cdot P \quad \text{Equation 4:}$$

7 parameters must be determined to solve equation 4:
θ—roll angle of N
r—3D position vector
P—distortion gains The Sigmat has 9 values (9>7) so a unique solution is probable. Solving the equation analytically is difficult, however iterative optimization methods offer a simpler solution through the use of a Jacobian. (e.g. Levenberg-Marquardt algorithm).

$$F(\theta, r, P) = \|N(\theta) t B(r) + Grx \cdot P - X\|^2 \quad \text{Equation 5(SOLVER 1):}$$

First, (θ, r) are initialized using an analytic dipole solution (ignoring distortion) or by tracking, initialize P=(0,0,0). Next, the Jacobian of F(θ, r, P) is computed using numerical derivatives. The Jacobian is used to compute a step which decreases F. A final calculation step is to perform iterations until some tolerance is achieved. The value of corrected PnO is then compared to measured PnO to determine the ratio of unexplained Sigmat and confidence intervals. Equation 6 is used for blending the three solvers.

$$E_x = (\|X_{PnO} - X_{measured}\|) / (\|X_{Measured}\|) \quad \text{Equation 6:}$$

When EM+IMU fusion provides the constraint, the equation becomes:

$$X = N_r B(r) + v \cdot P \quad \text{Equation 7(SOLVER 2):}$$

Where N=Nfusion

Electromagnetic and Optical Coordinate System Merger

In some embodiments, the electromagnetic tracking system is self-referential, where PnO is only established relative to a wearable emitter with unknown global coordinates. A self-referential tracking system can be merged with a global coordinates system in many ways. In one example, the present invention includes a camera 0301. The camera 0301 records and analyses images of the player's surroundings to establish an anchor point (e.g. a (0, 0, 0) point). The movement of this camera 0301 is calculated as movements relative to this global coordinate anchor point.

The present invention typically includes a sensor 0302 configured to enable the tracking system's translation from self-referential coordinates to global coordinates. Such a sensor 0302 has a fixed position relative to the camera system. This fixed position provides a known distance and orientation between the self-referential coordinates and the global coordinate, allowing their merger, as described in U.S. Pat. No. 10,162,177.

When merged, the benefits of both coordinate systems are maximized while the downsides are minimized. Anchoring a tracking system in real space and accurately positioning the player, as a whole, in VR is best achieved by an optical system. However, an optical system is limited by line of sight and is therefore not ideal for determining player positional nuances, such as limb location and other body configuration information. On the other hand, an electromagnetic system is excellent at tracking limb position and body configuration, but typically requires a stationary emitter for position tracking relative to a real-world reference.

By combining the two systems, the entire system of sensors is optimized to be both mobile and accurate.

Processor(s)

The present invention uses one or more processors that execute a number of instructions, such as machine-readable instructions. The instructions including receiving, storing, processing, and transmitting tracking data from EM, optical, IR, IMU, and/or myoelectric sources. The tracking data may be communicated to the processor by either a wired or wireless communication link. Upon receiving tracking data, the processor may execute an instruction to permanently or temporarily store the tracking data as random access memory (RAM), read only memory (ROM), cache, flash memory, hard disk, or other suitable storage component. Such a memory component may be a separate component in communication with the processor or may be integrated into the processor.

Figure 10:
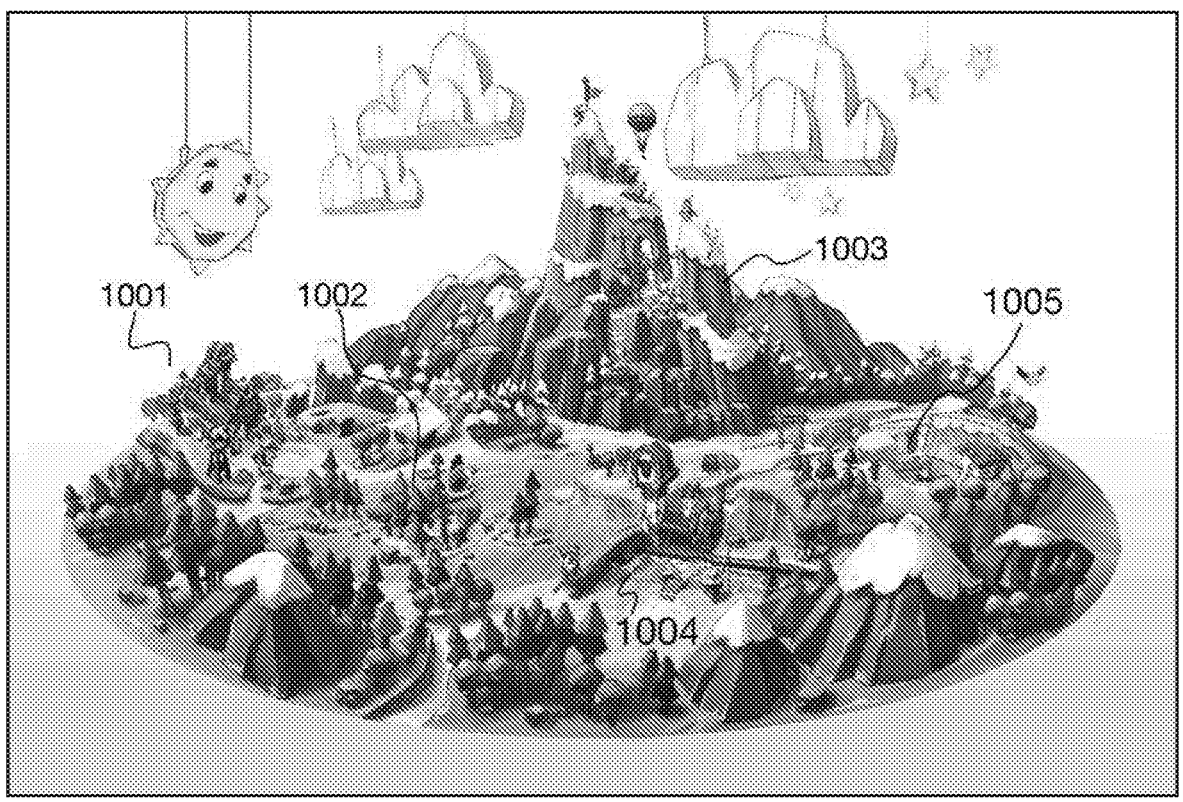
FIG. 10 illustrates an aerial view of the Happy Valley village virtual reality environment, in accordance with some embodiments.
Figure 12A:
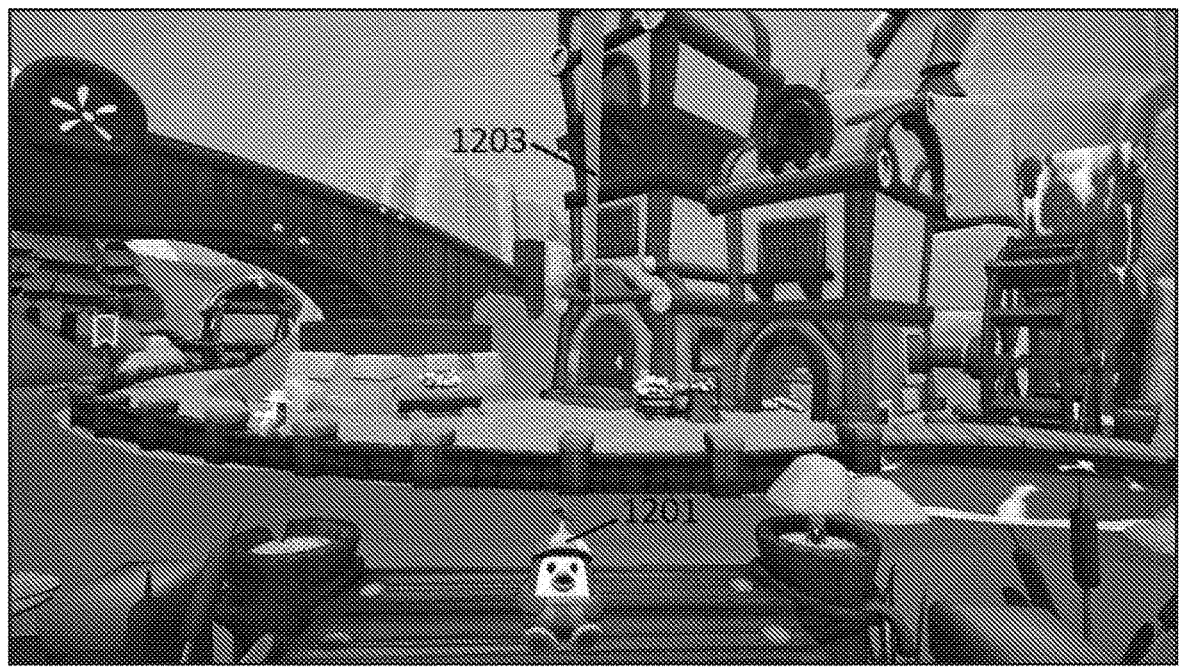
FIG. 12A illustrates a lobby game comprised of a gazing activity, in accordance with some embodiments.

The processor may also execute instructions for constructing an instance of virtual space. The instance may be hosted on an external server and may persist and undergo changes even when a user is not logged into said instance. Alternatively, the instance may be user specific and the data required to construct it may be stored locally. In such an embodiment, new instance data may be distributed as updates that users download from an external source into local memory. In either embodiment, the instance of virtual space may include a virtual volume of space, a virtual topography (e.g. ground, mountains, lakes), virtual objects, and virtual characters (e.g. non-player characters "NPCs"), as depicted in FIGS. 10 and 12A, for example. The instance may be constructed and/or rendered in 2-D or 3-D. The rendering may offer the user a first person or third person perspective. The instance may include properties of physics, such as gravity, magnetism, mass, force, velocity, and acceleration, that cause the virtual objects in the virtual space to behave in a manner at least visually similar to real objects in real space.

The processor may execute a program for analyzing and modeling tracking data. For instance, the processor may execute a program that analyzes the tracking data it receives according to the equations described above, along with other related pertinent mathematical formulas. Such a program may incorporate a graphics processing unit (GPU) that is programmed to translate tracking data into 3-D models. The GPU may utilize mesh puppetry, a skeleton rig, vertex animation, a shader engine, an inverse kinematic (IK) engine, and/or similar animation tools. In some instances, the CPU may at least partially assist the GPU in making the necessary calculations. This allows the GPU to dedicate more resources to the task of converting 3D scene data to the projected render buffer. The GPU may refine the 3-D model by using one or more algorithms, such as an algorithm learned on biomechanical movements, a cascading algorithm that converges on a solution by parsing and incrementally considering several sources of tracking data, an inverse kinematics engine, a proportionality algorithm, and other algorithms as known in the art of data processing and animation techniques. After the GPU constructs a suitable 3-D model, the processor executes a program to transmit data for the 3-D model to another component of the computing environment, or to a peripheral component in communication with computing environment, that is capable of displaying the model. In one embodiment, the GPU transfer the 3-D model to a video encoder or a video codec via a bus, which then transfers information representative of the 3-D model to a suitable display. The 3-D model being representative of a virtual entity that can be displayed in an instance of virtual space, e.g. an avatar. The virtual entity is capable of interacting with the virtual topography, virtual objects, and virtual characters within virtual space. The virtual entity is controlled by a user's movements.

In one embodiment, a processor may execute instructions for a supervised learning algorithm that predicts position and orientation when tracking data is limited or unreliable. The algorithm is trained to weight different prediction techniques based on the type and amount of available tracking data. The algorithm may be trained to predict anthropomorphic movements with a forward and backward reaching inverse kinematics ("FABRIK") engine, to identify and replicate repetitive movements with a frame-by-frame analysis, and to match prior positions and partial tracking data with positions in a key pose library. The algorithm will generally weight FABRIK solvers as more reliable when tracking data for an end effector is available. Alternatively, the algorithm will generally weight a frame-by-frame prediction or matching prediction as more reliable when tracking data for an end effector is lacking.

The algorithm may utilize a FABRIK solver to predict position and orientation when tracking data is lacking. A FABRIK solver uses a two-bone inverse kinematic chain to determine movements of a skeleton that reposition an end effector to a new, tracked location. The joints of the skeleton are restricted to only allow anatomically correct movements relative to a known end effector location. This may be achieved by restricting joint mobility. Translational movement may be restricted with a bounding box and rotational movement may be restricted according to a maximal anatomically possible range of motion. Similarly, the degrees of freedom of any joint may be limited to six degrees of freedom or less. If tracking data for an end effector is lacking, the algorithm may weight FABRIK solver solutions lower and may rely more heavily on other prediction methods.

In one example, an algorithm receives a first level of training where, the algorithm is provided with a complete series of tracking data for a repetitive exercise and is tasked with applying a smoothing function for gaps in the data that produces a finished series of tracking data with no gaps and smooth and continuous exercise movements. For a second level of training in this example, the algorithm is provided with a series of tracking data where the last frame is missing at least some of the tracking data. The algorithm is then tasked with predicting in near live time (e.g. faster than $\frac{1}{60}^{th}$ of a second) the complete tracking data for the last frame by identifying patterns in movement in the series of tracking data, wherein the algorithm identifies clusters of frames with repetitive movements and assumes continued adherence to the repetitive motion for the last frame.

In one example of a third level of training, the algorithm is provided with a set of training data that is restricted across some joint, so movement information beyond the joint must be predicted based on the movements of adjacent body parts alone. In other words, the tracking data lacks an end effector and position and orientation must be predicted based on identifying repeated clusters, with a key pose match, or some combination thereof. For instance, tracking data for fingers may be categorically unavailable or temporarily lacking. The position of the fingers may be rendered according to matches in a library of key poses, wherein the match is based on position, orientation, directionality, and velocity of hand, metacarpus, wrist, or arm movement alone.

In another example of a third level of training, the learning algorithm may be trained to predict position and orientation by consulting a library of key poses. A key pose library may be filled with tracking data for common position and orientations a player finds themselves in when performing exercises. In one example, the available tracking data is compared to the key pose library. The available tracking data may include past frames of complete tracking data and one or more recent frames of partial tracking data. This available tracking data is compared to individual key poses and to blend spaces between two or more key poses to search for strong matches. The algorithm may reject matches between partial tracking data and a given key pose if rendering the key pose would result in a jerk or teleportation. For instance, if the tracking data at time 0 was complete and at time 1 was lacking arm position, the algorithm will compare the partial data to key poses. The algorithm may then reject a key pose with a perfect match to the partial data of time 1 if the arm position of the key poses is not close in position and orientation to the arm position of time 0. Only a small amount of movement is allowed from frame to frame (typically 60 frames are animated per second) to ensure smooth and continuous animations. The algorithm may further utilize a cluster function to identify patterns and match key poses in sync with the cluster's pattern and render the missing data accordingly. The strength of a match may be optimized with a weighting function that weighs joints close to the missing data more than joints and body parts distant from the missing data when assessing strength of a match with a key pose. In some instances, individual key poses may have an associated directionality, a velocity vector transformation function, or both. For instance, tracking data indicating a hug position may render the fingers as curling in when advancing towards the hug, while the fingers splay out when retracting from the hug. In this way, a single key poses may have two or more associated hand positions dependent on directionality. Furthermore, the degree to which the fingers curl in or stretch out may be proportional to the speed at which the arms are moving. The algorithms discussed here are typically supplied with a large amount of training data sets. After the algorithm provides an output for each training data set, the output is compared to the correct output and the nodes of the algorithm are reweighted according to their contribution to the correct or incorrect output.

In another embodiment, a processor may execute instructions for a cascading algorithm that converges on a solution by parsing available data and analyzing the parsed data incrementally. For instance, the cascading algorithm may utilize EM tracking data, camera tracking data, IMU tracking data, proportionality parameters, and constraint parameters. Convergence is achieved, in one example, by assessing the last 3-D model and defining constraint parameters for maximal movement across each joint in the given time frame. The algorithm then searches the EM tracking data for a solution satisfying that constraint. This solution is compared to available IMU tracking data and modified accordingly. The algorithm then takes that solution and refines it according to proportionality parameters that define appropriate angle, lengths, and distance between various body parts. Refinement may be achieved using least squares, standard deviations, an average, or a median method and may disregard data that significantly deviates from the rest (e.g. outliers). If available, the algorithm then consults camera tracking to verify that the solution accurately represents the user's movements and body position as captured by the camera(s). The algorithm may repeat one or more of these steps to reach convergence on an acceptable solution and the algorithm may temporarily, permanently, or continually modify the order in which the steps are executed to reach convergence more quickly. Convergence is achieved when the algorithm achieves an acceptable degree of confidence that the correct solution has been identified. For some portions of the avatar, where accuracy is not absolutely crucial, this confidence level may be lower, such as leg position when seated. For other portions, this confidence level may be higher, such as hand position and orientation. The animation of high priority body parts may receive processing prioritization to ensure animations do not exhibit visible latency. Animation prioritization may be achieved through streamlining the animation pipeline in software, hardware, or a combination of both, as described in U.S. Pat. No. 8,520,010.

Visual Display

In a preferred embodiment, the computing environment generates a 3-D model of the user, an instance of virtual space, and then communicates that information for display. An audio and visual display may be in communicable connection with computing environment by a head mounted display (HMD), as typical in VR systems, a television, a high-definition television, a monitor, or the like. The audio and visual display may be visualized on a cathode ray tube (CRT) display, light-emitting diode display (LED), plasma display panel (PDP), organic light-emitting diode (OLED) display, liquid crystal display (LCD), electroluminescent display (ELD), and other visualization hardware as known in the art. In one embodiment, a user's movements in physical space are mapped onto a 3-D model and at least a portion of that model is rendered in virtual reality, which the user can see and control (e.g. an avatar). In another embodiment, the displays of the virtual 3-D model are replicated on a physical 3-D model, such as a prosthetic limb.

Example System

In general, the computing environment utilizes PCBs with sensors, processors, GPUs, and other peripheral computer components to collect tracking data, map tracked movements onto an avatar, display at least a portion of the avatar for a user, and display a virtual reality environment.

In a more specific embodiment, the present invention utilizes a tracking system comprised of multiple, independent PCBs, a head mounted display (HMD) 0300, and a camera 0301 to wirelessly track user movement accurately and precisely. Each PCB typically supports an electromagnetic (EM) sensor 0101, which may be comprised of an EM receiver and an EM emitter. The HMD 0300 typically houses the camera 0301, an EM sensor 0302 at a fixed distance from the camera 0301, and a visual display 0304 for viewing virtual reality. The HMD 0300 may also act as the host of the tracking system by including a processor and graphics processing unit (GPU) configured to track the movements of the user, generate an avatar representing the user, and generate a virtual reality environment. In total, eleven or more electro-magnetic sensors and emitters may track body position and orientation.

Figure 4:
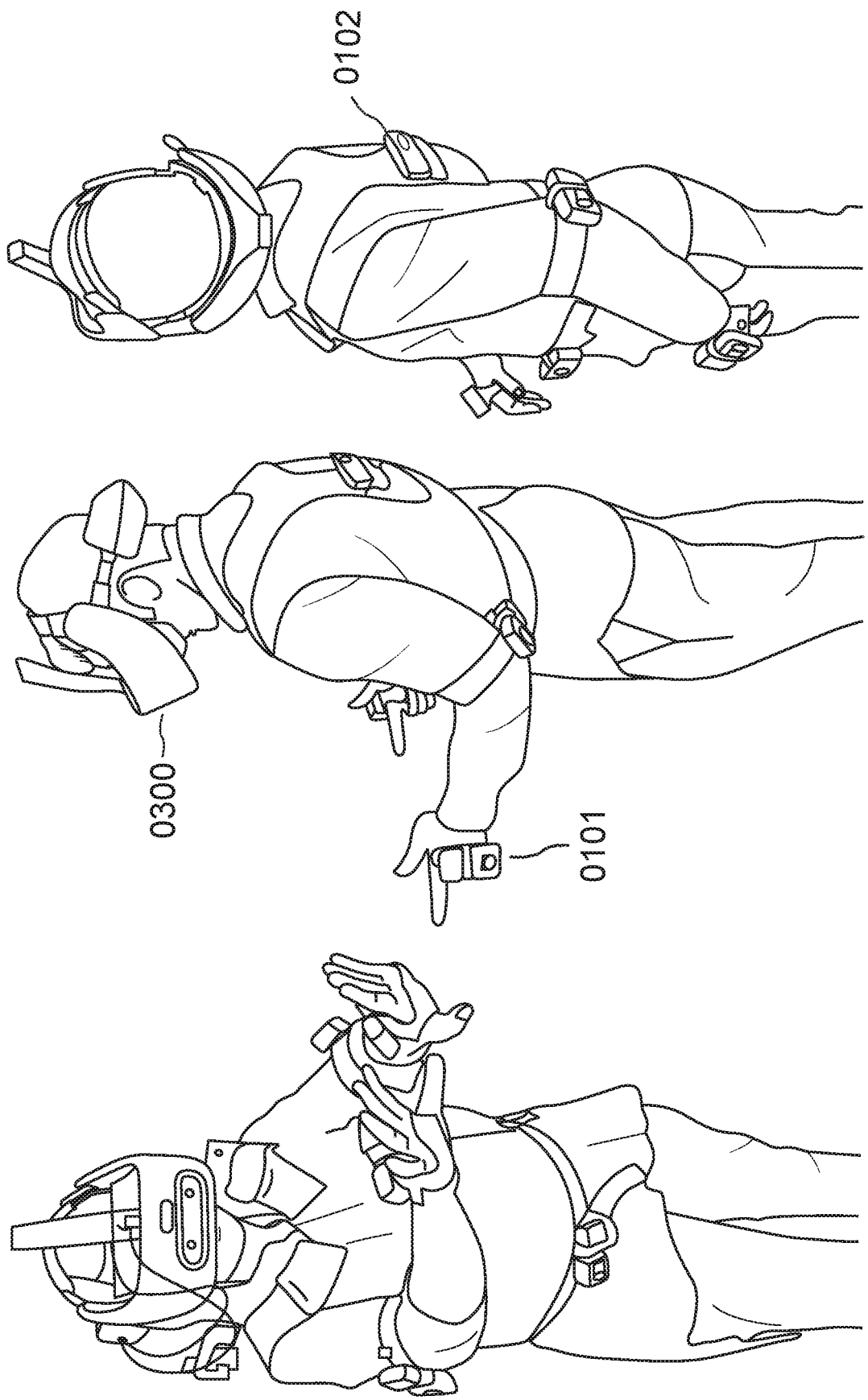
FIG. 4 illustrates a player fitted with sensors and an HMD, in accordance with some embodiments.

FIG. 4 illustrates an example of a user fitted with an HMD 0300, sensors 0101 on the wrists, elbows, and waist, and a sensor 0102 on the back, collectively, the "modules." Sensor 0102 may function as a wearable EM emitter and EM receiver, while sensors 0101 function as EM receivers. In another embodiment, the system also includes sensors on the knees and ankles as depicted in FIG. 5.

Figure 5:
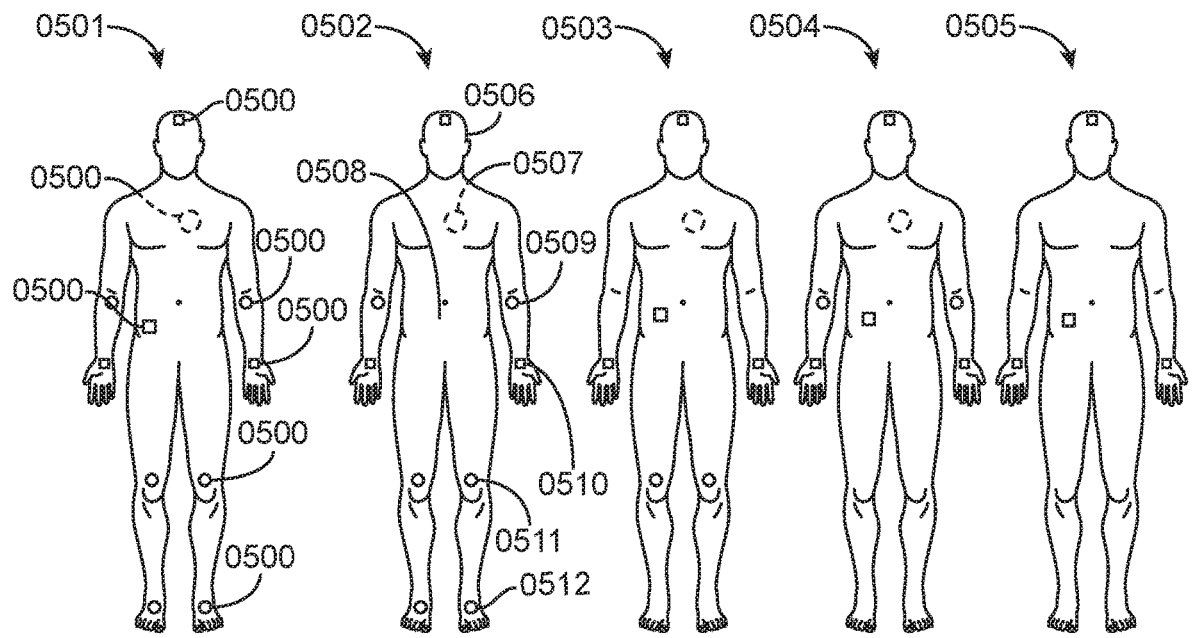
FIG. 5 illustrates placement options for sensors, in accordance with some embodiments.

FIG. 5 illustrates sensor 0500 placement options. In a first example 0501, the sensors 0500 are attached to the head 0506, the back 0507, the waist 0508, the elbows 0509, the wrists 0510, the knees 0511, and the ankles 0512 for a total of eleven sensors tracking player movement. The sensor placement of this example 0501 is optimal for accurately tracking the movements of an entire body. In other embodiments, some but not all of these sensors are attached to a player. In a second example 0502, the sensors 0500 are attached to the head 0506, the back 0507, the elbows 0509, the wrists 0510, the knees 0511, and the ankles 0512 for a total of ten sensors. In a third example 0503, the sensors 0500 are attached to the head 0506, the back 0507, the waist 0508, the wrists 0510, and the knees 0511, for a total of seven sensors. The sensor placement of this example 0503 enables nearly full body tracking with untracked movements of the elbows and feet being predicted and animated based on the movements of tracked body parts. In a fourth example 0504, the sensors 0500 are attached to the head 0506, the back 0507, the waist 0508, the elbows 0509, and the wrists 0510, for a total of seven sensors. This setup is optimized for tracking the upper body and is useful for tracking exercises performed while sitting. In a fifth example 0505, the sensors 0500 are attached to the head 0506, the waist 0508, and the wrists 0510, for a total of four sensors. This setup may track arm and spine movements well. Typically, sensors are attached to at least the wrists for exercises requiring arm movement, the waist sensor for exercises requiring leaning, and the ankles for exercises requiring leg movement. In any of the forgoing embodiments, cameras mounted on the player may assist in tracking.

Orchestration

In one embodiment, the HMD 0300 (aka Host) orchestrates the operation of the various modules and acts as the conduit between the various modules. In one example, the host sends upstream information via radio frequency (RF) to other modules. Upstream information may include frequency shift, LED color shift, autosyncing guidance, and other various commands. In this example, the various modules send downstream information via RF to the host, such as sync status and calculated PnO.

Auto Sync Protocol

Each of the wearable sensors 0500 are initially unassigned. In a preferred embodiment, upon startup and placement, the sensors 0500 will begin to auto-sync. Auto-body-positioning allows for seamless, error-proof setup, and requires no manual input. Once the sensors 0500 are placed on the body, the system automatically determines where on the body each sensor has been placed and assigns them as such. This auto-syncing feature improves on ease of use by simplifying and expediting the process of starting the system, so physical therapy can be started quickly. In one example, the sensors placed on the body provide PnO data relative to a sensor with an emitter worn on a user's back. The PnO data is then analyzed by the host to determine the positioning of the various sensors. Two variables can be used to determine the location of every sensor, height and hemisphere (e.g. right or left side). The sensor with the highest position is easily identified as the sensor on the HMD. The sensors having a height closest to the emitter sensor are assigned as the left and right elbows, respectively. Moving down, three sensors are positioned at about waist height. A middle-most sensor at this height is assigned as the waist sensor, and the left sensor is assigned as the left wrist and the right sensor is assigned as the right wrist. The knee and ankle sensors are similarly identified by their hemisphere (left or right) and their height. Although the variable height and hemisphere were used in the example above, this should be understood as a simplification of one way to achieve auto-syncing. For instance, the magnetic field vectors received at each sensor must be processed before height and hemisphere can be determined. The magnetic field vectors may alternatively be processed to determine absolute distance from an emitter. Additionally, if the player moves his or her arms, accelerometers inside the sensors may help identify the wrist and elbow sensors. During arm movements, typically the wrists will have the greatest acceleration of all the sensors, and the elbows will an acceleration lower than the wrists and higher than the other sensors. The rest of the sensors may then be determined by height alone. The present invention may use other such processing methods, as known by those with skill in the art, or combinations of such methods, to determine relative sensor location.

Avatar

Figure 6A:
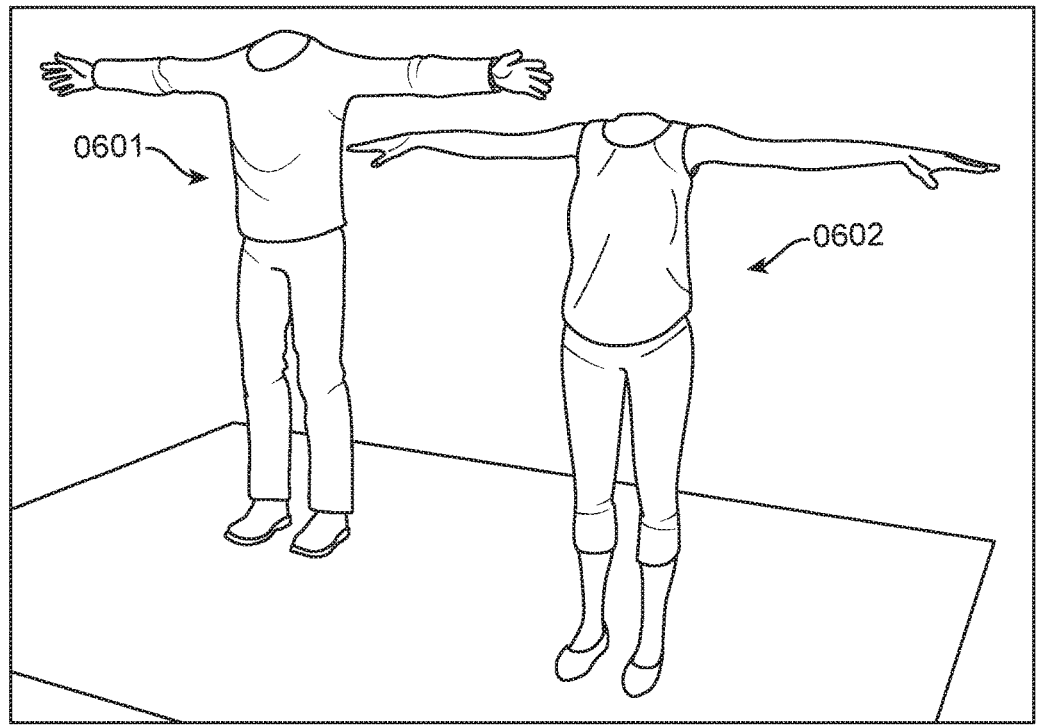
FIG. 6A illustrates a male and female avatar, in accordance with some embodiments.
Figure 7:
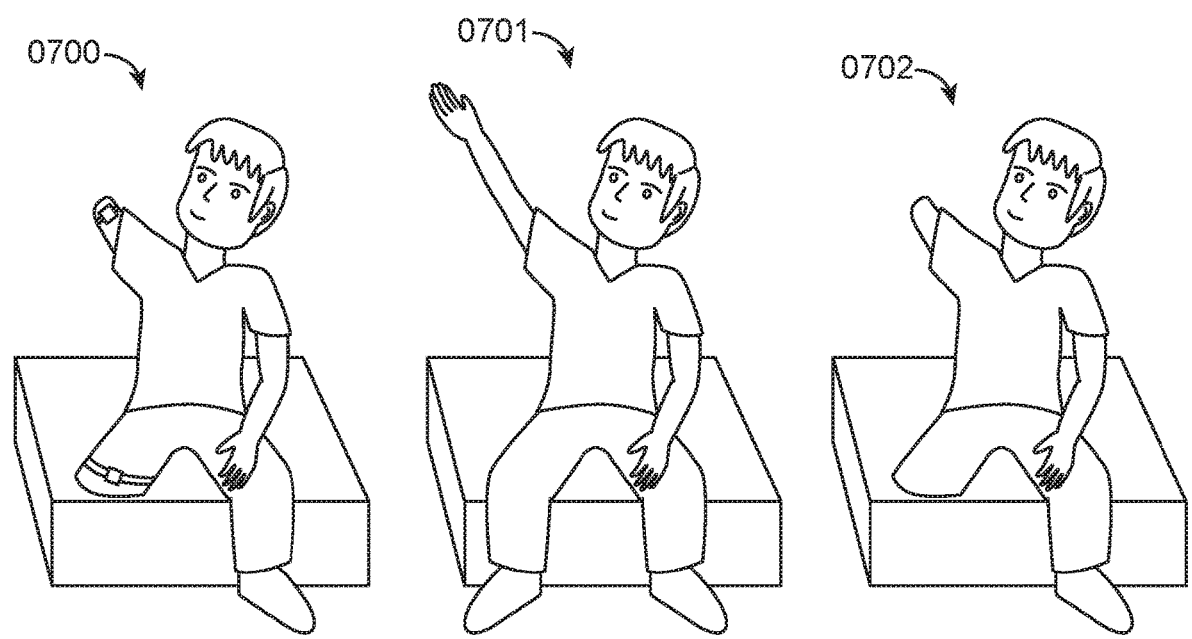
FIG. 7 illustrates an avatar rendered to not match the player, in accordance with some embodiments.

FIG. 6A illustrates a male avatar model 0601 and a female avatar model 0602. The player typically selects an avatar while setting up the system. In some embodiments, the avatar may be further customized with a character creation option. Character creation may allow for the selection of gender, body type (height/weight), clothing, skin and hair color, and allows for the selection of accessories or paint on the hands, nails, wrists, or fingers. This customization beneficially amplifies the player's feeling of immersion by making the avatar look like the player. The more detail and accuracy the avatar has, the greater the game will create and maintain an illusion of realism within the virtual world. If a player 0700 is missing a limb an avatar 0701 may rendered with the missing limb, as illustrated in FIG. 7, or an avatar 0702 may be rendered without the missing limb. The system includes an input for adjusting such features of an avatar. If a missing limb is rendered, its movements may be predicted and animated based on the movement of nearby tracked limbs.

Figure 6B:
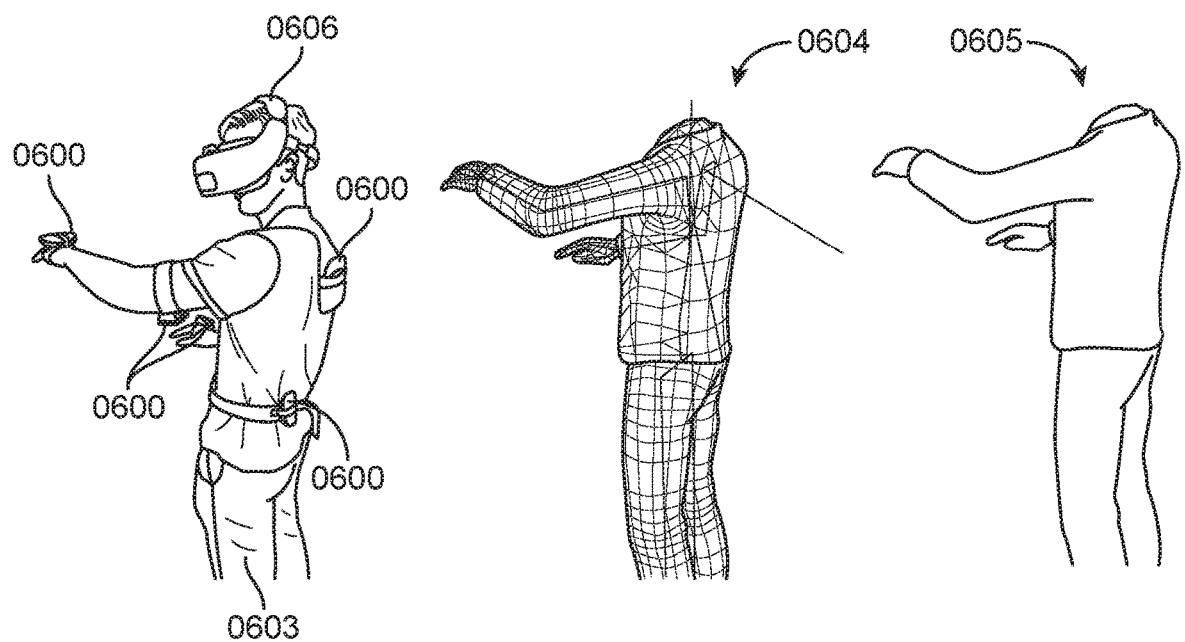
FIG. 6B illustrates an animation pipeline for rendering an avatar, in accordance with some embodiments.

FIG. 6B illustrates an animation pipeline for rendering an avatar. The animation pipeline starts by collecting tracking data from sensors 0600 worn by a player 0603. This tracking data is collected and processed to form a 3-D model 0604 of the player's body. The collection of the data may be achieved by the host 0606 and the data may be processed by a processor, a GPU, or some combination thereof. The 3-D model 0604 may be comprised of virtual bones, and a virtual skin or mesh as discussed in more detail below. Once a proper 3-D model 0604 is determined for the player's latest movements, a surface of the model is animated as an avatar 0605 in the virtual reality environment for the player to see and control. It is imperative that this pipeline is executed quickly so that there is a near unperceivable delay between collecting tracking data and animating the avatar exhibiting tracked movements in the virtual reality environment. A delay between a player's movements and their avatar's movements diminishes the player's sense of immersion in VR. In some embodiments, the avatar is animated without a head. A person typically cannot see their head, so this is usually not an issue. In some embodiments, the virtual reality environment may include a mirror or mirrored surfaces. In such instances, the avatar may be animated with digital rendering of the player's face, which may show up in the mirrors and mirrored surface.

In one example, the avatar includes virtual bones and comprises an internal anatomical structure that facilitates the formation of limbs and other body parts. Skeletal hierarchies of these virtual bones may form a directed acyclic graph (DAG) structure. Bones may have multiple children, but only a single parent, forming a tree structure. Two bones may move relative to one another by sharing a common parent.

Virtual skin may surround the virtual bones as an exterior surface representation of the avatar. The virtual skin may be modeled as a set of vertices. The vertices may include one or more of point clouds, triangle meshes, polygonal meshes, subdivision surfaces, and low-resolution cages. In one embodiment, the avatar's surface is resented by a polygon mesh defined by sets of vertices, whereby each polygon is constructed by connecting at least three vertices.

Each individual vertex of a polygon mesh may contain position information, orientation information, weight information, and other information. The vertices may be defined as vectors within a Cartesian coordinate system, whereby each vertex has a corresponding (x, y, z) position in Cartesian space. In alternative embodiments, the virtual bone transformations may be defined as vectors in quaternion space, whereby each bone has a corresponding (1, i, k, j) position in quaternion space. Quaternion representation of rotation for bone transformations beneficially avoids gimbal lock that temporarily reduces a tracked object's degrees of freedom. Gimbal lock is associated with tracking and, thus, animation errors.

The movement of the avatar mesh vertices with the skeletal structure may be controlled by a linear blend skinning algorithm. The amount each vertex is associated with a specific bone may be controlled by a normalized weight value and can be distributed among multiple bones. This is described more fully in the Skeletal Animation section below.

The surface of the avatar is animated with movement according to either vertex animation, skeletal deformation, or a combination of both. Animation techniques include utilization of blendspaces which can concurrently combine multiple drivers to seamlessly and continuously resolve avatar movement. An example of using a blendspace is a strafing movement model which controls foot animation based on Avatar forward/backward and left/right movement. Another example is four hand shapes representing finger positions at different wrist rotation (up, down, in, out). In both examples each shape or animation pose is blended in depending on the degree to which its driver is currently active, i.e. how much the avatar has moved in world space or the currently tracked position of the wrist. Morph target shapes are stored offsets of affected vertices that can be blended in and combined with skeletal deformation to create more convincing deformation. An example of morph target animation is the bulging of a bicep muscle in response to forearm movement. Key pose interpolation is the skeletal movement of the avatar blending sequentially from pose to pose where the poses are defined by an animator setting key frame values on the bone transforms.

Special Mesh

Special avatar meshes may be implemented to enable some movement animations. Where movement animations are only indirectly related to tracking data (e.g. complementary movements), the avatar's body part forming the structure to be animated may be comprised of a mesh topology separate from the remainder of the avatar. As an example, the hands of the avatar may be comprised of a separate topology from the remainder of the avatar. The topology of such a hand is first formed into a 3D model. To achieve movement animations, the hand is then modified according to vertex animation, skeletal animation, or a combination of such techniques.

Skeleton Animation

In skeletal animation, the mesh of the 3D model of interest is fitted with a skeleton. In FIG. 6B the mesh is shown as a framework, while the bones are shown as lines, which may be labeled with "x," "z," and "y" axes. The Y-axis typically indicates the parenting relationship of the bones. Alternatively, these bones are labeled with (1, i, k, j)

axes labels, which correspond to quaternion coordinates. Each axis may be characterized as a mathematical vector. The parenting relationship allows bones to inherit the motion of their parent bones. The bones of the virtual skeleton may or may not precisely mimic the joints seen in typical human anatomy.

Each bone of the skeleton forms a transformation which influences all vertices associated with the bone. The amount of influence each bone has on each vertex is controlled by a weighting system. In one skeletal animation approach, finger articulation is carefully executed in real-time according to inverse kinematics (with fingertip locations serving as end effectors) to animate intuitive flexions and realistic range of motions for an in-game avatar. For a vertex animation approach, the skeleton of a 3D model is manually manipulated across the joints to form particular poses of the 3D model. These poses are sometimes called deformations, in that they are deformations of the original 3D model. These deformations are saved as offsets or deltas from the original model in order to be used as key poses for a vertex animation approach.

Vertex Animations

In a vertex animation approach, movement animations may be executed as interpolations between morph targets. A morph target is a new shape created by a copy of the original polygonal mesh with vertex order and topology being maintained and then moving the vertices to create the new desired shape. The morph target is then saved as a set of 3D offsets, one for each vertex, from the original position to the new target position of that vertex. Every deformation made of the model to be animated exists as a key pose or morph target across a variety of triggering mechanisms. For the animation of a hand, movement is animated as an interpolation between the neutral shape and the one or more target shapes. At a basic level applying a morph target is moving each vertex linearly towards its target shape in the direction of the saved offset vector. The amount of activation of the blendshape is controlled by its weight. A weight of 1.0 activates the full target shape. A weight of 0.5 would move each vertex exactly halfway towards the target position. Multiple blendshape targets can be active at once with each controlled by its own weight value. As the weight of blendshapes change over time, smooth interpolation between intermediate shapes is achieved.

To appear realistic, the morph image must be proportionally morphed between its one or more poses. For hand animations, this means that finger movement animations must be animated both in proportion to wrist movement and with the same directionality. This movement is achieved by applying a driver mechanism across each vertex of the polygon mesh. The driver mechanism may execute a mathematical transformation that generates a morph shape that is linearly related to the degree of wrist flexion or has a curved relation to the degree of wrist flexion.

In the case of linear relationship between wrist flexion and finger movement, 25% of wrist flexion from neutral will cause an animation that is 25% deformed towards said key pose and 75% deformed towards the neutral pose. If wrist flexion is angled towards more than one key pose, then hand animations are interpolated proportionate to the proximity of nearby key poses and the neutral pose. For instance, a wrist flexion measurement of 33% "in" and 33% "up" may cause the generation of a hand animation that is interpolated evenly between the hand model's neutral pose, "in" pose, and "up" pose. This middle pose exists within the blend space of these three individual poses.

A curved relationship between wrist flexion and finger movement may generate a different animation for a given wrist flexion when compared to a model utilizing a linear relationship. Assume a hand is moving from the neutral pose to an "in" pose. During the first 25% of wrist flexion, the animation may traverse half the blend space and produce an animation that is 50% "in" and 50% neutral. In this way, the animation driver is accelerated at the front end. Showing half the of the hand model's blend space for only the first quarter of wrist flexion. The remaining half of the blend space is then slowed down on the back-end and spread out across three quarters of wrist flexion. Of course, this approach may be reversed, and hand animations may be slowed on the front-end and accelerated on the back-end.

The vertex animation approach may also utilize easing functions to accommodate rapid movements. Rapid movements may cause an animation technique to temporarily lose accuracy by improperly animating extreme hand poses. Thus, the rate at which a hand may enter or leave a pose is limited by an ease function. The ease functions act to temporarily slow down the display of animated movements. In essence, the ease function generates a lag time in reaching a particular pose when movements are deemed too rapid. In addition, the ease function may avoid animation jerks from gimbaling events that occur during cartesian coordinate rotations.

Although animation techniques have been described in reference to wrist, hands, and finger animation, it should be understood that the same animation principles are applicable to other body parts of the avatar. Additionally, the positions determined by such techniques may inform either a specific animation or a specific movement for a prosthetic.

Special Poses and Gestures

In some embodiments, animations may take on more complex movements when the system tracks triggering gestures. For instance, while interacting with a virtual bird within a game, a player's action of reaching out to the bird may trigger the display of a pre-recorded movement animation for the hand of the player's avatar. In one example, when tracking data indicates that a player has reached towards a bird with their palms facing upwards, the avatar will be rendered with the palm facing up, and the fingers opening to allow the bird to land. In another example, when tracking data indicates that a player has reached towards a bird with their palms facing down, the avatar will be rendered with the palm facing down and the index finger at full extension, while the rest of the fingers are curled in, whereby the bird lands on the avatar's index finger.

The present invention may compare tracking data (across several frames) to a gesture library to identify when a user has performed one or more gestures. The identification of a gesture may trigger an animation protocol. During an animation protocol, instead of rendering an avatar according to the user's movements, the avatar is rendered according to a combination of the user's movements and one or more pre-recorded animations. The identification of a gesture does not necessarily cause the next visualized frame to show the gesture animation. Instead, in one example, the gesture animation is introduced gradually. For instance, the last tracked position will be blended with the final gesture position. In one embodiment, the transition between last tracked position and final gesture position takes around one second, whereby the transition is spread across around 60 frames, with each successive frame being rendered with animations closer to the final gesture position.

One example of a gesture within the gesture library is a waving gesture. In one embodiment, when tracking data indicates that a user has moved their wrist back and forth while pivoting an otherwise stationary forearm, or as a smooth back and forth arc of the wrist and forearm. In the avatar may render a pre-recorded waving animation. In other embodiments, the waving animation is modified to reflect the speed at which the player is moving, modified to reflect the angle of the hand relative to the forearm, and/or modified to match the length of time the gesture is conducted. In essence, the gestures do not wholly take over rendering, instead they are blended with the tracking data, whereby gestures are executed partially according to tracking data and partially according to pre-recorded animations. Optionally, the waving gesture is accompanied with a "hello" audio line.

Another example is a thumbs-up gesture. In one embodiment, when tracking data indicates that a user has extended their arm and then snapped their wrist down while their thumb is orientated up, then the system renders a pre-recorded thumbs motion for however long the pose is held. Similar triggers may exist for the knees, feet, and toes that may animate things such as kicking a ball or dancing.

The avatar's hands may exhibit motions not directly linked to the player's own motions. For instance, to breathe life into the hands of the avatar, the fingers may splay and stretch at given intervals of nonmovement. Such animations may also be displayed for the toes.

Tablet

Figure 8:
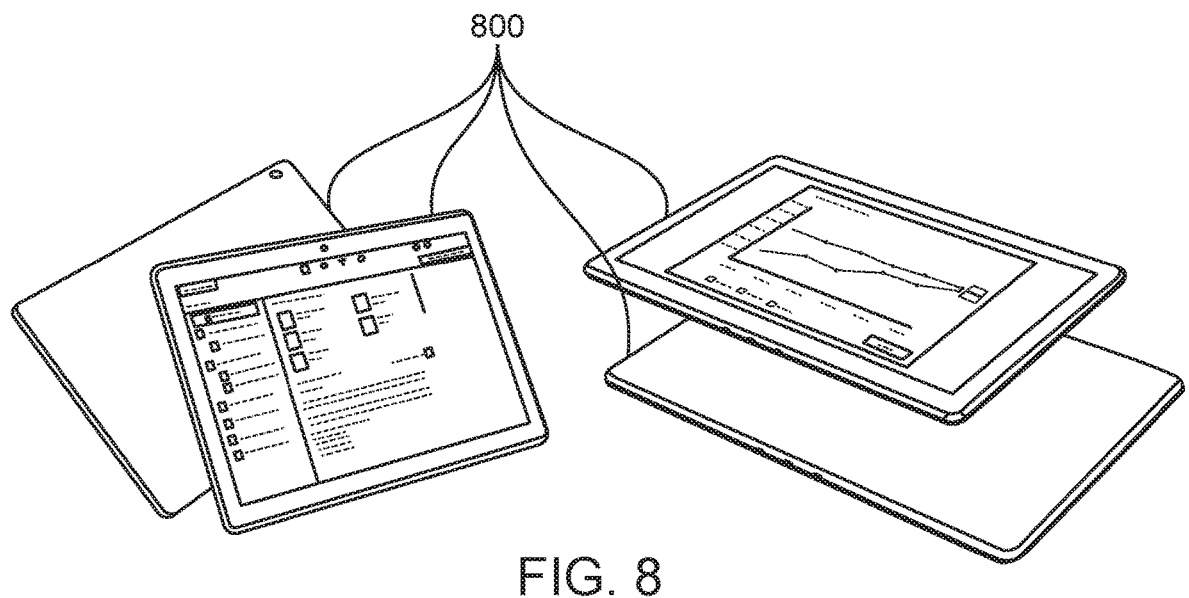
FIG. 8 illustrates a tablet computer for controlling aspects of the present invention, in accordance with some embodiments.

FIG. 8 illustrates a tablet computer 800 that may be included in the present invention. The tablet computer 800 may allow a user, PT, OT, or practitioner to control a player's virtual reality experience.

Figure 9A:
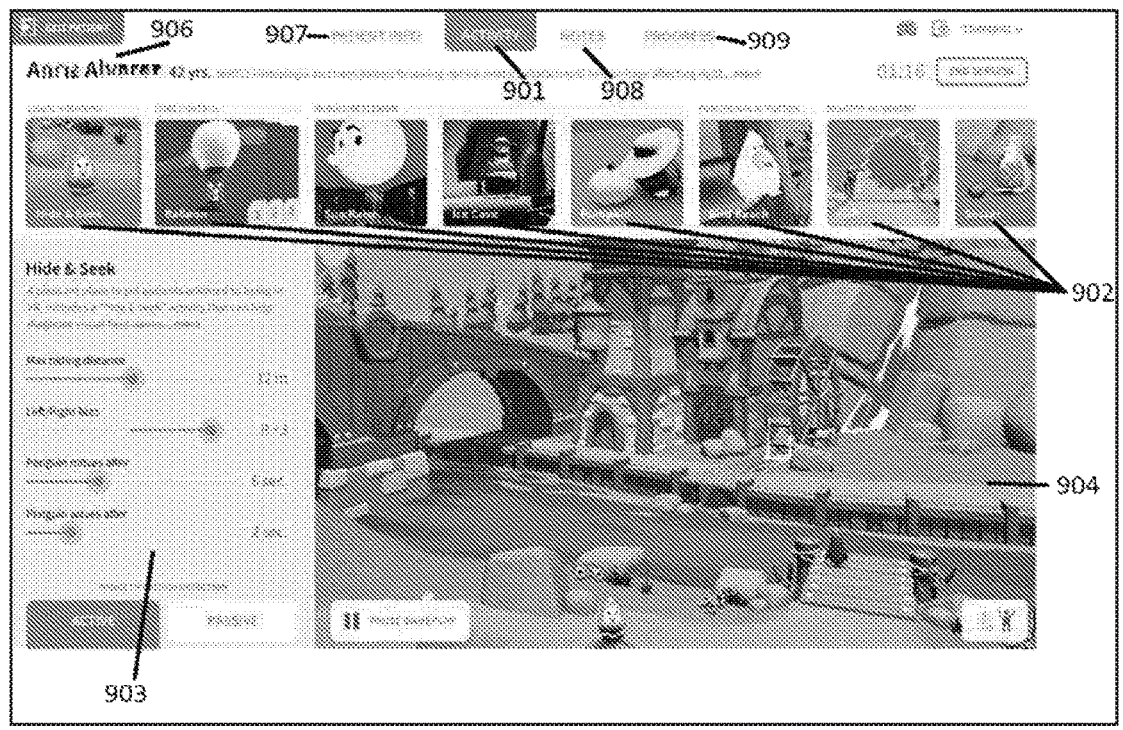
FIGS. 9A-9C illustrate examples of a control interface and tracking data presentable on the tablet computer, in accordance with some embodiments.

FIG. 9A illustrates an example graphical user interface (GUI) for controlling a virtual reality experience. The GUI may include an activity button 901. Once the activity button 901 is clicked, the GUI typically includes exercise buttons 902 for selecting therapeutic exercises, adjustment buttons and sliding bars 903 for adjusting exercise variables, such as difficulty, rep count, or side bias. The GUI typically includes a duplicate view 904 of the player's virtual reality view. The duplicate view 904 represents a real-time reflection of at least a portion of the player's view. In one example, the duplicate view 904 allows for touch screen interaction with the virtual reality environment. The GUI may include basic patient info button 906 on the activity screen and the GUI may offer more detailed info after pressing a patient info button 907. The GUI may include a notes button 908, which allow the user to take down notes. However, the tablet may cut down on the requirement for note taking because the tablet may record measurements, catalog assessments, and create progress data reports automatically, which may save the practitioner from manually performing such paperwork. The GUI may include a progress button 909 that allows the user to see past exercise performances and may offer progression and regression analytics and other relevant player history data. The tablet may allow communication with the player, either through audio, text, or villager proxy. The tablet may include an assistance button, a mid-line mirror button, an anti-gravity button, a sensor status (battery level, errors), an end session button, and sensor sync status indicators. The tablet 800 may include a button that generates an avatar for the tablet user that is animated in the player's virtual reality environment, wherein the user can provide guidance and/or support to the player within the game.

Figure 9B:
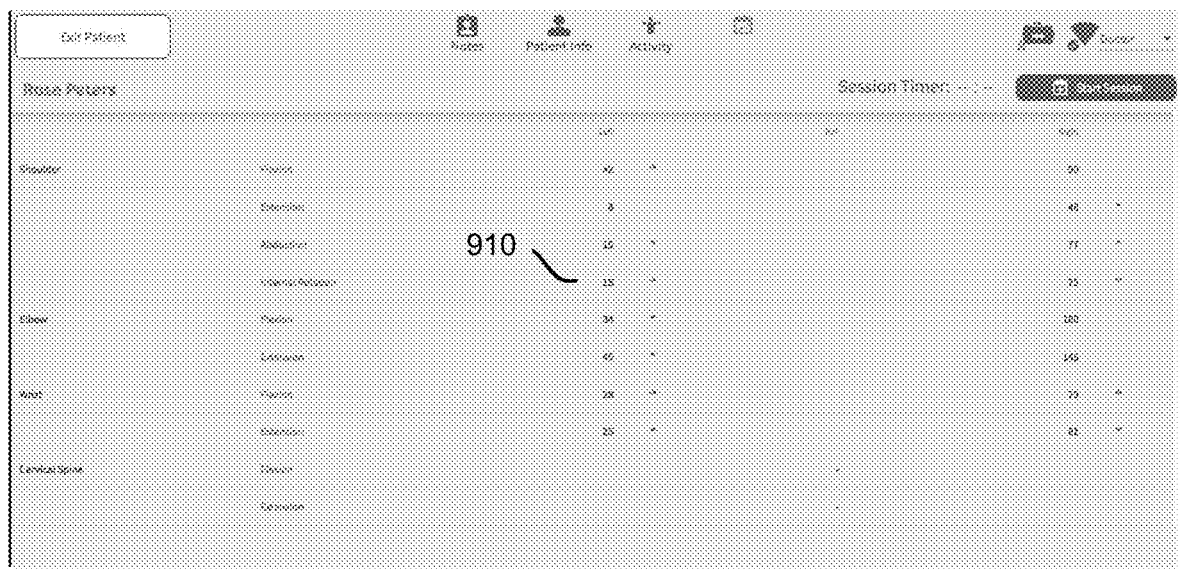
Figure 9C:
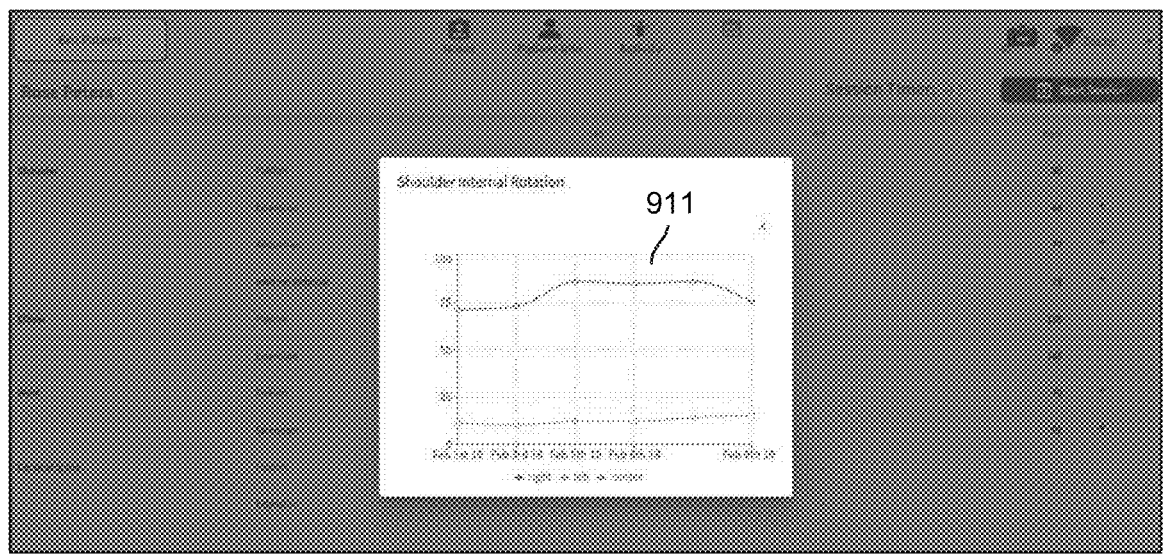

FIGS. 9B-9C illustrates examples of exercise analytics that may be offered on the tablet computer 800. The data may include range-of-motion data as angles achieved or as a percentage of a complete range-of-motion. The data collected may also include flexion, extension, abduction, adduction, distance traveled, supination, pronation, and rotation data for various joints of the player's body. The data may include reps completed and an assessment of posture during the exercises. The data may be presented in a list 910 or graphical format 911. A graphical format 911 may benefit from visually representing a player's progress from day to day of physical therapy. In one embodiment, the player's data is presented as range of motion on the Y-axis and date on the X-axis, whereby range of motion is shown for the player's left side, right side, or both sides. In another embodiment, a graph simultaneously displays a first performance, a last performance, a best performance, and/or a worst performance alongside the presently recorded data. In one example, player data is presented as a radar graph. In another example, range of motion is expressed a circle-like shape extending from a graph's 0,0 point. How far the circle-like shape extends on the x and y-axes may indicate the user's range of motion, speed, or fluidity. On such a graph, positive Y-axis, negative Y-axis, positive X-axis, and negative X-axis may each illustrate a different quantification of motion. Alternatively, such data may be presented graphically or on an anatomic model. For example, a 3-D model of the player may be presented to the tablet user. The 3-D model having selectable and highlightable axis of rotation (e.g. shoulder rotation, flexion, and extension). Upon selection of an axis, the tablet offers a presentation of the ROM data previously collected for the selected axis.

The HMD and the tablet may independently connect to the Wi-Fi of a common router, through which they may communicate. The system may connect to an external webserver and a cloud storage unit. A cloud infrastructure can provide data storage and analytics relating to treatments given and individual patient progress, which may be accessible via a practitioner application. A user may be provided with his or her own app or portal that allows access to progression data, session data, and appointment scheduling.

Exercises

When a player is fitted with sensors and immerses themselves in the virtual reality environment by donning the HMD they will find themselves in the Happy Valley. The Happy Valley is an escape from a potentially mundane and dreary hospital or doctor's office. This virtual reality environment is a vibrant paradise with games and activities designed to facilitate, encourage, and reward the performance of therapeutic exercises.

In short, the games may include gazing games that require the player to turn and look. A gaze game may be presented as a hide-and-seek game, a follow-and-seek game, or a gaze and trigger game. The games may include sun rising games that require the player to raise his or her arms. The games may include hot air balloon games that require the player to lean and bend. The games may include bird placing games that require the player to reach and place. The games may include a soccer-like game that requires a player to block and/or dodge projectiles. These games may be presented as sandbox games, with no clear win condition or end point. These are free play environments presented as an endless interactive lobby. The sandbox versions are typically used to introduce the player to the game mechanics, and it allows them to explore the specific game's unique perspective of the virtual reality environment. Additionally, the sandbox games may allow therapist to use objects to augment and customize therapy, such as with resistance bands, weights, and the like. After the player has learned how the game mechanics works, they can be loaded into a version of the game with a clear objective. In these versions of the game, the player's movements may be tracked and recorded. After completing the prescribed number of repetitions (reps) of the therapeutic exercise (a number that is adjustable), the game may come to an end and the player may be rewarded for completing it.

The transition from game to game is seamless. Several transition options may be employed. The screen may simply fade to black, and slowly reload through a fade from black. A score board or a preview of the next exercise may be used to distract the player during transition. A slow and progressive transition ensures that the patient is not startled by a sudden change of their entire visual environment. This slow progression limits the disorientation that occurs from a total, instantaneous change in scenery while in VR.

At the end of a game or exercise session, the player may be granted a particular view of the Happy Valley, such as a birds-eye view of the village. From this height, the players are offered a view of an ever-changing village. The changes in the village are a direct response to the player's exercise progression, and therefore offer a visual indication of progression. These changes will continue as the player progresses through the games to provide long-term feedback visual cues. Likewise, such views of the village may provide the best visual indicia of progress for sharing with family members or on social media. Positive feedback from family and friends is especially important when rehab progress is limited. These images will help illustrate how hard the player has been working and they will provide an objective measure of progress when, perhaps, physically the player feels little, if any, progress. This feature enhances the positivity of the rehab experience and fulfills the games overall goal to be positive as possible while to encouraging continued participation and enthusiasm.

Valley & Villagers

FIG. 10 illustrates an example of a birds-eye view of the Happy Valley. The Happy Valley will serve as the centerpiece to the player's experience. Each exercise the player performs may have a direct impact on the valley's environment, its villagers, or its animals. Typically, each rep and each set of an exercise has a direct correlation with desirable changes in the valley. The player's exercises may cause water to flow, ice to melt, crops to grow, wind to blow, the land to take shape, and the clouds to roll over ocean waves. Many of the exercises will have a direct correlation with a desirable elemental change in the valley. As the elements change, the valley's inhabitants will react accordingly. The waves may bring surfers and the sun may bring kids to the beach to build sand castles. The wind may blow in seabirds and fresh water may bring exotic fish. Fireflies and butterflies may buzz in the woods and around the player as exercises are performed and completed. Exercises may help a caterpillar metamorphize from a cocoon to a butterfly. Exercises may attract cats and dogs, who perform tricks. The player's exercise may cause the village to grow and the architecture of its buildings to become more intricate. Exercises may save villagers, feed animals, or simply just be fun pastimes. In this way, the player is first presented with an initial virtual reality environment and, through their participation in therapeutic exercises, subsequent virtual reality environments are generated that help signify short-term progression, long-term progression, or both.

Aesthetically, the valley is vibrant and magical and the player's exercises may enhance its vividness. Exercises may be linked to northern lights over the horizon, sparkling stars in the night sky, and other celestial bodies. In some exercises, the reward is an atypical view of the virtual reality environment. The player may be offered a view through a telescope, to see the cosmos, or the player may be given a kaleidoscopic view, where colors, textures, and shapes transform in fractal patterns.

FIG. 10 includes a farm 1001 where sunrise activities may be performed, an island 1002 where bird reach activities may be performed, a mountain 1003 where hot air balloon activities may be performed, a river 1004 were hide-and-seek activities may be performed, and a lake 1005 where soccer-like activities may be performed. The number and size of the buildings and structures in these and other areas may increase as the player completes games and therapeutic activities.

Figure 11:
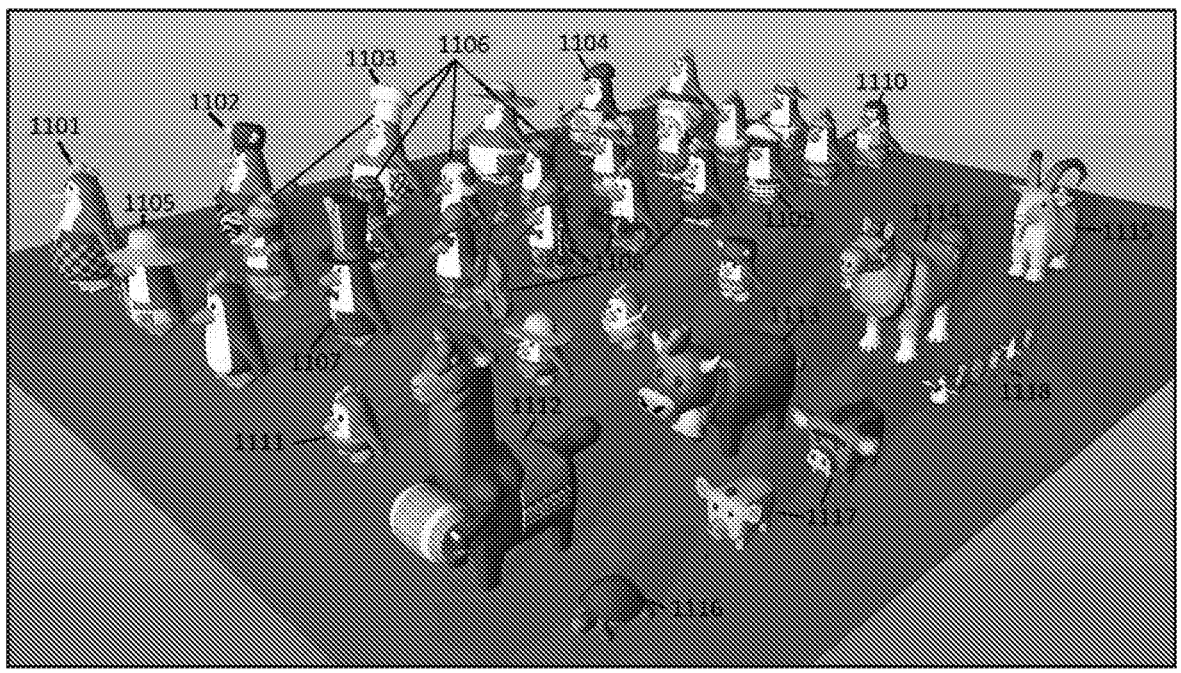
FIG. 11 illustrates virtual characters residing in the Happy Valley village, in accordance with some embodiments.

FIG. 11 illustrates a plethora of diverse and interesting villagers and animals (collectively "virtual characters") the player may encounter. Aesthetically, the villagers may look like penguins. The villagers interact with the player during exercises and their population may grow as the player progresses through physical therapy. When a player helps or rescues a villager, they may appear more frequently in other parts of the game. The villagers are generally expressive and responsive. When a player is performing an exercise, the villagers are typically encouraging, enthusiastic, and euphoric. The villagers may let loose balloons, play with kites, start building projects, and plant trees with joy after a patient completes an exercise. Throughout all the various exercises, a villager can typically be seen interacting with each other, animals, and objects within the valley. Sometimes the villagers may even be seen performing magic. The virtual characters may include a plaid clad penguin 1101, an ice cave penguin 1102, a chef penguin 1103, an artist penguin 1104, a fishing penguin 1105, mountaineer penguins 1106, mayor penguin 1107, band penguins 1108, boat captain penguin 1109, pilot penguin 1110, children penguins 1111, an alpaca 1112, a cow 1113, a horse 1114, a goat 1115, a turtle 1116, pigs 1117, birds 1118, and many others.

The villagers may or may not verbally communicate with the patient. In one embodiment, the villagers may use gibberish or gestures to communicate, and they may not provide exercise instructions for risk of conflicting with a medical professional's opinion/advice. In alternative embodiments, such as those for use at home, a lead villager, such as the mayor, may provide instruction and guidance to the player, and may even serve as a proxy for a physical therapist. The villagers or their leaders may make requests, relay the needs of the village, or plead for the player to perform certain therapeutic exercises. The villagers may also share personable back stories about overcoming adversity with the player between exercises. They may share lore about the village and its inhabitants. These characters may serve as a vessel to provide depth to the Happy Valley village. If the rewards are not enough for the player, perhaps vibrant stories about the heritage of Happy Valley may keep them engaged and wanting to learn more.

The general goal of any theme of the present invention is to transport the players to somewhere delightful, warm, empowering, enabling, and safe. This type of setting will provide an infrastructure for long-term progress, form feedback, and encouragement. In a typical setting, the player will take on the role of a sort of deity for the villagers. It is the player's responsibility to look after the welfare of their villagers. By performing exercises, the player will provide immediate, visible benefits to the villagers or collect and generate the resources they need to thrive, which will provide the player with a tangible short-term feedback mechanism. A player's gaze pointer acts as a sight line, and villagers may interact with the patient when the gaze pointer is on them.

The exercises are often tied to the specific needs of the villagers. The villagers may ask for help with a pumpkin growing contest, where the player raises the sun to grow the pumpkin. In other exercises, the villagers may ask for help rescuing a friend from a block ice, where the player raises the sun to free the frozen villager. During such exercises, villagers and animals will gather as the exercise progresses and cheer on the player. As the player comes to the last few reps, the mayor may come and congratulate the player and present them with a star or stamp on the player's stamp card, and the villagers may initiate a celebration to commemorate completion of the exercise.

The player's efforts may also be reflected in the industriousness of the villagers. As the player performs exercises the villagers may build homes, stores, schools, government buildings, castles, landmarks (such as a statue of the player themselves), farms, food silos, parks and play areas, solar panels, windmills, air vehicles, reservoirs and dams, fountains, boats, piers and docks, and even a space station for a rocket launch. In one exercise, a properly performed rep may serve as a countdown proxy for a rocket launch. The villagers may develop electricity or enter a renaissance and create art, music, symphonies, poetry, etc. in response to a patient's exercises.

The changes in the valley are neither entirely automatic nor entirely from the effort of the villagers. In some embodiments, the player will have the opportunity to directly modify the landscape of the valley. They may be able to shape the path of a river, the position of a statue, or level a mountain flat. The player may be able to decorate a living quarter for their virtual selves. As the player progresses in the game and collects currency from completing exercises, they may be able to spend the currency on furniture and decorations within their virtual home. They may be able to even visit or view the homes of other players. The players may also have the option of the type of home(s) they decorate. They could choose from an apartment in city, a mansion in the foothills, a cabin in the woods, or a castle on the hilltop. The home they choose can become their own virtual paradise. The building of the home and its development could be symbolic of the patient's rebuilding of themselves. Alternatively, the player may decorate the homes of the villagers or choose a theme for their neighborhoods, whether the neighborhood be formed of classical Victorian homes, Spanish homes, New England homes, Moroccan homes, etc.

Games

The present invention has developed many games that require traditional physical therapy motions as a core (if not sole) component of the game play. The sensors accurately track the position of the player's body. For example, the sensors detect the precise motion of the arms, such as their height, trajectory, arc, the symmetry between them, and spinal posture (e.g. leans). A novelty with this invention is that the player's hands are left free, as the sensors are worn and not hand-held. Movement feedback is provided in-game and through the tablet.

Patient Setup & Lobby Game

When the player first puts on the HMD, he or she will be immediately greeted with Happy Valley's version of a virtual lobby or waiting room. The lobby is intended to acclimate the player to VR, to entertain them, and to encourage them to explore the 360-degree views in VR. This virtual area keeps the player preoccupied while being fitted with sensors and while the system completes the sensor's auto sync protocol. This area may also be visited between each therapeutic exercise, where it functions as a transition zone between exercises. This area may also be visited at the end of a therapy session, while the player is having sensors removed, where it may offer visual displays indicative of progression. The lobby may change from session to session to show progression, but it always includes a vibrant setting with villagers performing tasks, animals roaming or playing, trees, building projects, and sandbox games to keep the player occupied. The sandbox games may include a follow-and-seek game, a hide-and-seek game, or gaze-and-trigger game.

Figure 12B:
FIGS. 12B-C illustrate targets of the gazing activity, in accordance with some embodiments.
Figure 12C:
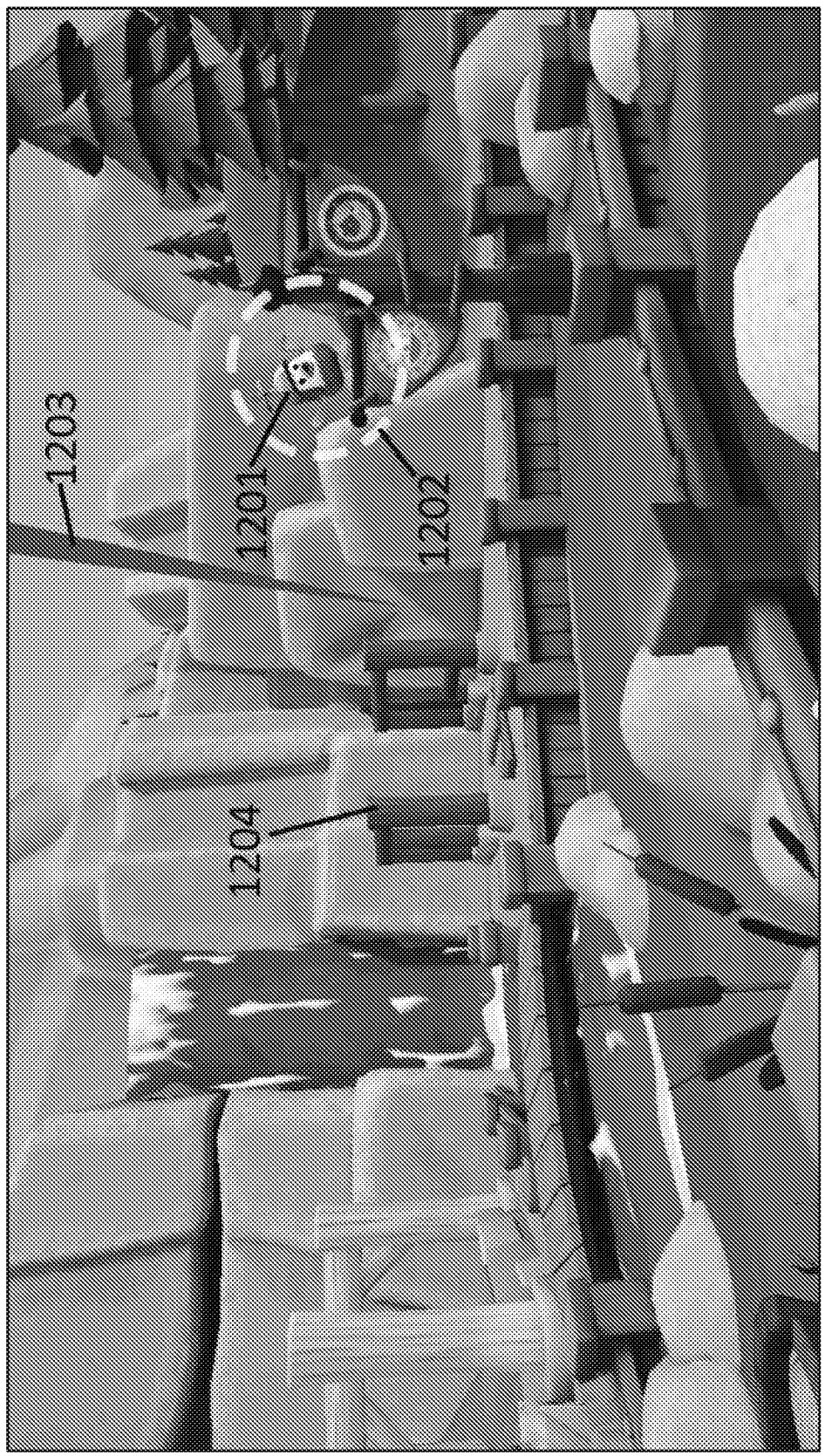

FIG. 12A-12C illustrate a first embodiment of the lobby game, the River. The lobby games include a hide-and-seek game that encourages the player to look for a blue penguin 1201 that appears and reappears at different points in the field of view at varying heights and distances. When the blue penguin first appears in a new location it has an appearing animation, after which it makes body movements, like waving, and makes noises to get the player's attention. If the player does not look at the penguin after a few seconds, it will be circled in a dotted white line 1202 to cause it to further stand out in the VR environment. The player has a visible line or gaze pointer 1203 that points to the center of their view in the 360-degree VR environment and the player uses it to point at the blue penguin 1201. Once the gaze pointer 1203 targets the blue penguin 1201 for a couple seconds, the blue penguin 1201 performs a disappearing animation (such as waving, dancing, jumping, or some other silly action) and then reappears somewhere else in the lobby. The blue penguin 1201 may appear on the ground, in trees, on top of rocks, inside of buildings, on top of buildings, and in other various locations. FIG. 12B illustrates one position that the blue penguin 1201 may appear. This position is about 90-degrees to the left of the player's initial orientation when the game starts. FIG. 12C illustrates a position that is about 30-degrees to the right of the player's initial orientation. The blue penguin 1201 may appear at any angle relative to the player's starting orientation. In one embodiment, hide-and-seek is played while the player is seated and, to fully test a player's cervical spine range of motion (ROM), the penguin may appear directly behind the player, e.g. 180-degrees from the player's initial orientation. FIG. 12C also illustrates a start of construction project 1204. When a specific virtual character is helped or rescued, the next time the player visits the lobby game, that virtual character may be working on the start of the construction project. To see what the finished construction project (not shown) will look like, the player will have to attend the next session of physical therapy. Seeing what the virtual characters were up to will be one of the rewards for continued participation, as discussed later in more detail.

A second lobby game is follow-and-seek. In this game, a bird flies from location to location in the virtual reality environment, and the player is tasked with finding it and tracking it. A player tracks the bird by keeping their gaze pointer locked onto the bird as it flies across their field of view. The bird may fly out of line of sight and reappear at different places in the virtual reality environment. Such tracking provides a good test for determining ROM and the player's degree of fine motor control across his or her neck and spine.

The hide-and-seek and follow-and-seek games are adjustable by a user for range of motion, which affects where the penguin and bird are allowed to appear, for spawn rate and flight speed, and for number of successes required to receive a reward. Players may have limited mobility, and thus a limited ROM, and they may have limited tracking ability. The adjustable nature of these games ensures that even players with limited mobility can succeed. These games may function as a visual field deficit diagnostic tool. Each seek opportunity may be tracked by saving its location and the time it took to successfully gaze upon it. This data is useful in the diagnosis of any visual deficit.

Figure 13A:
FIGS. 13A-13C illustrate various environments for the lobby game, in accordance with some embodiments.
Figure 13B:
Figure 13C:

FIGS. 13A-13C illustrate three additional lobby game settings. FIG. 13A illustrates a Farm lobby. FIG. 13B illustrates a Camping lobby. FIG. 13C illustrates a Lake lobby. These lobbies may host a primary progression mechanic of the overall game. In one embodiment, each time the player completes a therapeutic exercise a mayor of the village provides the player with a stamp on a stamp card. After delivering the stamp card, the player may transition directly to the next exercise or they may first visit a lobby before going on to the next exercise. When in the lobby, the stamp card may be visible to the player, where each collected stamp signifies the completion of a therapeutic exercise, and therefore serves as a direct measure of progress. Additionally, the lobby may provide other indications of progress. Many of the therapeutic exercises revolve around help or saving villagers and animals. These villagers and animals may appear in a lobby after they have been helped or saved. They may grow food, fish, or the like and present their harvest to the player. They also may be seen working on construction projects, such as building docks, lighthouses, clocktower, statues, and other such structures and buildings.

Figure 14A:
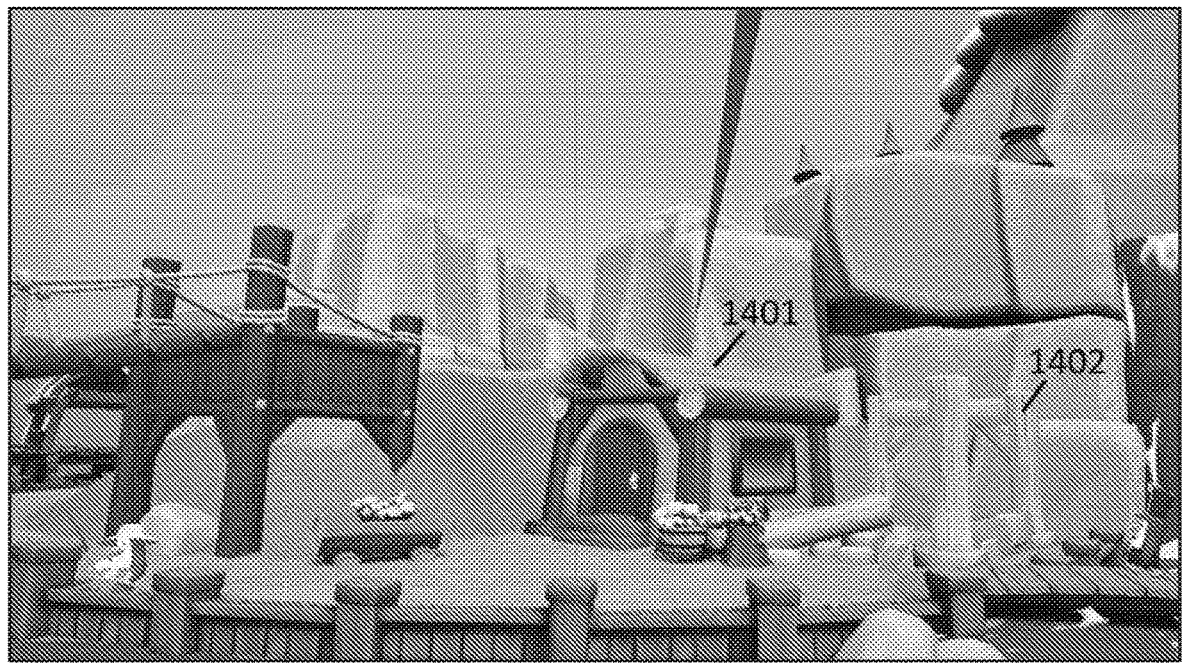
FIGS. 14A-14C illustrate an example progression of the virtual reality environment, in accordance with some embodiments.
Figure 14B:
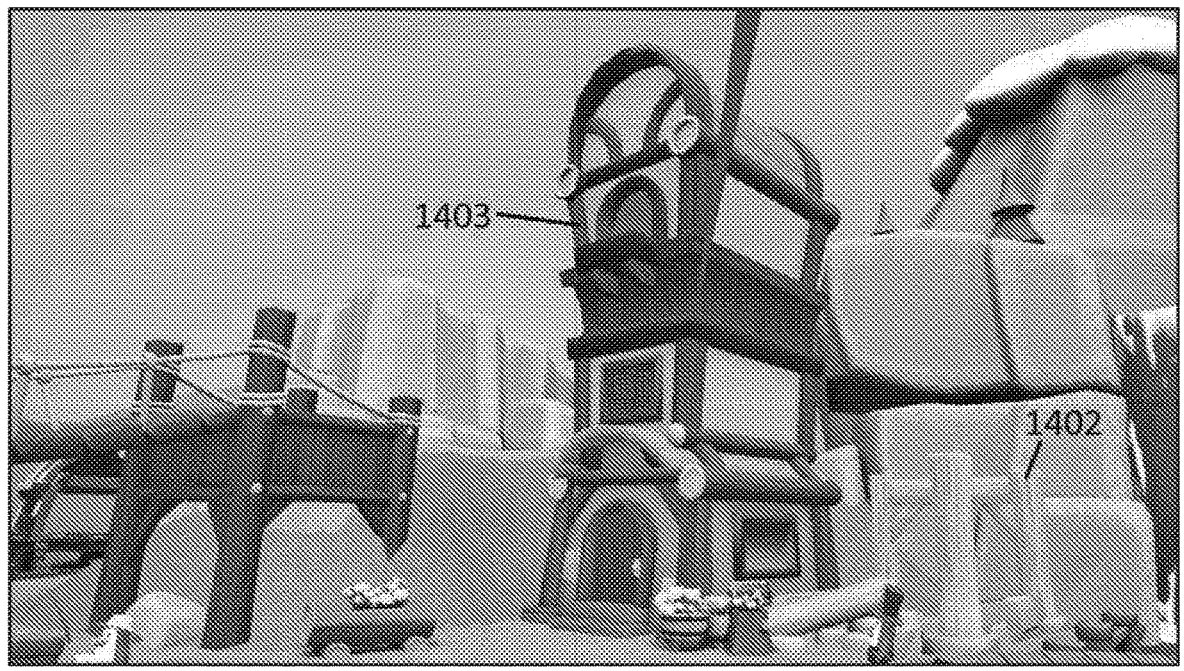
Figure 14C:
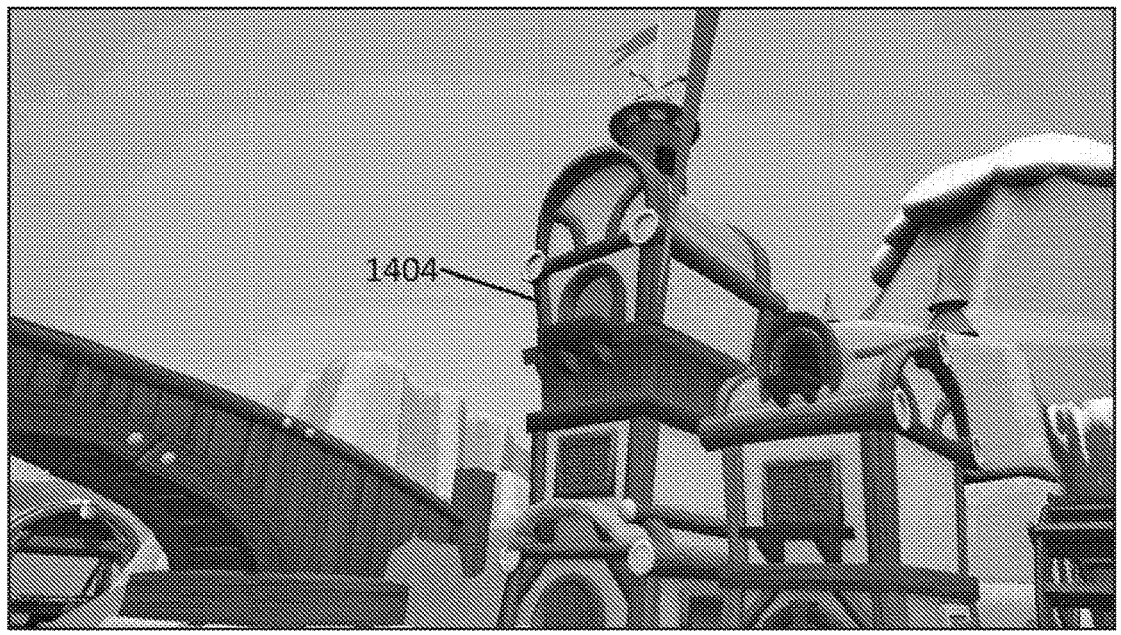

FIGS. 14A-14C illustrate an example construction project a villager may undertake. In one example, the River lobby starts with a small structure 1401 orientated directly in front of the player's initial view on the other side of the river. To the right of the structure is framework 1402 for an expansion of the small structure. When a player helps or recues a villager, they may immediately see that villager in one of the lobbies working on a construction project. For instance, the next time they visit the River lobby, the villager may be working on the small structure 1401 and/or the framework 1402. The goal is to leave the player wondering: What are they doing? What are they building? However, the completed project will not be visible in the lobby until one of the follow up therapy sessions. This will give the player a reason to come to the next therapy session, so they can see what the villagers have been up to. Their continued participation will be rewarded by revealing what the villager had been working on while they were gone. FIG. 14B illustrates an example completed construction project, the tower 1403. Although the player may have immediately seen the villager they helped working on the small structure 1401 and/or the framework 1402, they are not able to see the tower 1403 until they logged in in a following day. In one embodiment, the villager performs an animation, like a grand opening celebration, to showcase their building project to the player. FIG. 14C illustrates a third evolution of the small structure 1401. The small structure 1401 may first be expanded into the tower 1403, and then another villager the player has helped may further expand the structure into a twin tower 1404. These kind of construction projects may occur across several buildings in the lobby game sequentially, simultaneously, or some combination thereof. The gradual increase in industriousness and infrastructure in the lobby games will provide the player with long-term feedback of their progress through physical therapy. As they continue to help and rescue villagers, they will see those villagers giving thanks by building vibrant villages within the Happy Valley.

As the player progresses further and further in the game, the hide-n-seek game will showcase an ever-evolving growth of the villages in the Happy Valley. As they keep playing the game and keep completing therapeutic exercise the lobbies may slowly transform into a vibrant village with all of the villagers the player helped and saved and all of their various construction projects. The villagers will express their thanks and gratitude to the player in many ways, but constructing buildings is a primary method. Additionally, the constructions will provide new places for the blue penguin 1201 to hide and new obstacles for the bird to fly around in the lobby games. In one example, the player first helps or rescues all the villagers necessary to build a village in one lobby. Once that lobby is completed, they may move onto another lobby setting, and start building that one into a village. For instance, the player may start with the river lobby in FIG. 12A. Once that is built into a village, they may transfer to the farming lobby in FIG. 13A, then the camping lobby, and then the lake lobby. This will give the player fresh experiences and plenty to accomplish in order to encourage continued participation.

Sunrise Arm Raise

Figure 15:
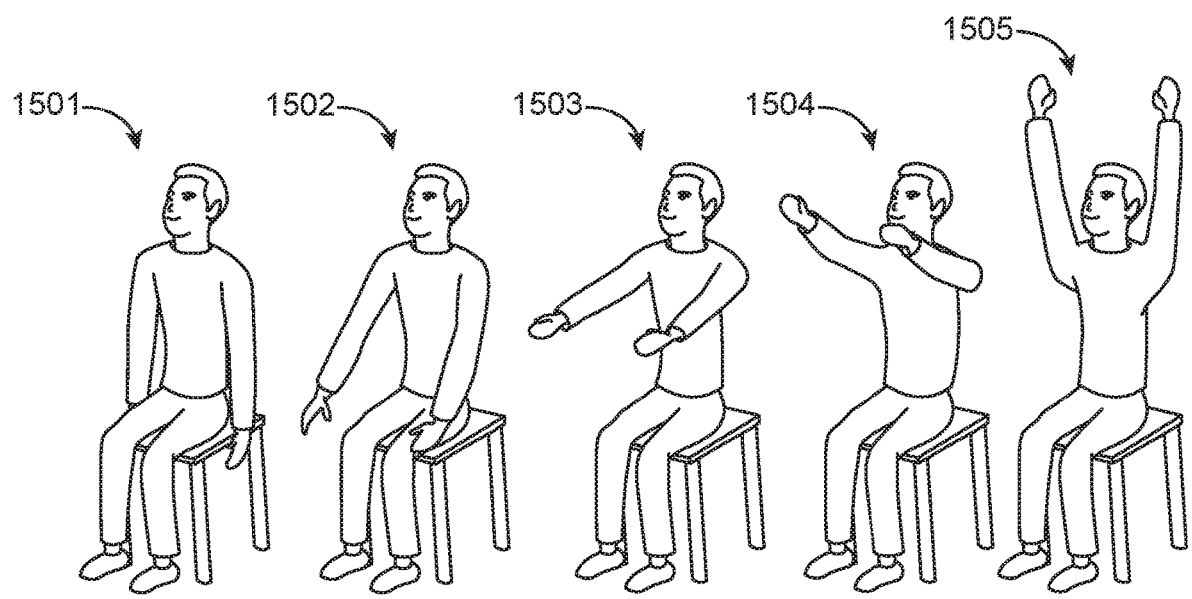
FIG. 15 illustrates an example repetition of an arm raise therapeutic exercise.

A first group of therapy games are modeled after a traditional stroke therapy exercise called a cane raise. The cane raise is a seated exercise, where a cane is held with hands about shoulder width apart. The cane is raised from the lap to an overhead position. Stroke victims often have a weak side. By grasping onto the cane, their strong side can assist their weak side during the arm raise. FIG. 15 illustrates how a person's arms move when performing a cane raise exercise. The start position for the exercise is with arms hanging downwards in a relaxed position 1501. The arms are then raised slightly to an initiation position 1502. The arms are then raised to a straight-out position 1503. The arms are then raised to an upward position 1504. The arms are then raised vertically 1505. The motion is then reversed back to the relaxed position 1501 to complete a single, full repetition. The motion is ideally performed as a smooth arc with both arms being symmetrical during the movement, e.g. same height and extension at the same times.

Figure 16A:
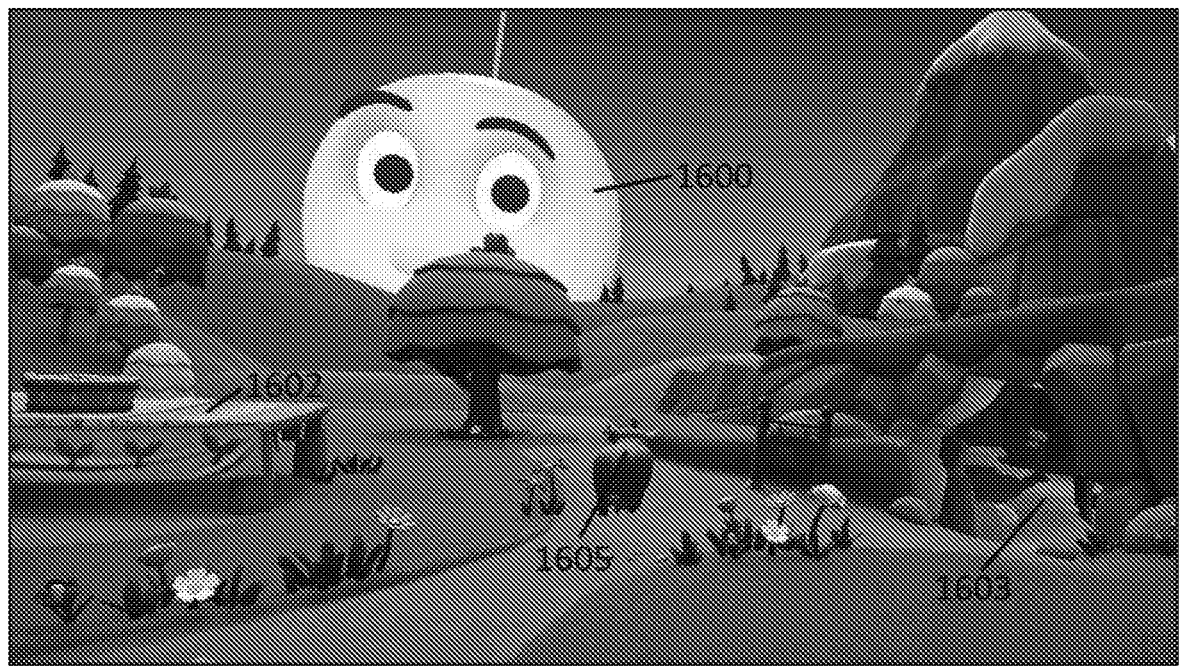
FIGS. 16A-16B illustrate a sandbox sunrise activity, in accordance with some embodiments.
Figure 16B:
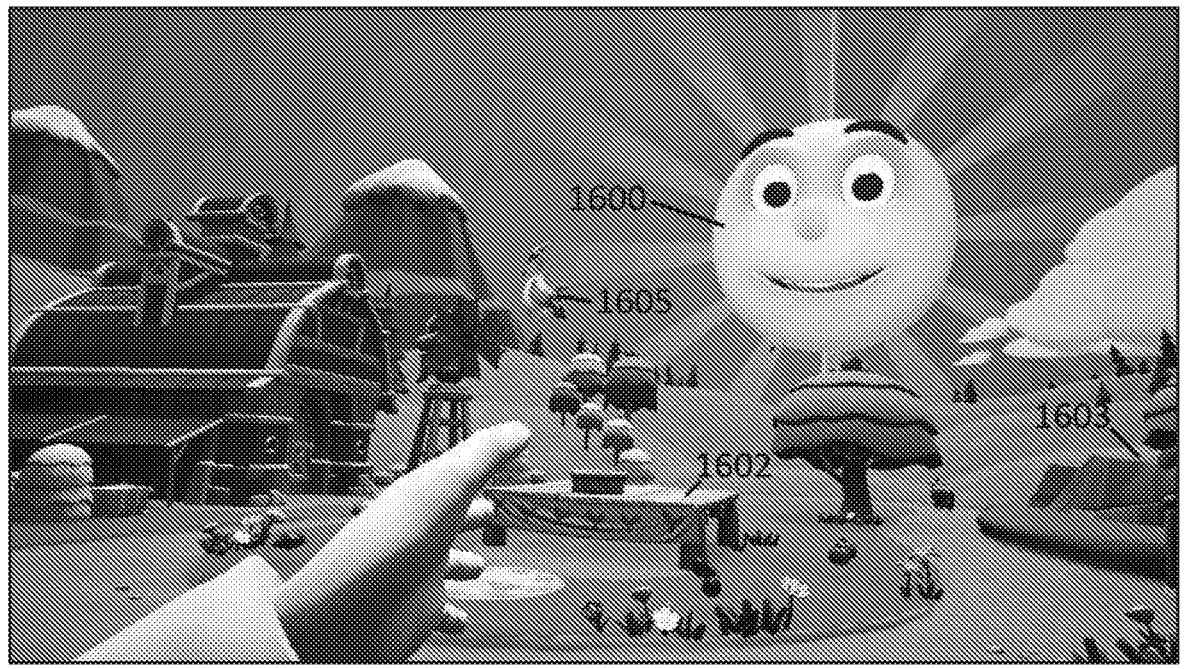

FIGS. 16A-16B illustrate a VR version of the cane raise. In this example, the players can perform the motions of the cane raise activity and move the sun itself 1600. In a first embodiment of the sunrise therapeutic exercise, the game is a sandbox game with no objective or win condition that is designed to get the player to understand the sunrise game mechanic. The player is seated overlooking a valley with farmlands, a raised stage 1602, an ice cave 1603, villagers 1604, animals 1605, such as birds flying overhead and a characteristic cow, Betsie, and other fantastical things. At first the valley is in darkness, but when the player raises their hands a sun 1600 will rise over the horizon washing the valley with a brilliant light. The sun includes a face, and it rises over the horizon with an expression of joy. Typically, the sun reaches its zenith when the player's hands are raised directly over their head. However, if a player cannot reach that high, the games settings may be adjusted so that the sun reaches its zenith at a lower arm height. When the player lowers their arms, the sun 1600 will set, and the valley will be cast into darkness. The player may perform the arm raise as many times as they please in this embodiment. The sunrise games test a player's shoulder flexion as reflected in the ability to raise his or her arms. This sandbox version also allows the user or practitioner to augment the game with therapeutic equipment, such as resistance bands, weights, etc.

Bumper Crop

Figure 16C:
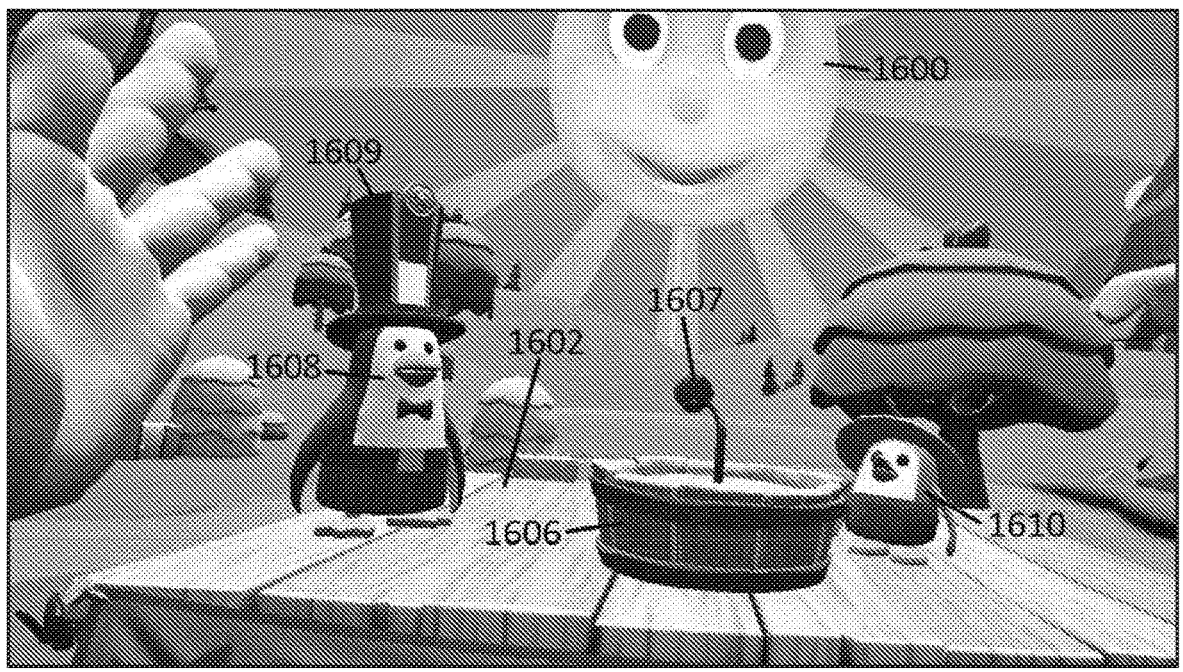
FIGS. 16C-16E illustrate a growing sunrise activity, in accordance with some embodiments.
Figure 16D:
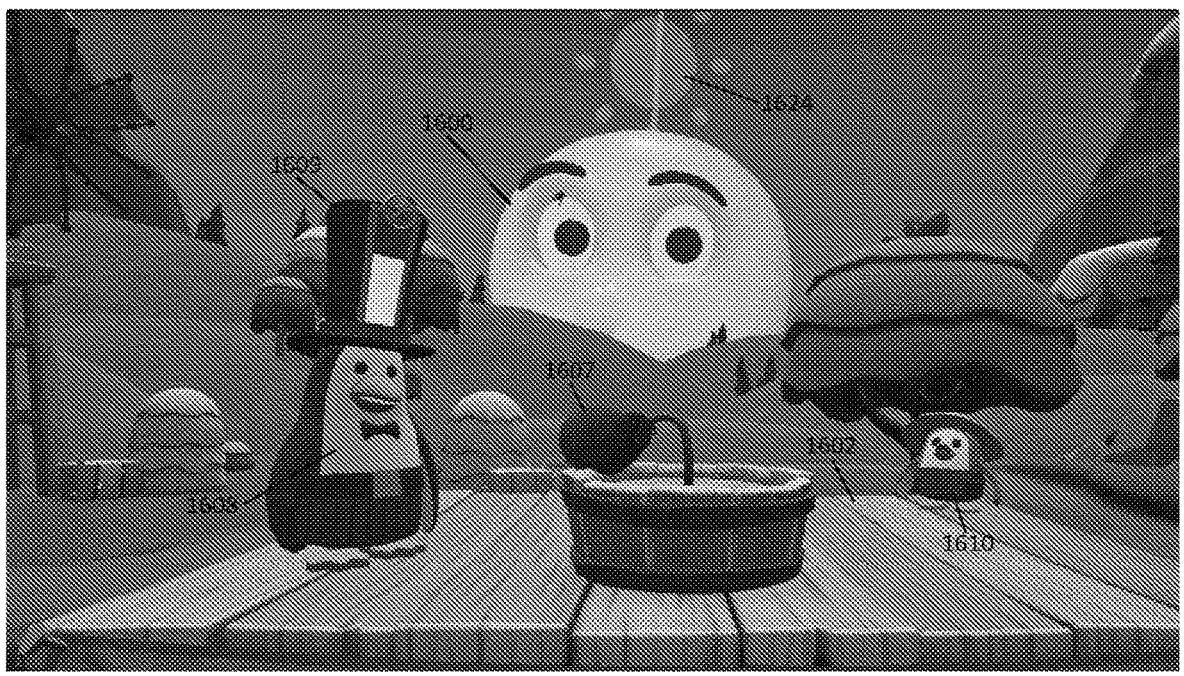
Figure 16E:
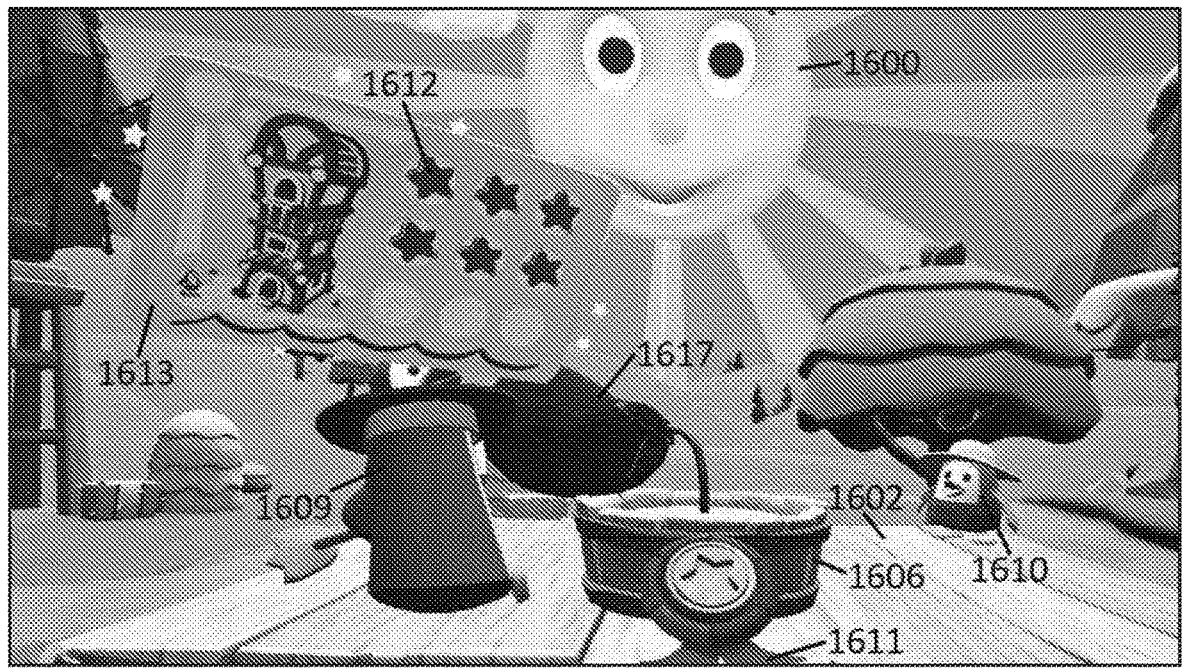

FIGS. 16C-16E illustrates a second embodiment of the sunrise therapeutic exercise. In this embodiment, the player will be transported adjacent to the raised stage 1602. The stage will have a bucket 1606 housing a small sapling 1607, a mayor penguin 1608 with a top hat 1609, and a young blue penguin 1610 may be present on the stage as well. In this version, when the player raises their hands, the sun will rise, and the sapling 1607 will grow. In this illustrated example, the player is growing an eggplant. At first the blue penguin 1610 may appear sad, but when the player completes an arm raise repetition (rep), the sapling 1607 will grow larger and the blue penguin 1610 will express happiness and wonder. The user may adjust the game to tailor specifically how many reps it takes for the sampling 1607 to reach its full-size form 1617. What constitutes a full rep is also adjustable, i.e. how high the arms must be raised each time. Typically, a dull white sun 1624 marks the spot in the sky that is considered the sun's zenith, and this may function as a target for the player. Once the sapling 1607 reaches its full size, the mayor penguin 1608 may present the player with a blue ribbon 1611 and provide the player with a stamp 1612 on their stamp card 1613. The villagers will typically be celebrating during the presentation of the stamp card 1613 to provide encouragement to the player. Each time the player completes a therapeutic exercise, they may be presented with this stamp card 1613, which signifies how many exercises they have completed. Each time this game is played a different vegetable may grow, such as a pumpkin, a carrot, cabbage, eggplant, or other similar fruit or vegetable. This food helps feed the village and may appear in the lobby games.

Ice Cave

Figure 16F:
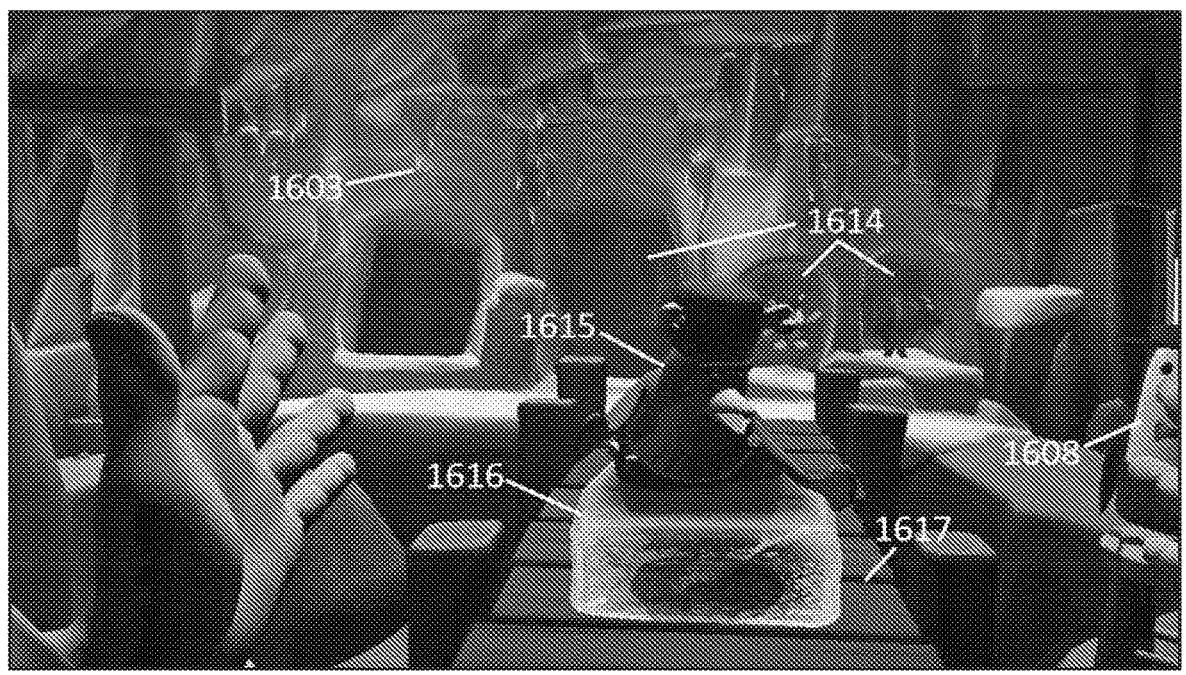
FIG. 16F illustrates a melting sunrise activity, in accordance with some embodiments.

FIG. 16F illustrates a third embodiment of the sunrise therapeutic exercise. In this embodiment, the player will be transported to the ice cave 1603. The player will be in the center of the ice cave 1603, to their right a family of villagers 1614 can be seen frozen in ice, and a villager 1615 is frozen in a block of ice 1616 on a stage 1617 directly in front of the player. This villager 1615 has been chiseled free from the walls of the ice cave and is positioned next to the mayor penguin 1608. When the player raises their arms, the sun 1600 will rise and its light will wash through a hole in the roof of the cave, casting light on the villager 1615 trapped in ice. With each repetition, the ice block 1616 will melt. As the ice block 1616 melts, the trapped villager 1615 will begin wiggling the body parts that are freed, and other villagers in the cave may begin cheering on the player for rescuing their friend. Once the villager 1615 is completely free, the villagers will celebrate, the mayor penguin 1608 may perform a celebratory flourish of the top hat 1609, and present the player with their stamp card 1613, which the mayor 1608 may promptly add an additional stamp 1612 to. Each time the player enters the ice cave they may free a different member of the family, such as the mom, dad, kid, and pet boar.

Many Farms

In a fourth embodiment, the sunrise therapeutic exercise will be associated with a number of farming plots. As the player raises the sun, the on or more plots will transition from barren (empty, just dirt), to a series of ever larger vegetable plants. At first, there will be sprouting vegetables, then small vegetables, then medium vegetables, and lastly large vegetables. There is an animation "pop" each time the vegetables grow bigger. Villagers will actively visit the plots to spread seed, to water, to harvest, to eat, and to admire and celebrate new growth. When a plot is full of large vegetables, a villager will come and harvest each plant individually and collect the harvest in a container. Sometimes when a villager harvests a vegetable, they may pull up a "weird" version of the vegetable, such as a strangely deformed vegetable or one being currently eaten by a rodent, etc. These will be charming & funny moments. After the fields have been filled with food, the mayor penguin 1608 may add one or more stamps 1612 to the player's stamp card 1613.

Long-term feedback of the sunrise may be offered by a farm stand. The stand is either empty, full, or somewhere between. Depending on exercise consistency and the amount of exercises completed the farm stand will fill accordingly. Additionally, villagers may be seen walking around with a harvested vegetable. The villagers may also be seen eating the grown vegetables throughout happy valley. The stand may be visible in the lobby areas.

Sunrise Feedback, General Feedback, & VR Tricks

The present invention's adjustable difficulty facilitates short-term and long-term feedback in-game. Difficulty is adjustable by a simple sliding bar or by giving an example of an expected motion and setting that as the "full rep." These controls ensure that even severely inhibited players with limited motion still can complete successful reps. This dynamic difficulty will ensure that the patient doesn't feel like they are failing and/or hopeless from the start. They will be able to play the game, and the sun will raise and stay level with small movements and limited synchronization between the players arms.

In one embodiment of the cane raise exercise, a player performs a perfect rep when they raise their arms from their sides to over their head over two seconds, and then lowers their arms back to their sides over two seconds while keeping the arms perfectly symmetrical and with no torso lean. However, the sunrise therapeutic exercise, like all other exercise games of the present invention, are at least partially adjustable to change the difficulty of the exercise. By lowering the difficulty, the player can perform a suboptimal rep and the game will treat it as a perfect rep.

During physical therapy, the practitioner is the ultimate arbiter of quality. Physical therapy is very personal. Progress and success vary widely not only from player to player, but from a player's good day to a bad day and from the start of an exercise to the last rep. A player may come in sore and tired one day, and they may be sore and tired by the end of their therapy session. What is important is participation and effort. A perfect rep for a player is one where they put in the amount of effort the practitioner thinks will best facilitate rehabilitation. Additionally, exercises may be very unstructured, and what constitutes a "rep" may vary drastically. The games of the present invention offer sandbox modes, where the user can set what a rep looks like by having the patient perform a motion. The game will then treat that motion as a rep for whatever game the player is in and reward the player accordingly for successful reps.

In the sunrise therapeutic games, the face of the sun 1600 may respond to several variabilities in movement, such as speed, height, and balance. The speed with which the arms are raised and the degree of synchronization between the two arms, e.g. how level are the arms with one another. Regardless of the player's movement, the sun 1600 will remain positive and enthusiastic. However, with too little or too much speed the sun's face will be slightly less exuberant. With tilts, the sun's face will tilt and thereby provide near real time form feedback. The game offers little if any negative feedback. Rather, the game will be humorous, charming, or funny for "poor form." In other words, the game will bias towards positivity and encouragement. The sun 1600 will also provide visual indications of the height that the player's arms reach. At the start of the rep, the sun 1600 is behind the horizon, with a small arm raise the sun 1600 peaks over the horizon, at a medium arm raise the sun

1600 starts to shine brighter and its smile widens, at the top of the arm raise the sun 1600 shines its brightest and its smile is at its widest. When a user adjusts the difficulty of the sun level to be easier, for example, the sun 1600 will have a bigger smile and raise higher for smaller arm raises. If the therapist sets another motion as the rep necessary to raise the sun 1600, then completion of that "rep" will cause the sun 1600 to traverse from behind the horizon to its zenith. How high the sun needs to be raised may be depicted as a dull white sun 1624 in the sky, as depicted in FIG. 16D. The dull white sun 1624 can be thought of as a target for the sun 1600. When the sun 1600 is centered over the dull white sun 1624, the rep has been completed and the sun 1600 is depicted as if at its zenith.

Mirror and Gravity Protocols

The present invention uses virtual reality to not only provide motivation and visuals indicative of immediate form feedback, but also uses VR to generate an avatar of the player. Typically, the avatar makes whatever movements the player makes when he or she makes them. However, sometimes the avatars movements do not directly correspond to the movements of the player. For instance, a displayed motion of the avatar may be different from a real-world motion, and a difference between the displayed motion and the real-world motion may be varied to induce the user to perform the therapeutic activity. In this way, virtual reality environment of the present invention is exploited to its full potential to trick the brain into believing it can accomplish more, which benefits the restoration of neuroplasticity.

FIG. 17 illustrates one embodiment of the present invention, where the avatar that is animated for the player does not directly map to the player's movements. In a first example, a player 1701 is performing an arm raising exercise. The player's right arm 1704 is weaker than their left arm 1705, so when the player 1701 tries to raise both arms in sync, the right arm 1704 can't keep up. During the sunrise activity, the sun's face may provide visual indications that the player's arms are uneven, such as by taking on a tilt that mirrors the player's uneven arms. When a player's arms are raised unevenly, it may be helpful to activate a midline mirror protocol. When the mirror protocol is activated the player 1701 may have arms raised at different heights, but the avatar 1702 will show arms at the height of the strong arm. In other words, the mid-line mirror protocol measures movements of a first side of a player and displays those movements on a first side of the avatar and a mirror of those movements on a second side of the avatar. If used during a sunrise activity, the sun will not tip, but be balanced like the arms of the avatar. By having the avatar show the weak arm higher than the player's actual arm, the VR system may be able to trick the player's brain into believing it can do it. The visual system will see what is supposed to happen when the patient triggers the neurons they are firing during the exercise. It will provide a link between what the patient desires to happen and what should be happening.

FIG. 17 illustrates another example where the avatar that is animated for the player does not match the player's movements. In this second example, the player 1703 may have their arms raised, partially raised, unevenly raised, or just hanging by their sides. When the anti-gravity protocol is activated, no matter where the player's arms are actually at, the avatar 1702 will display the arms as floating evenly into the air. In other words, the anti-gravity protocol causes the arms and hands of the avatar 1702 to float upwards as if at least a portion of the avatar 1702 was not restrained by gravity. This may give the player 1703 a sense of weightlessness that can cause the player 1703 to raise their arms in real life in a subliminal, non-intentional manner even when trying to raise their arms through volitional instruction fails.

Hot Air Balloon

Figure 18:
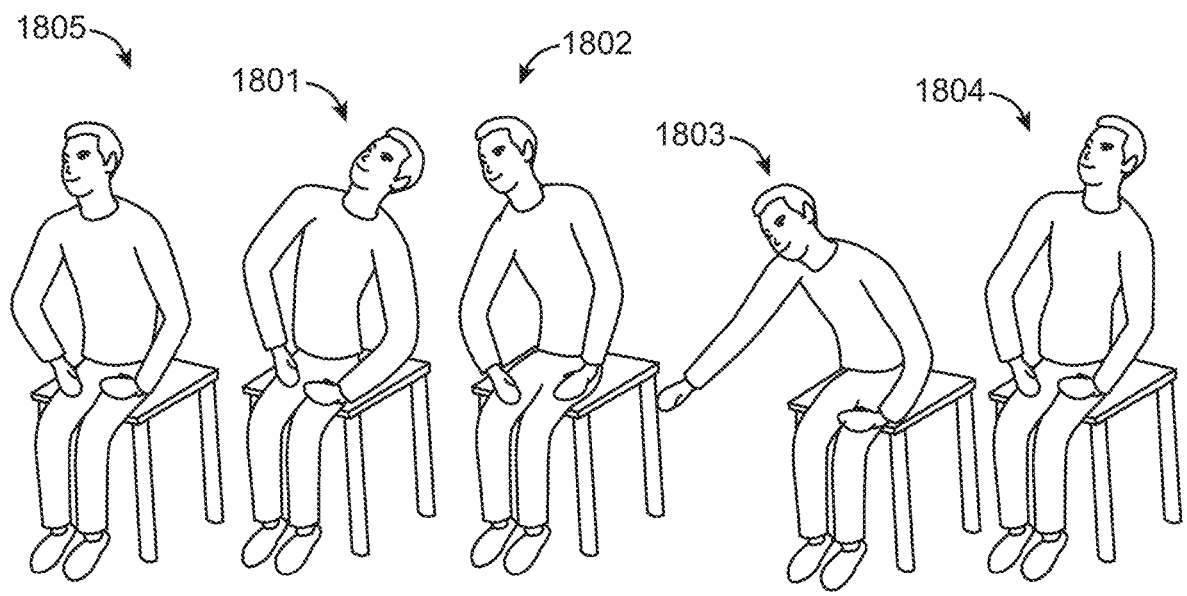
FIG. 18 illustrates example movements of a leaning therapeutic exercise, in accordance with some embodiments.

The present invention may include several variations of a hot air balloon therapeutic exercise. FIG. 18 illustrates the movements a player may be encouraged to make during a hot air balloon activity. The performance of the activities typically requires, measures, and tests lateral trunk flexion 1801, 1802, seated trunk extension 1803, back extensor flexion 1804, trunk circles, or some combination of such movements relative to an upright posture 1805. When the player is loaded into a hot air balloon therapeutic exercise, they will typically find that their torso leans cause a penguin in a hot air balloon to mimic those same leans. The penguin may be wearing a hat that spews fire into the open bottom of the balloon, filling it with hot air. As the penguin leans from side to side and forward and back, the fire from the hat directs the movement of the hot air balloon. In an alternative embodiment, a penguin pilot mirrors the leans and bends of the player and the penguin pilot guides the hot air balloon in the direction of the leans and bends. In further alternative embodiment, a player's torso movements cause wind to blow in the direction of the lean, which causes the hot air balloon to move. The wind generated by the player's movements may causes other aspects of the village to come to life. For instance, the wind may spin a windmill and bring electricity and other benefits to the village, or the wind may simply blow some unsuspecting birds out of a tree.

Balloon Pilot

Figure 19A:
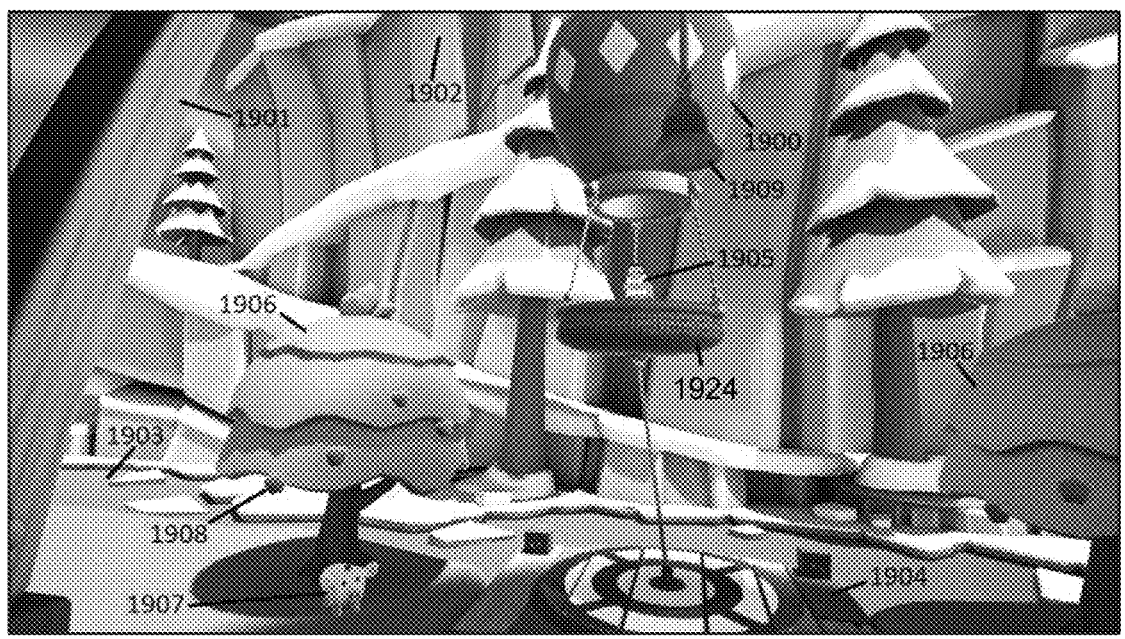
FIG. 19A illustrates a sandbox hot air balloon activity, in accordance with some embodiments.

FIG. 19A illustrates a first embodiment of a hot air balloon therapeutic exercise. Here, the player is presented with a sandbox activity and finds themselves seated under a cabin awning 1901 that overlooks a massive mountain 1902, with mountaineers climbing up, a melting icepack that feeds into a river 1903, and a waterfall coming off the mountain. Directly in front of the cabin is a hot air balloon 1900 tethered to a platform 1904, with a penguin pilot 1905 sitting in the basket 1924. On either side of the hot air balloon 1900 are apples trees 1906, and one has a pig 1907 beneath it laying in the shade. When the player leans towards an apple tree 1906, the penguin pilot may mirror the lean of the player and cause the hot air balloon to advance towards the apple tree 1906. When the hot air balloon 1900 collides with the apple tree 1906, apples 1908 will fall off of it, and the pig 1907 will go around and eat them. As the pig 1907 eats the apples 1908, it will become larger, and eventually it will eat so much it falls asleep. When it wakes up, it may revert to its normal size again. In addition to the apple trees 1906, the hot air balloon 1900 may also be able to run into bells 1909 hanging above the apple trees 1906. They may be orientated in a triangle, and by performing a smooth torso rotation, the player may be able to cause the hot air balloon 1900 to collide with all three in sequence and make a melodic tune. Being a sandbox game, this version of the hot air balloon therapeutic exercise has no direct objective that needs to be completed to win or complete the level.

Balloon Rescue

Figure 19B:
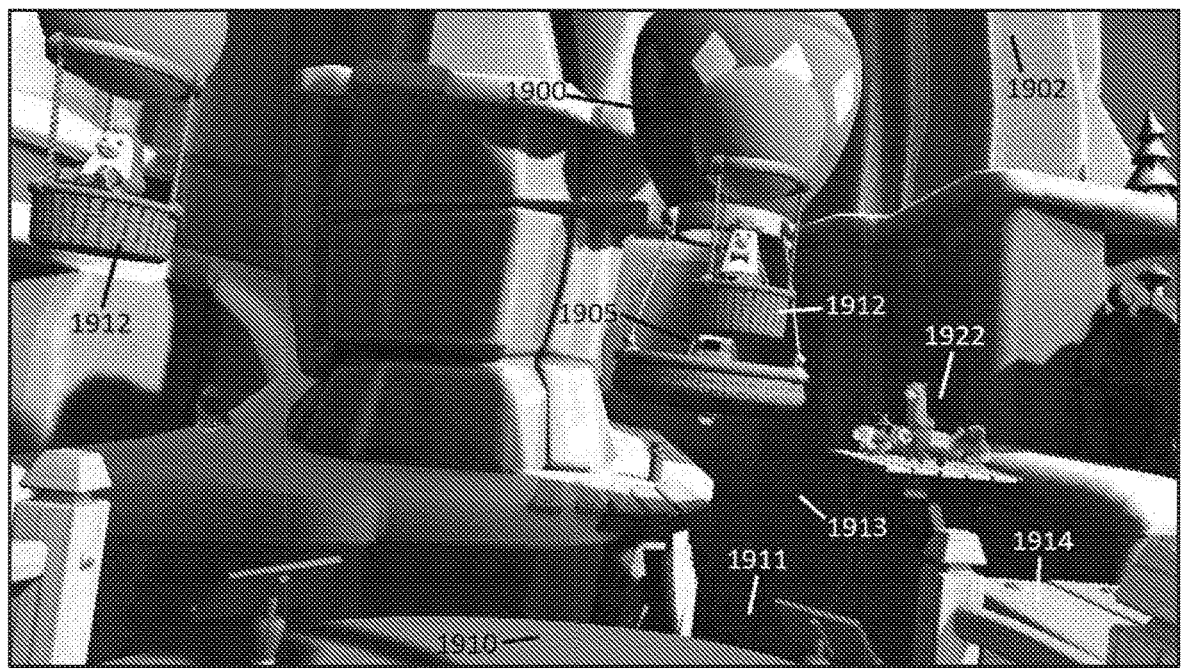
FIGS. 19B-19D illustrate a rescue hot air balloon activity, in accordance with some embodiments.
Figure 19C:
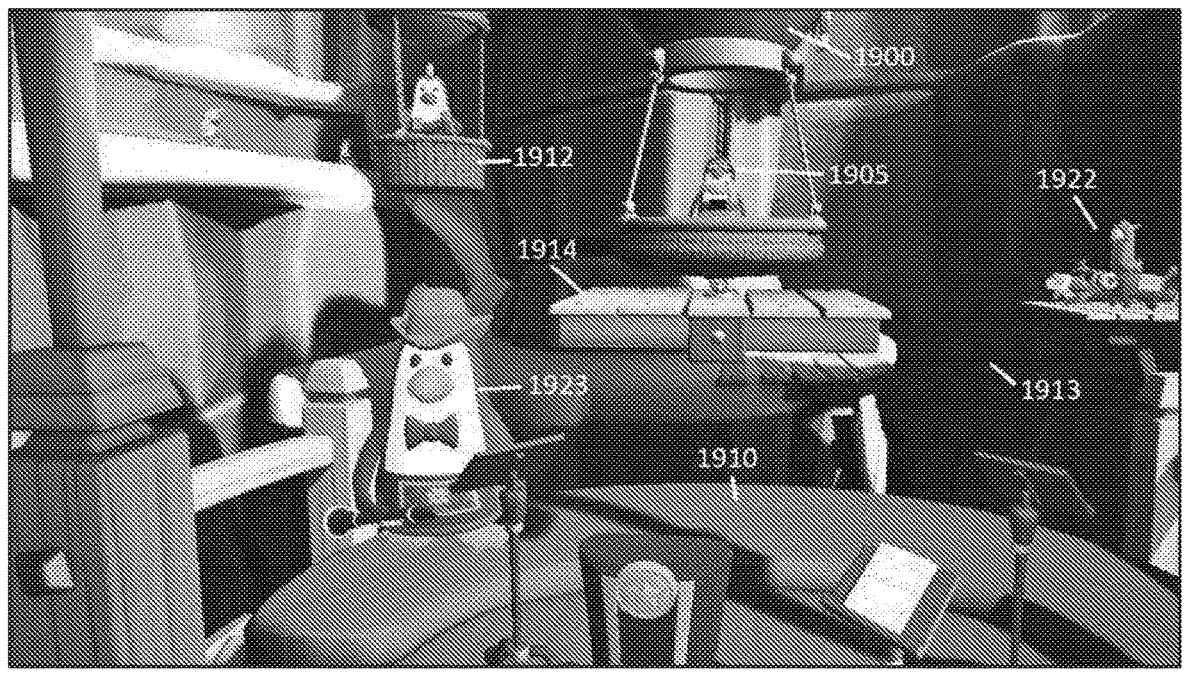
Figure 19D:
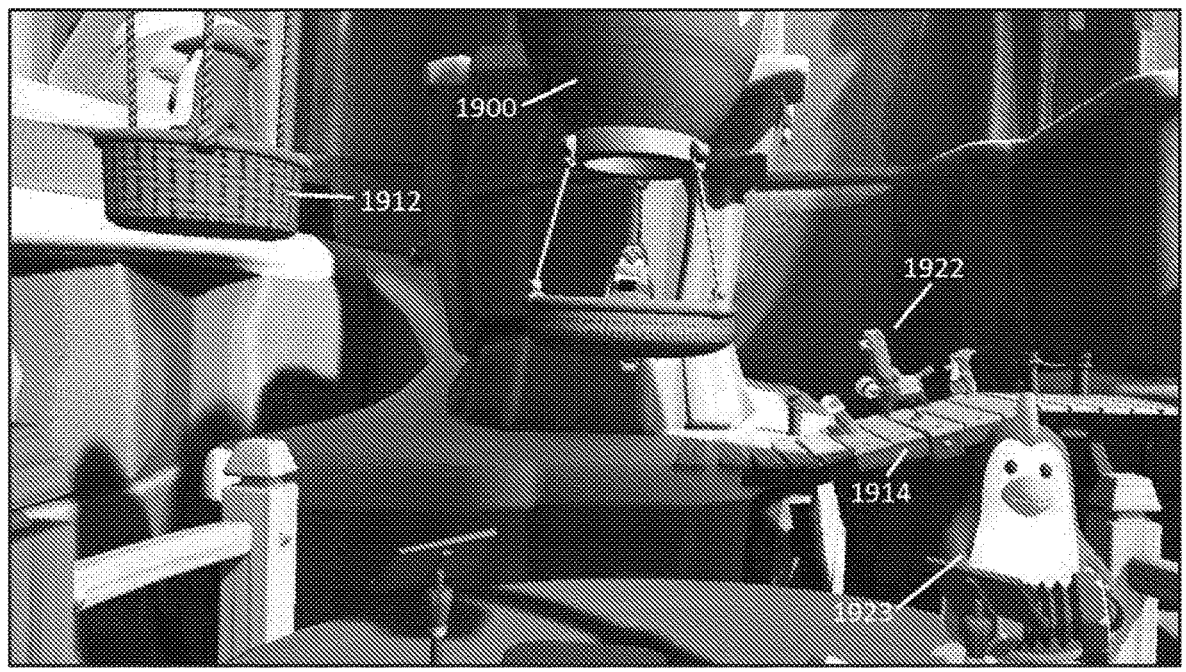

FIGS. 19B-19D illustrate a second embodiment of a hot air balloon therapeutic exercise. Here, the player is transported onto the massive mountain 1902. The player finds themselves on a stage 1910 with a lonely composer, and the stage 1910 overlooks a large canyon 1911 with additional mountains on the other side. Stranded in the air above the canyon are several run away hot air balloons 1912, each having a member of the composer's band stranded in them. The player is tasked with rescuing the band members by using his or her own hot air balloon 1900 to knock into their balloons so that they are guided to the safety of the stage. Once guided to the stage 1910, rescued penguins 1923 jump out and may start performing music on the stage 1910. The player can rescue a bass player, a concertina (accordion) player, a clarinet player, and other various types of band members. The player's hot air balloon 1900 contains the pilot penguin 1905 that mirrors the movements of the player and may also include the mayor penguin 1608. The difficulty of this game may reduce the number of band members that must be rescued and may make the balloons easier to bump into so that their trajectory is directed towards the composer's stage. After the player rescues all of the stranded musicians, the player will be rewarded with a symphony by all the band members. If the player looks across the canyon, they may see a cabin with a penguin enjoying the company of its alpaca. Additionally, the player may see a group of mountaineers 1922 unable to traverse a large ravine 1913 along their mountain path. The player may control their hot air balloon 1900 to go and pick up a bridge 1914, and then with leans and twists they can properly orientate and position the bridge 1914 so the mountaineers 1922 can safely cross the ravine 1913 and continue their journey to the top of the mountain 1902. Once the player has recued the band members, and optionally delivered the bridge 1914, the mayor penguin 1608 will present the player's stamp card 1613 with a flourish of his top hat 1609 and provide the player with at least one new stamp 1612 to mark the player's therapeutic progress.

Balloon Summit

Figure 20A:
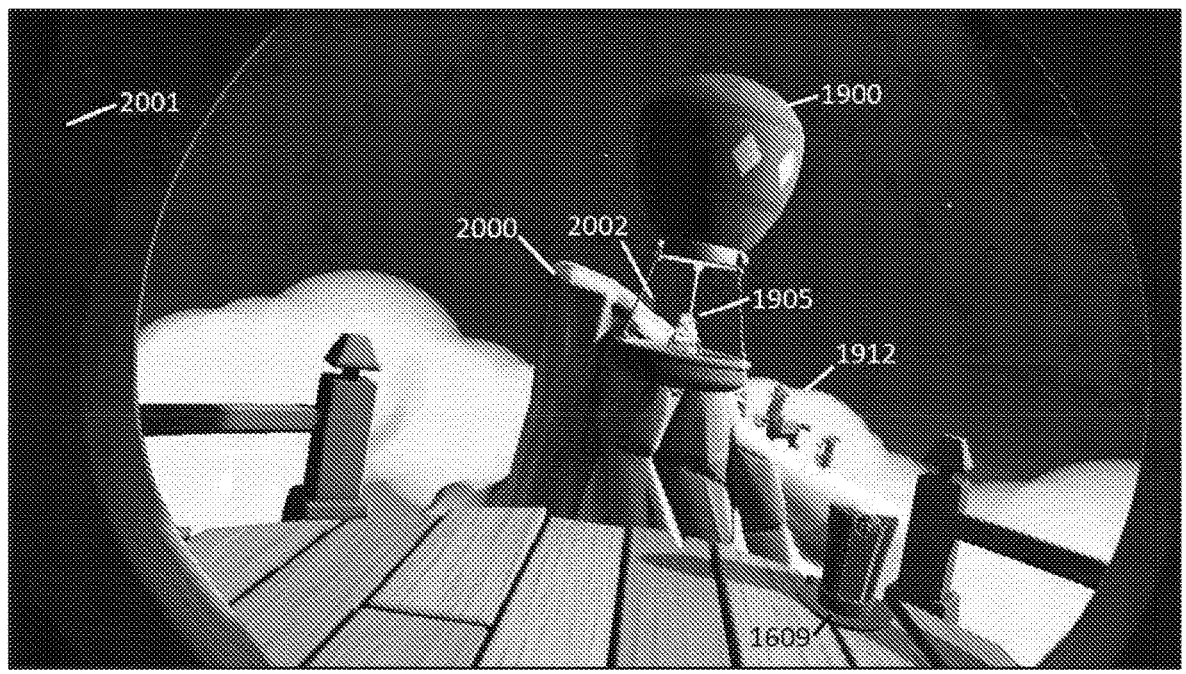
FIGS. 20A-20G illustrate a summit hot air balloon activity, in accordance with some embodiments.
Figure 20B:
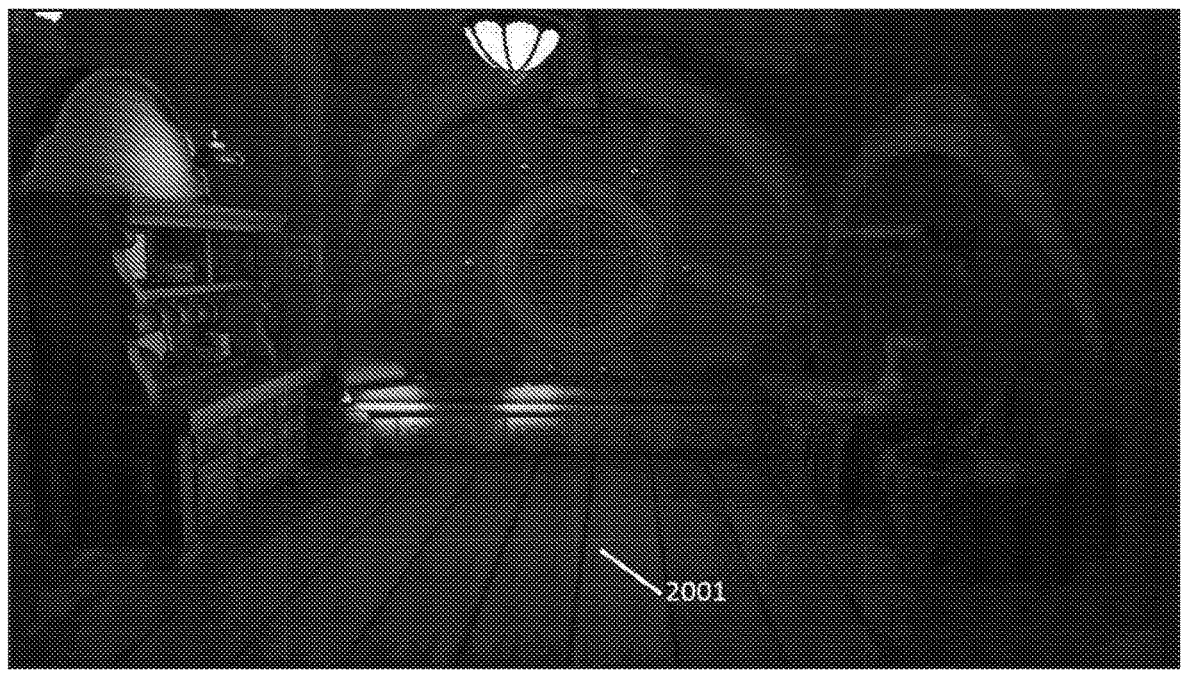
Figure 20C:
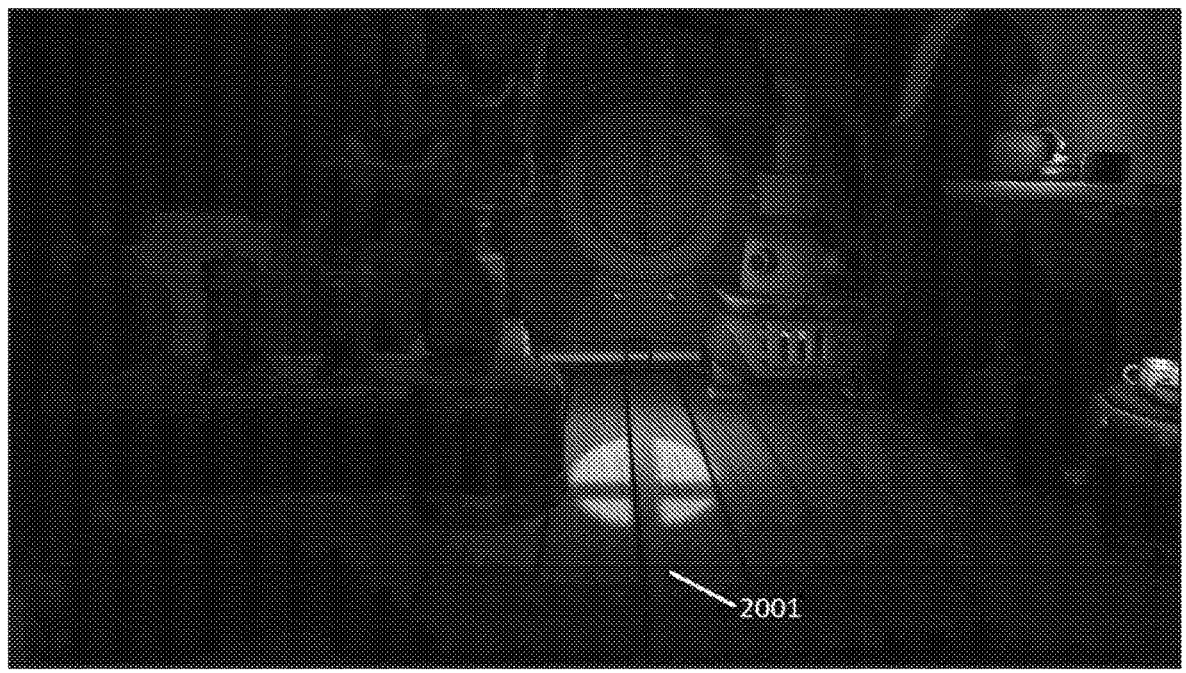
Figure 20D:
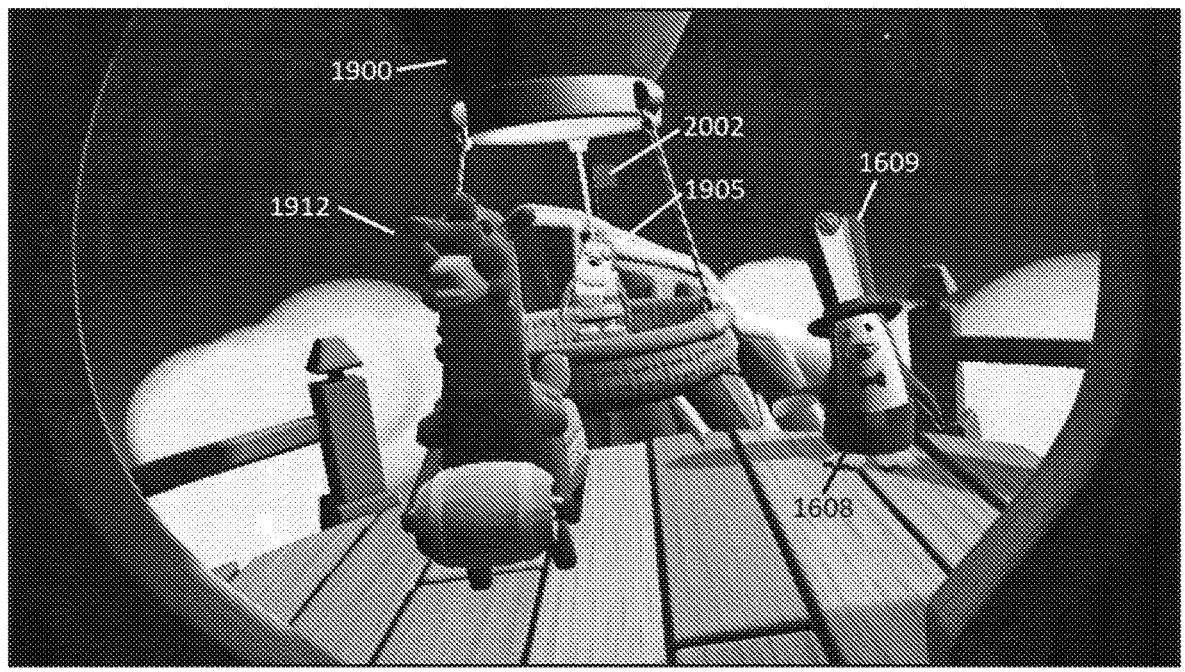
Figure 20E:
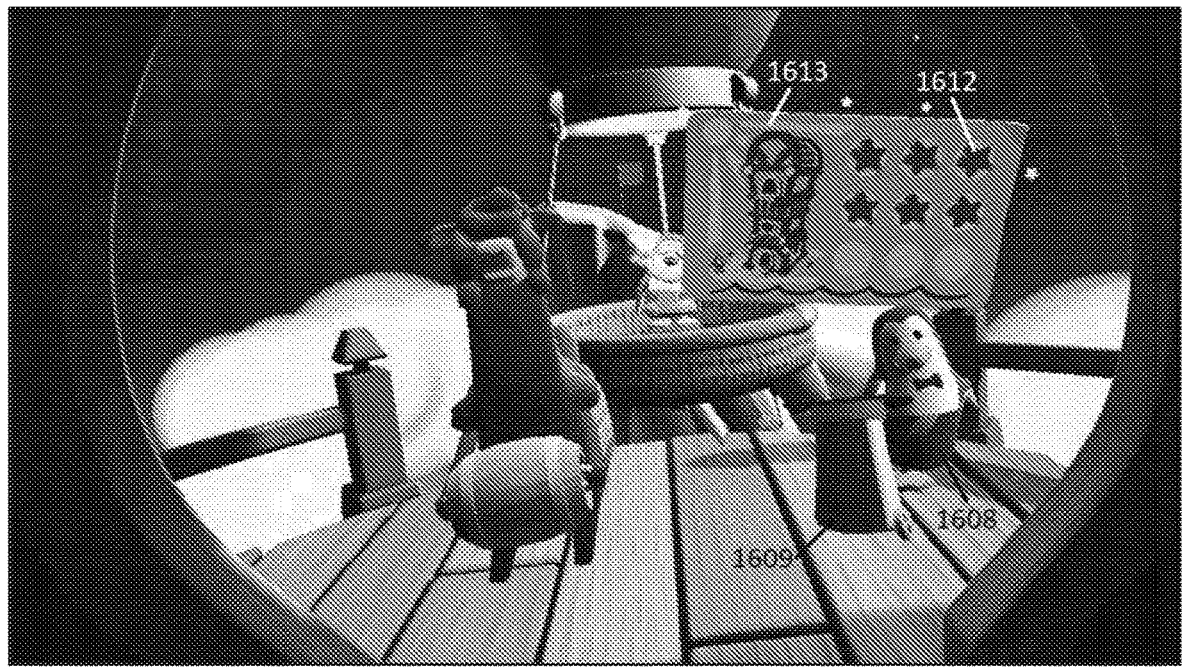
Figure 20F:
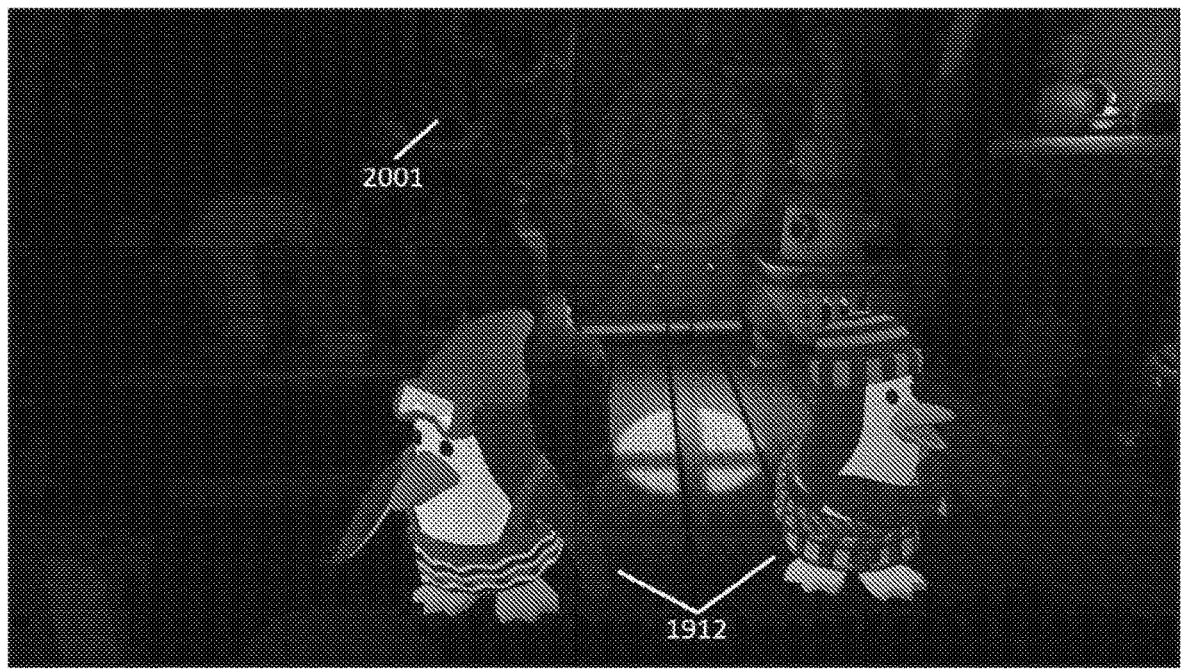
Figure 20G:
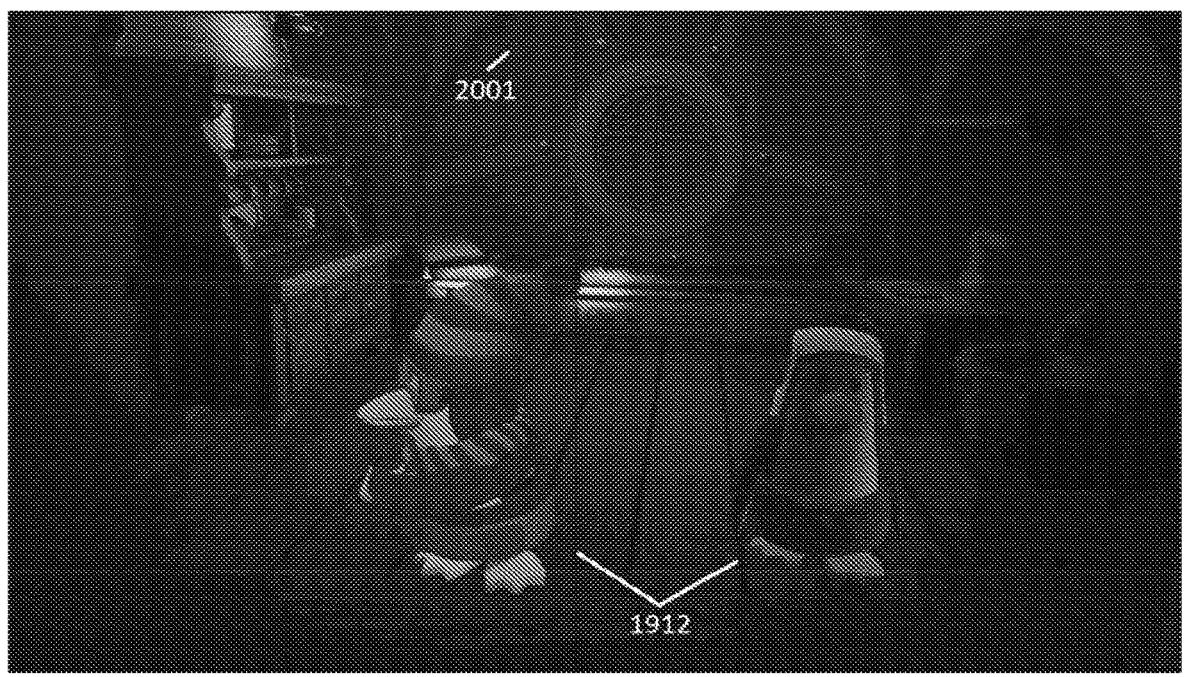

FIGS. 20A-20G illustrate a third embodiment of a hot air balloon therapeutic exercise. Here, the player is transported to a peak of the mountain 1902. The player finds themselves in a floating mountaintop chalet 2001. Hanging in front of them is the hot air balloon 1900 with the penguin pilot 1905 onboard and the mayor penguin 1608 may join the penguin pilot 1905 in the basket. Across a large gap, the mountaineers 1912 are stuck on another mountain peak 2000 in the distance and need the player's help. The mountaineers may raise a summit flag 2002 and sound a horn signaling the need for rescue. The horn may also signal the start of the game. Between the player and the stranded mountaineers 1922 are high winds and clouds. The player is tasked with rescuing the mountaineers 1922 one by one by piloting the hot air balloon 1900 from the chalet 2001, to the peak 2000, and back. The clouds act as moving obstacles that block the hot air balloon 1900 and push it out of the way. The game's difficulty is adjusted by changing how many clouds serve as obstacles, how fast they move, and how much influence they have over the hot air balloon 1900. If the player looks around in the mountain top chalet 2001 at the start of the game, they will notice that it is empty, as depicted in FIGS. 20B and 20C. After the player rescues mountaineers, they will enter the mountaintop chalet 2001 to warm up, as depicted in FIGS. 20F and 20G. Once the player rescues everyone, the mayor penguin 1608 may appear from under its top hat 1609 to unveil the player's stamp card 1613 and place a new stamp 1612 on it.

Balloon Field

In a fourth embodiment of a hot air balloon therapeutic exercise, the player finds themselves standing on a platform overlooking a field with a hot air balloon floating 1900 over it. The player may be presented with rings on the ground and be tasked with aligning the rings with a shadow of the hot air balloon 1900 by performing leans and bends. There may be multiple rings that must be shaded in a particular sequence or the rings may move when shaded, wherein the player must track the rings. Alternatively, the field is filled with dry farm land and the player is tasked with watering the field by tracing over the fields with the hot air balloon. In this version, the shadow underneath the balloon will correspond with a focal point for water that is dispersed from the hot air balloon 1900. As the player waters the farmlands, they will start to grow and flourish. After the fields have grown to their full potential, the mayor penguin 1608 may appear and provide the player with a stamp 1612 on his or her stamp card 1613. Each time the game is played, a different type of fruit or vegetable may be grown. Additionally, the food from the fields may be harvested and the particular type of food grown may be seen in the lobby game. The food may temporarily fill a stockpile for the villagers that they gradual diminish, thereby encouraging the player to continue watering the fields to grow more food. In the lobby game, the player may see the villagers cooking, selling, and eating the food the player helps generate.

Bird Reach

Figure 21:
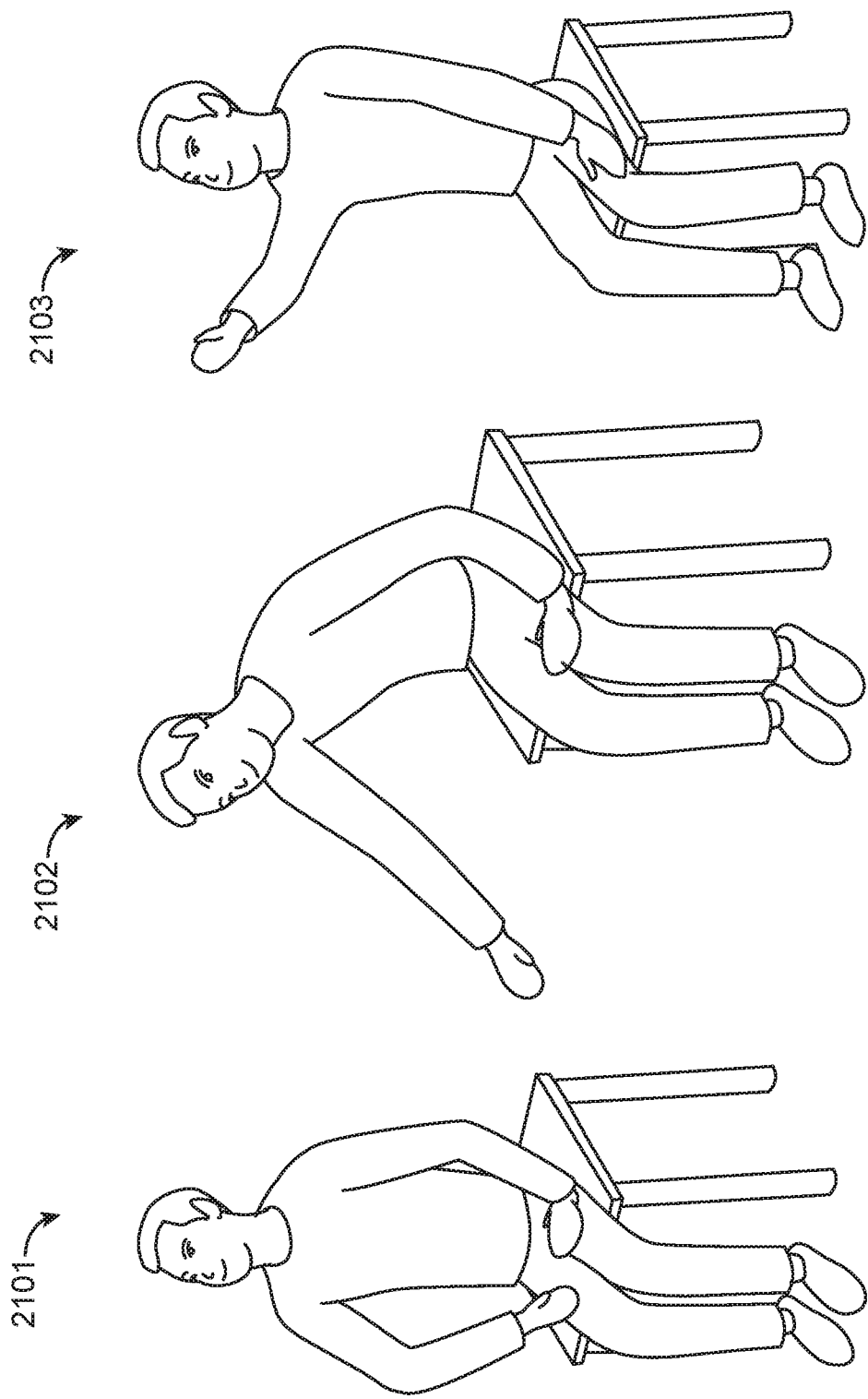
FIG. 21 illustrates example movements in a reaching therapeutic exercise, in accordance with some embodiments.

The present invention may include several variations of a reaching therapeutic exercise involving birds. FIG. 21 illustrates the movements a player may be encouraged to make during the bird reaching games. The performance of these games typically requires, measures, and tests a combination of functional reach, wrist pronation/supination, trunk stabilization, and cognitive abilities. The player may start in an upright seated position 2101, reach down 2102 for a bird, wherein the bird jumps into the player's hand, and then reach up 2103 to place the bird in a nest, wherein the bird leaves the player's hands when the hand gets close enough to the nest or when the player's wrist pronates or supinates so much that the bird jumps off.

Figure 22A:
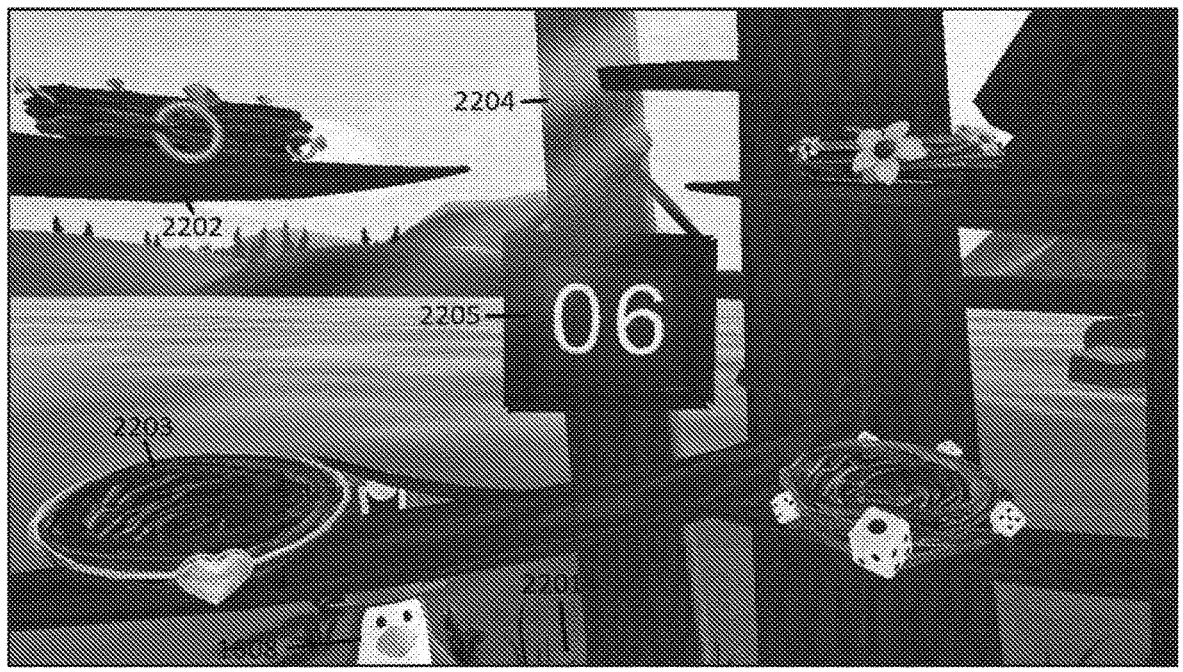
FIGS. 22A-22E illustrate a sandbox bird reach activity, in accordance with some embodiments.
Figure 22B:
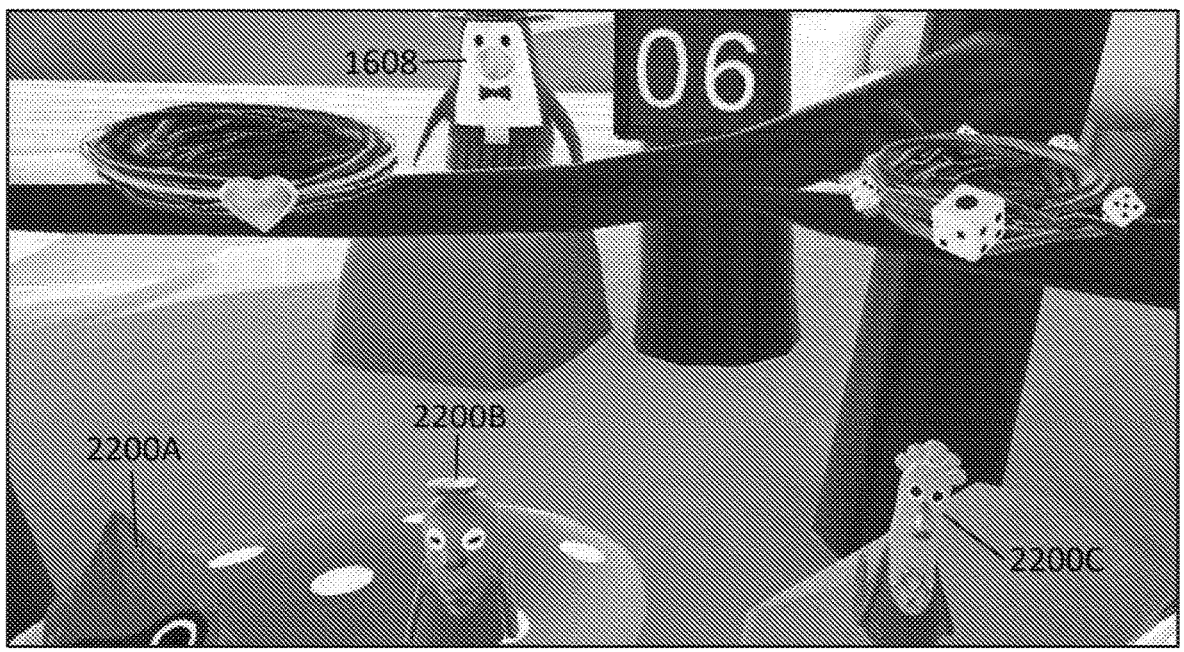
Figure 22C:
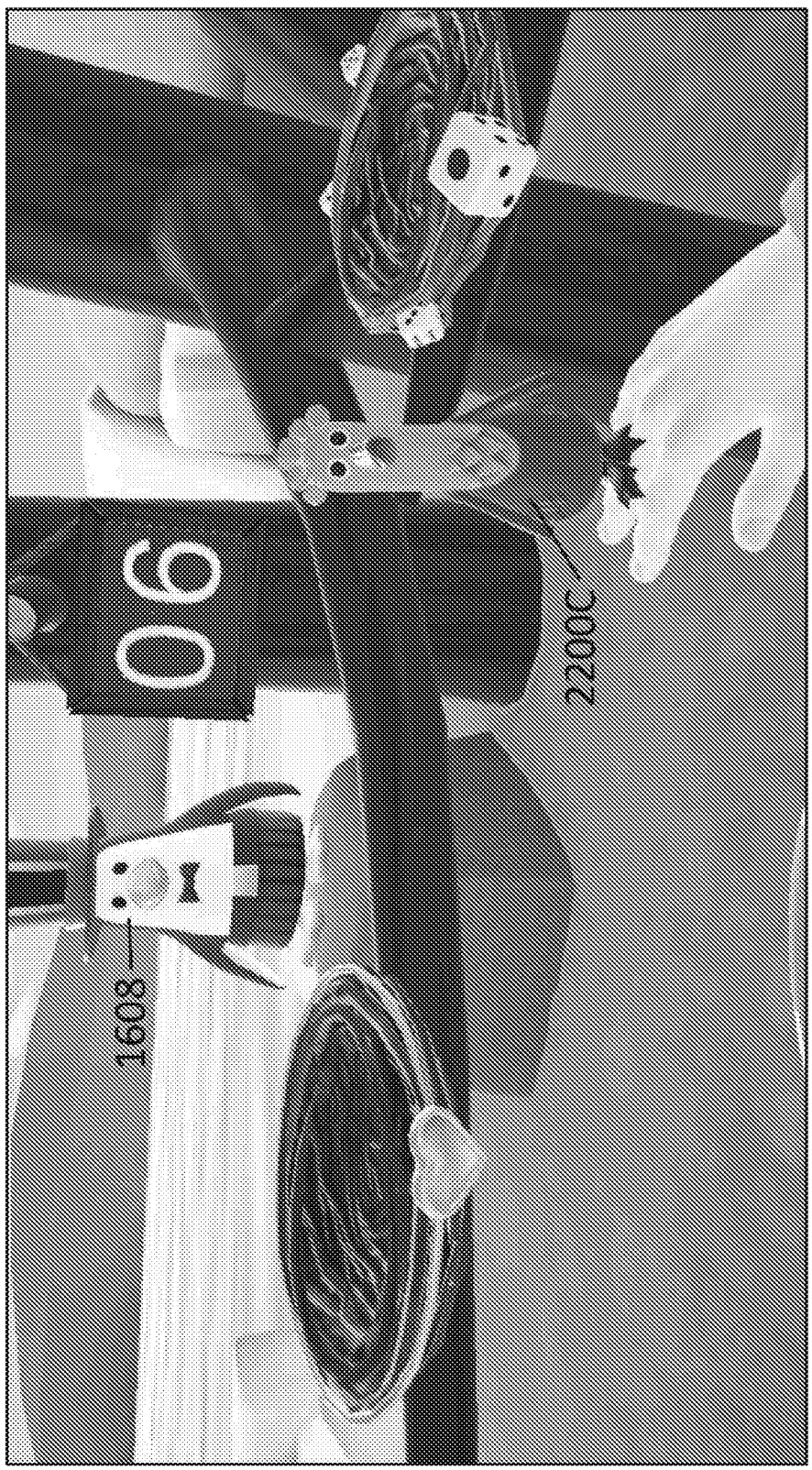
Figure 22D:
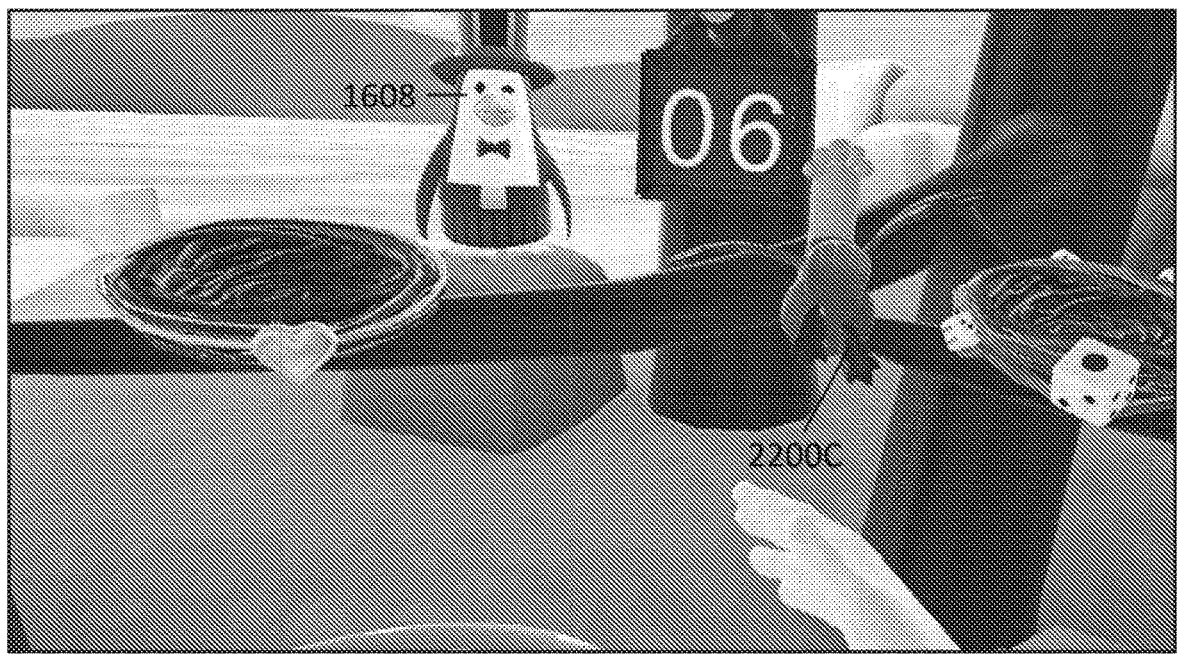

As illustrated in FIGS. 22A-22G, when a player is loaded into a bird reach therapeutic exercise, they will find themselves seated in a forest 2201 with branches 2202 supporting a series of birds' nests 2203. Typically, each individual nest has its own distinctive markings. One of the trees 2204 may include a scoreboard 2205 that either counts down or counts up for successful reps. When the player looks down, a perspective illustrated in FIG. 22B, the player will see birds 2200 on the ground, on stumps, on trees 2204, or on other various objects in front of the plater. Here, the player can see a red bird 2200A, a purple bird 2200B, and a blue bird 2200C. Other birds with different colors may be visible from other perspectives. The player will be encouraged to reach out to the birds 2200 with their hands flat, e.g. palms facing up or down. FIG. 22C illustrates an example of a player reaching out to the blue bird 2200C, wherein it jumped onto the player's hand. If the player then reaches out to a nest 2203, the bird 2200 will jump into the nest 2203 if the player's hand overlaps with the nest 2203 or the player turns their wrist via pronation or supination near the nest. If the player turns their hand over with their second hand under it, the bird 2200 will jump to the other hand. If the player turns their wrist over too far from a nest 2203 and too far from their other hand, the bird 2200 will fly away, as illustrated in FIG. 22D, but the bird will return shortly. Also illustrated in FIG. 22D is an animation the mayor penguin 1608 makes when the player makes a mistake such as this (turning their wrist over too far from the nest). Here, the mayor penguin performs a wink animation when the player misplaces the bird, thereby responding to the players action while staying positive during the player's performance of the exercise. Each bird 2200 that is placed in a nest will sing a unique tune as an indicator of a successful placement. As several of the birds 2200 are relocated, a symphony will arise. When all the birds 2200 have been placed into nests, the symphony will reach its crescendo. The progression of the song offers short-term feedback.

Free Birds

Figure 22E:
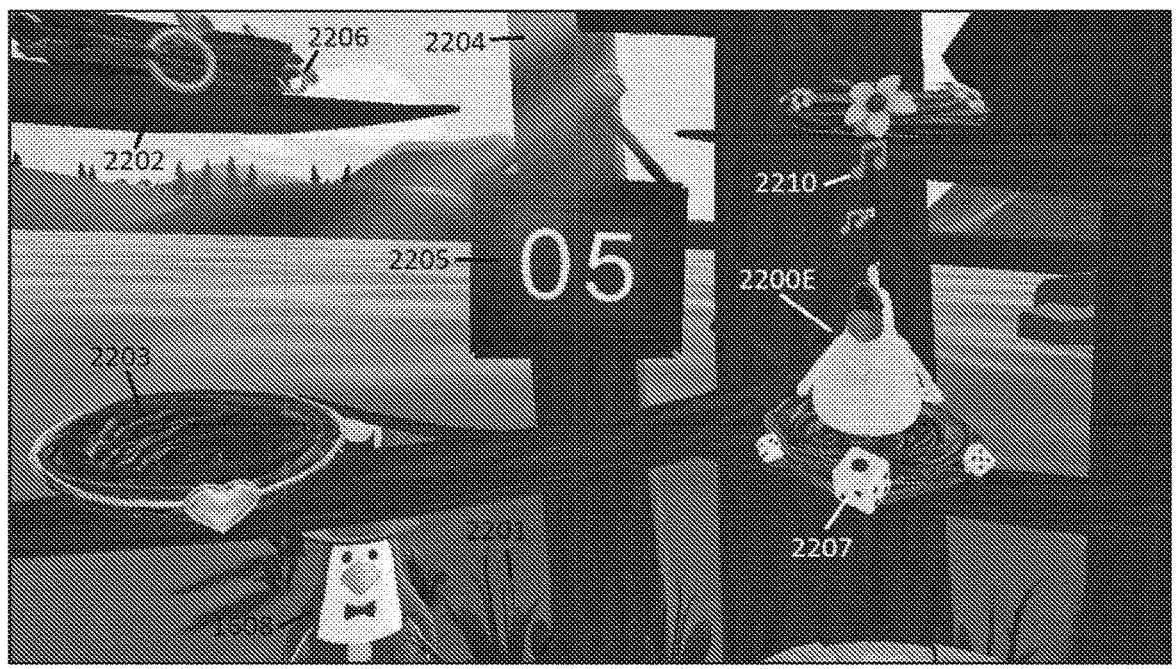
Figure 22F:
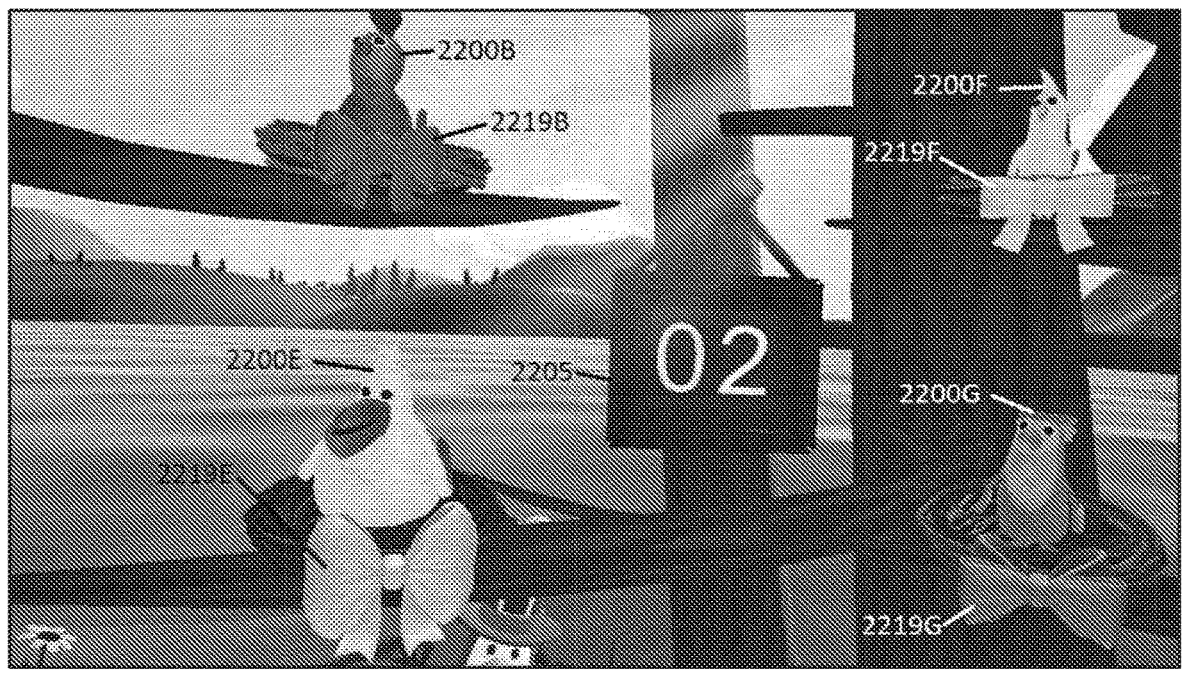
FIG. 22F illustrates a sorting bird reach activity, in accordance with some embodiments.

FIGS. 22A-22E illustrates a first embodiment of a bird reach therapeutic exercise, the player is presented with numerous nests 2203 with distinctive markings and numerous birds 2200 of a variety of colors below the nests. The nests 2203 may distinctly include objects like diamond rings 2206, bolts, dice 2207, etc. so that they can be called out with specificity by a practitioner. The player is tasked with picking up birds 2200 and placing them in nests 2203 in any particular order. In FIG. 22D, no birds 2200 have yet been placed, and the scoreboard 2205 reads 6. In FIG. 22E, after the white bird 2200E has been placed, the score board 2205 reads 5, counting down the number of reps required. After the white bird 2200E is placed into the dice nest 2209, it begins singing a tune, as illustrated by the musical notes 2210. All versions of the bird reach therapeutic exercises can be adjusted to change the placement mechanism—either by overlap, wrist pronation/supination, or both—the number of nests 2203, the distance of the branches 2202 and the nests 2203 from the player, how quickly the birds 2200 return after flying away, and the number of birds 2200 that need to be placed (i.e. number of reps) to complete the game. In one example, a default setting requires 6 reps. Colorful birds FIG. 22F illustrates a second embodiment of a bird reach therapeutic exercise. Here, the player may be presented with a purple bird 2200B, a yellow bird 2200F, a white bird 2200E, and a green bird 2200G (and others that are not visible). In this version of the game, the nests 2203 are wrapped with ribbons tied into a bow. Each ribbon has a different color that matches the colors of the birds. FIG. 22F shows a purple ribbon 2219B, a yellow ribbon 2219F, a white ribbon 2219E, and a green ribbon 2219G wrapped around individual nests 2203. In this version, the player will only get credit for placing a bird in a matching nest. This introduces a cognitive element to the game that may be helpful to victims recovering from diseases like a stroke. If the bird is placed in nest having a different color, the bird may land in it, but the scoreboard with not give a point and the bird will jump out of the nest if touched again. If the bird is placed in the correct nest, it will be locked in place and the player will not be able to pick it up again. In this example, four birds have been placed and the scoreboard 2205 reads 2, indicating the game is over once two more birds are placed (in nests not visible in FIG. 22F). In some embodiments, the game is over when the scoreboard counts down to zero, starting at six, nine, twelve, or fifteen, as selected by the user. In another embodiment, the scoreboard counts up, and every time it reaches a multiple of six, the mayor penguin 1608 may present the stamp card 1613 and place a new stamp 1612 on it. In another example, the game is over when every nest is filled with a bird. The difficulty of the color matching game may be enhanced by having the birds initially orientated opposite to their corresponding nests. This will require that the player reaches to one side of their body first to pick up the bird and then must cross their body and reach to the other side to place the bird. Likewise, the bird may be initially positioned low and the nests high, or vice versa. On the other hand, the game can be made easy by having the birds start near the nests they belong in.

Timer Nest

Figure 22G:
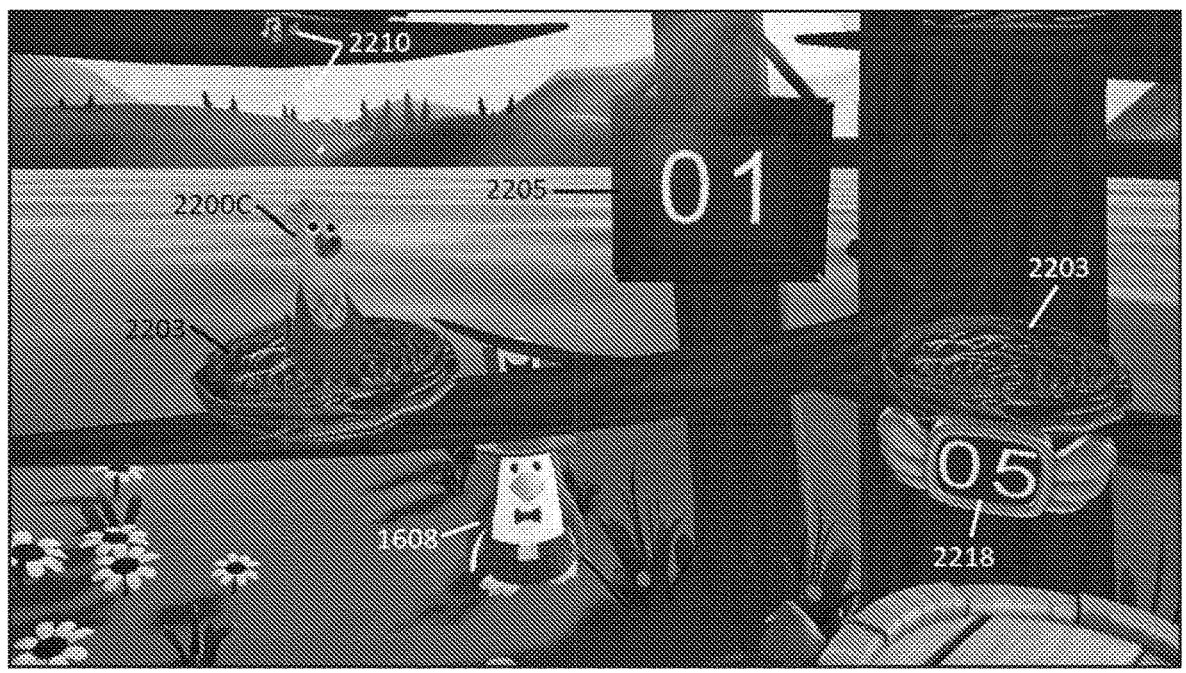
FIG. 22G illustrates a timed bird reach activity, in accordance with some embodiments.

FIG. 22G illustrates a third embodiment of a bird reach therapeutic exercise. Here, the player is presented with numerous nests 2203 and one bird 2200C. In this version, one of the nests has a timer 2218 wrapped around it counting down, for instance from 10, and once the countdown finishes, the timer will disappear and reappear on a different nest. In this game, the player must place the bird 2200C in the nest before the time runs out to score a point. Here, the bird has been placed successfully once, and this success is communicated by the bird's song 2210 and the score board 2205 reading 01. If the bird is placed in a nest after time runs out or is placed in a nest without a timer, the bird will land, but no points will be collected. The timer may rotate between six nests in a clockwise, counterclockwise, or random manner. Alternatively, the timer may be restricted to central nests, left side nests, right side nests, or some such combination. This adjustability will allow the player to focus on specific motions or specific limbs, which is particular helpful for stroke victims with weakness on only one side of their body. The difficulty of this game may be adjusted by changing how long the timer stays on individual nests.

Fish Block & Dodge

Figure 23:
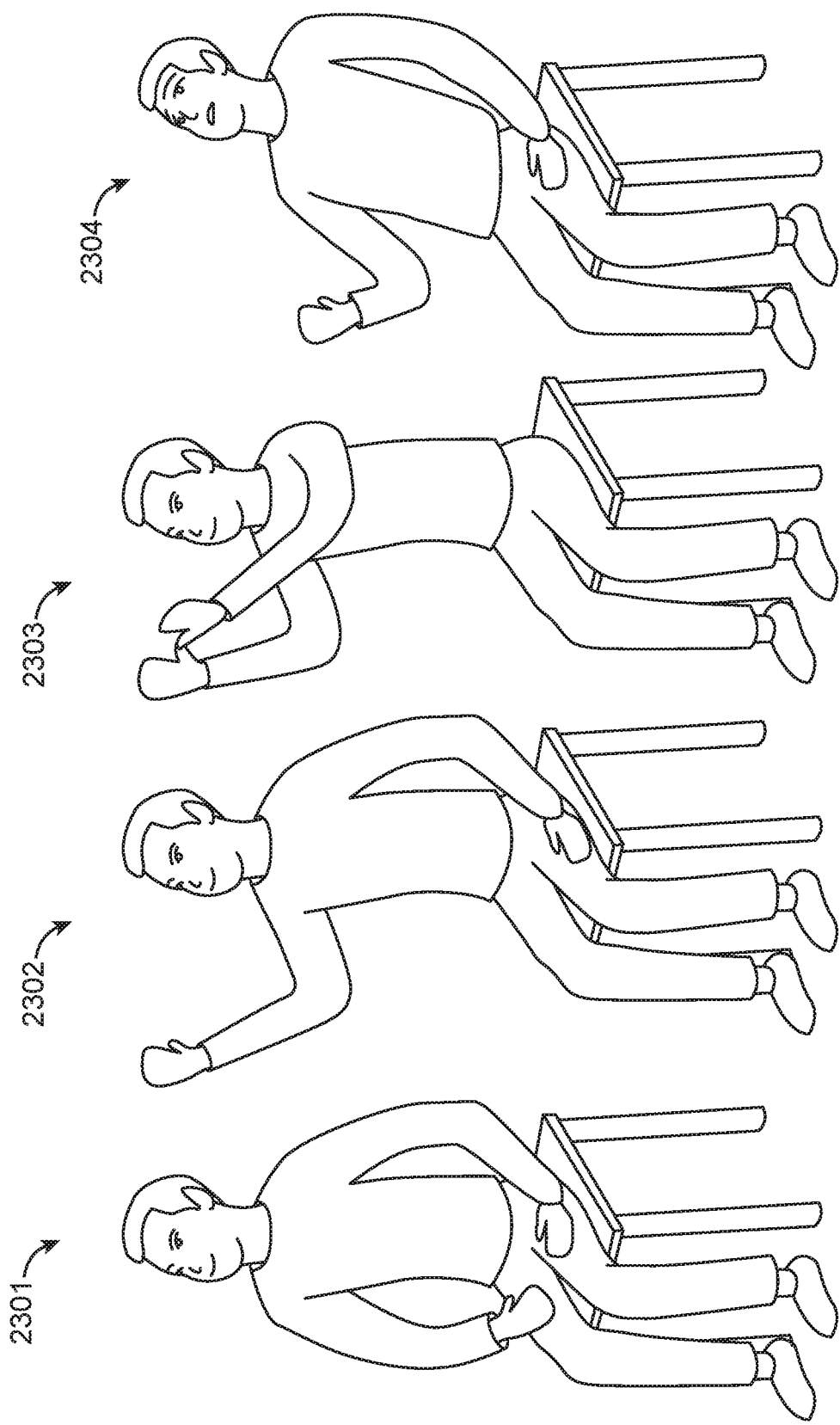
FIG. 23 illustrates example movements for intercepting and avoiding a projectile, in accordance with some embodiments.

The present invention may include several variations of a soccer-like therapeutic exercise. FIG. 23 illustrates the movements a player may be encouraged to make during the blocking and/or dodging therapeutic exercises. A player may start in a neutral position 2301, the player may block 2302 a projectile with one hand, the player may block 2303 a projectile with two hands, and the player may dodge 2304 a projectile by leaning outside of its trajectory. When the player is loaded into a soccer therapeutic exercise, they will typically find themselves on the receiving end of kicked soccer balls and/or flying fish that must be blocked, reflected, or dodged to score points. The player may score additional points if the balls or fish they block, dodge, or deflect go through a goal, hit the kicker or thrower, or hit one of the villagers or animals standing around the game. The performance of the game typically requires, measures, and tests reaction time, reach, and trunk stabilization. This game plays on the instinctive, reactive movement associated with blocking or catching.

Penguin Sports

Figure 24A:
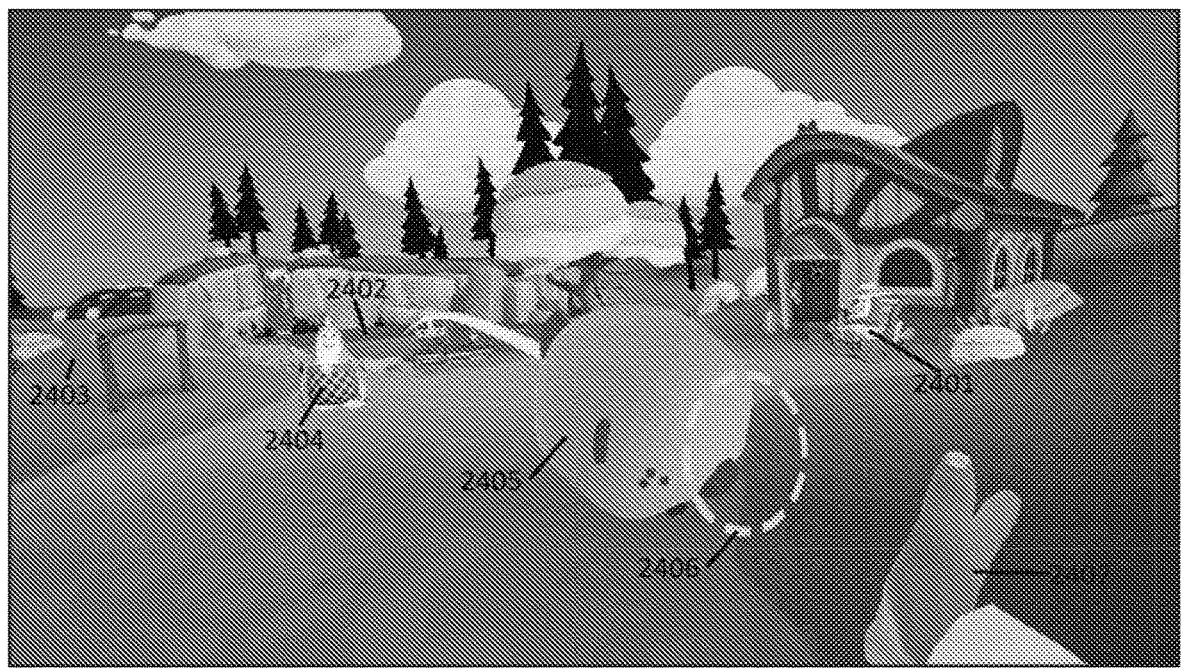
FIG. 24A illustrates a sandbox blocking activity, in accordance with some embodiments.

FIG. 24A illustrates a first embodiment of a soccer therapeutic exercise. Here, the player is loaded into a campground on top of a small hill, with an aspiring artist to their left, a nosy neighbor 2401 to their right. Further away in the background, there is a lake 2402 to the right and a sports field 2403 to the left. This is a sandbox game with no clear end point or win objective. It is designed to acclimate the player to the game mechanic of blocking projectiles in virtual reality. A plaid clad penguin 2404 in front of our player will inflate and kick an inflated chuckleball 2405 toward the player. The player can choose to use one hand, both hands, or their head to block the ball. The player may be provided with a dotted-line-circle 2406 that indicates where the player should place his or her hand(s) 2407 to block the projectile. When a ball hits the kicker, he will interact and laugh in enjoyment.

Chuckleball

Figure 24B:
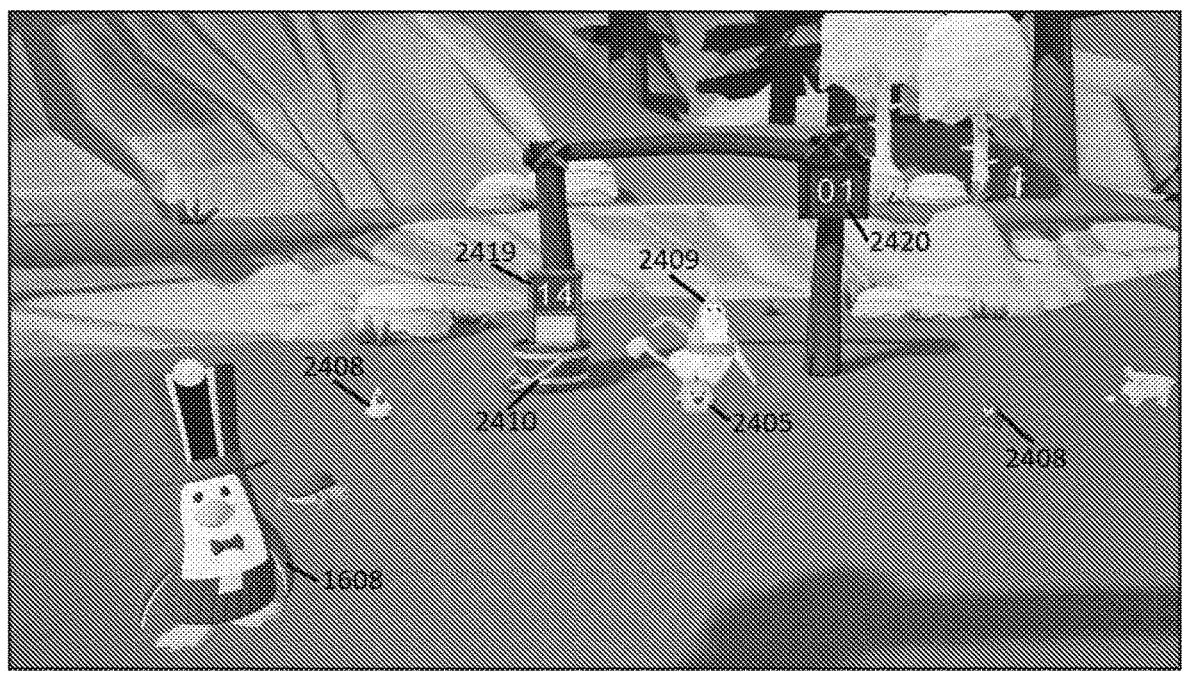
FIGS. 24B-24C illustrate a Chuckle Ball activity, in accordance with some embodiments.
Figure 24C:
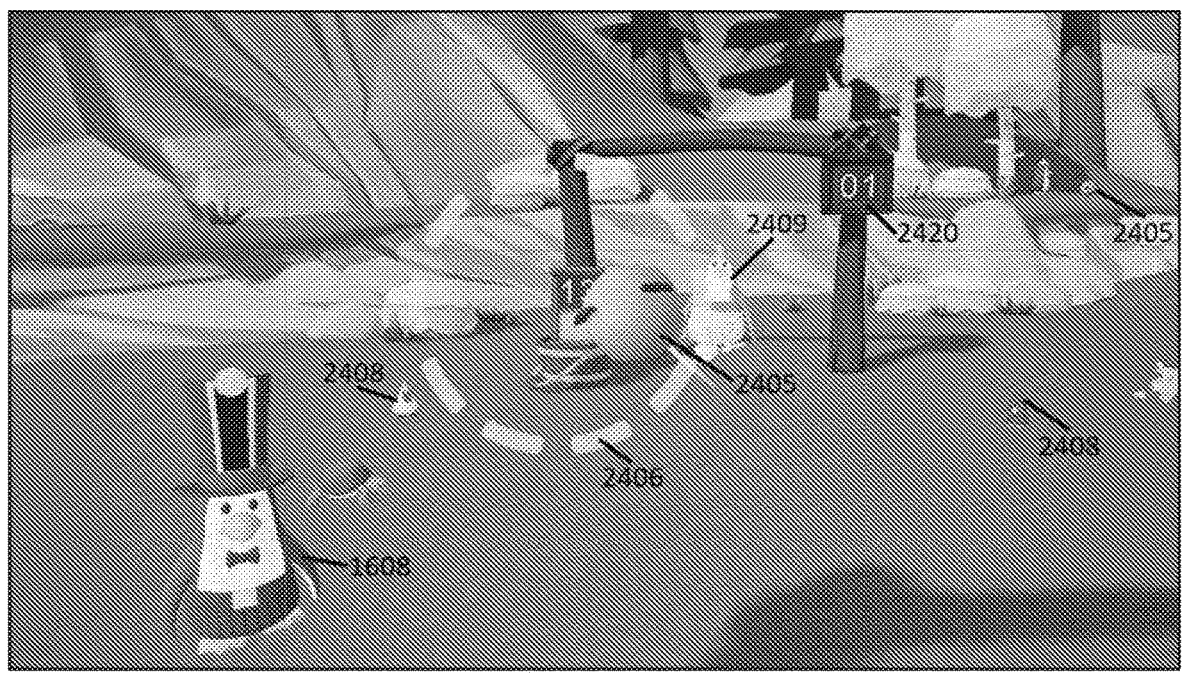

FIGS. 24B and 24C illustrate a second embodiment of a soccer therapeutic exercise. Here, the player may be joined on the sports field by a jazz band, birds 2408, Mayor Penguin 1608, a kicker penguin 2409 a variety of animals and two casual penguins kicking a chuckleball 2405. The goal of the game is to block the chuckleballs 2405 from making it through the player's goalpost (not visible). The player may be provided with a dotted-line-circle 2406 that indicates where the player should place his or her hand(s) 2407 to block the projectile. The player receives a point for each blocked ball and receives extra points for deflecting the ball so that it bounces into other virtual characters in the level. These points will be recorded by scoreboard 2420. Typically, the virtual characters will perform a cute animation when they are hit with a chuckleball 2405. The birds may fly away temporarily after being hit or scared away but will return to the field to watch the action once again. The reps and win condition of this game can be adjusted to change the number of chuckleballs kicked, the number of blocks required, the speed of the kicks, the distance the player must reach, and the interval between kicks. In the example illustrated by FIG. 24B, the kicker penguin 2409 has 14 chuckle balls left in his bucket 2410, as indicated by the bucket counter 2419.

Flying Fish

Figure 24D:
FIGS. 24D-24F illustrate a flying fish blocking and dodging activity, in accordance with some embodiments.
Figure 24E:
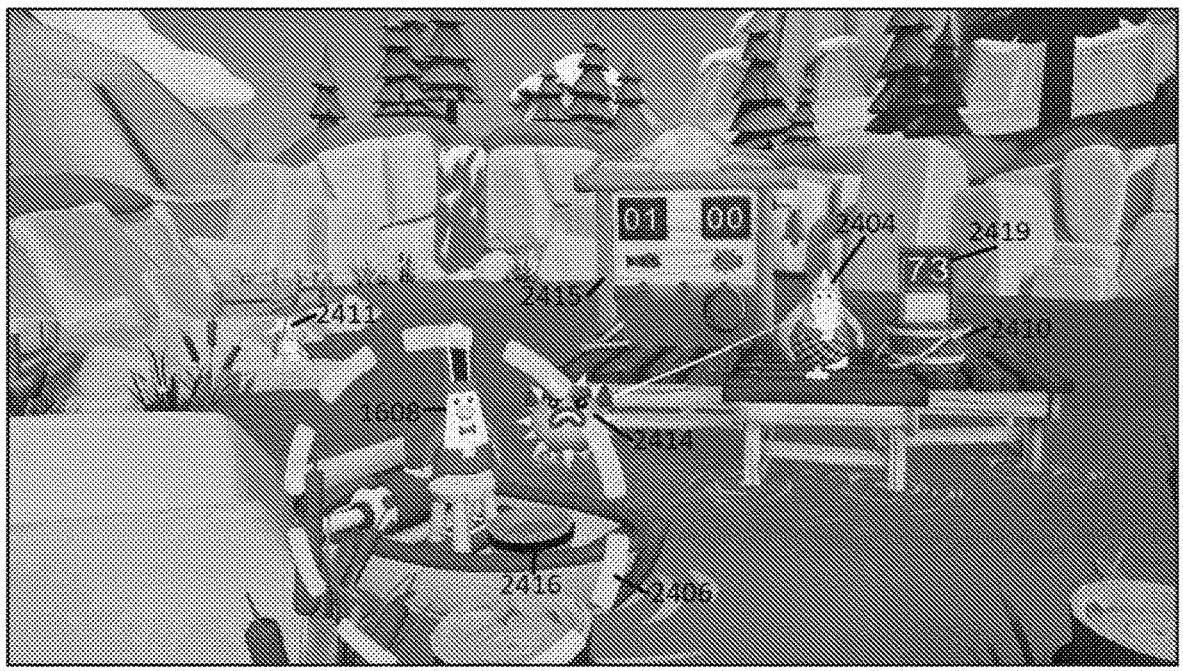
Figure 24F:
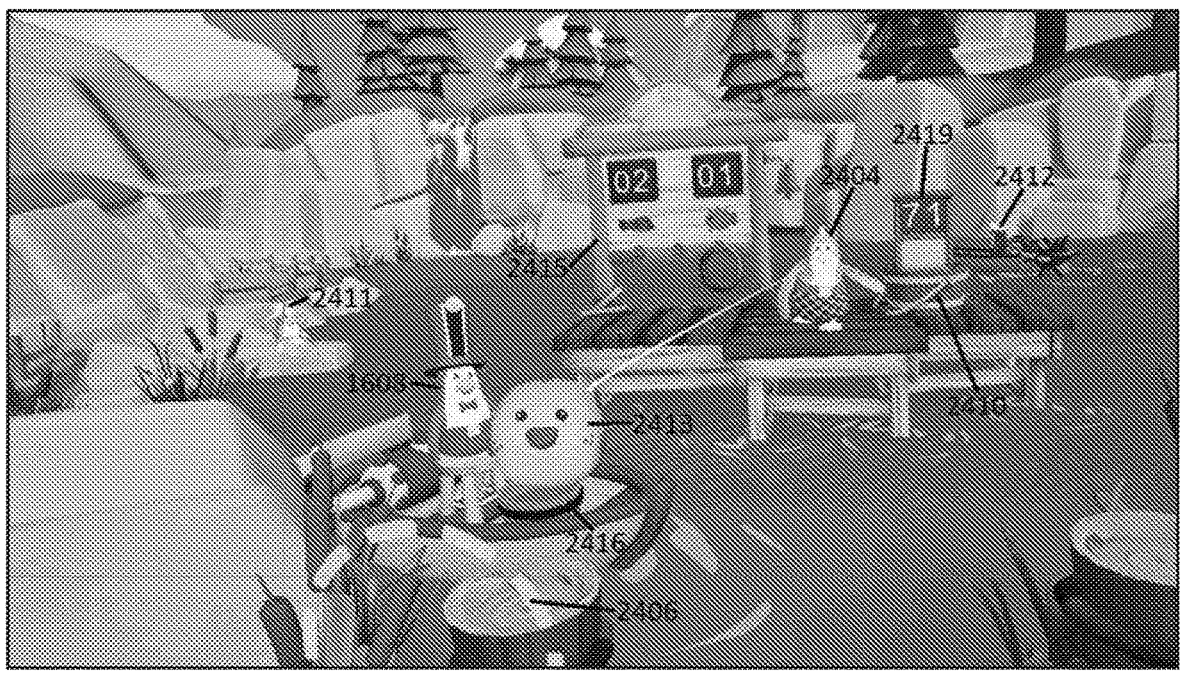

FIGS. 24D-24F illustrate a third embodiment of a soccer-like therapeutic exercise. Here, the player is seated lakeside with the plaid clad penguin 2404 who no longer kicks things but throws them instead. The onlookers from the previous soccer-like games gather around to watch the action. In addition, out in the lake the player may see a red bird riding a shark, a fishing penguin 2411 lakeside, mayor penguin 1608 in a boat, blue penguin on swing, sailor penguin 2412 in a powered boat. The plaid clad penguin 2404 has made a large catch of fish. The fish are in a bucket 2410 and the number of fishes is indicated by a bucket counter 2419. The plaid clad penguin 2404 reaches into the bucket 2410 to randomly select a fish to throw at the player. The goal of this game is to block the blue fish 2413 and dodge the red fish 2414. A dotted-line-circle 2406 may appear when a fish is tossed, indicating where the player needs to block or dodge. The scoreboard 2415 will record how many correct interactions the player achieves. In one example, the scoreboard 2415 has an individual count for both blue and red fish and counts up from zero for both. For example, after a blue fish is blocked the blue fish count will go up one—a blocked blue fish may bounce into a collection bucket 2416 positioned in front of the mayor penguin 1608—and after a red fish is dodged the red fish count will go up one. Like the previous game, this one is adjustable for number of pitches, speed of pitches, reach distance required, and interval between pitches. Additionally, the game is adjustable for percentage of red to blue fish and the game is adjustable for when a red fish's color is revealed. In an easy version, the fish turns red during the wind up of the pitch, in a medium difficulty, the fish turns red when it leaves the pitcher's hand, and in a hard difficulty, the fish turns red in-flight. Red fish will typically default to alternating between being pitched at the hand regions and head regions.

Falling Objects Game

The present invention may include several variations of a therapeutic exercises centered on catching projectiles. In one example, a player is tasked with catching virtual objects thrown by a practitioner. The practitioner may use a tablet computer with a touch screen to throw objects. In one example, the objects are thrown with a direction and speed proportional to a swipe of the practitioner's finger across the screen of the tablet. The player scores points for making catches and may be rewarded with a stamp from the mayor penguin for a given number of catches. The practitioner can make the game more or less difficult based on how they swipe the screen on the tablet. In another example, the player is tasked with catching objects falling from an overhead apple tree. The apples fall randomly from the tree and the player needs to catch them before they hit the ground to score points. In one version of this game, the player plays on a tabletop. When an apple is about to drop, a ring will appear on the table where the apple is going to fall. The player then must reach one of their hands into the ring before the apple falls through. Within virtual reality, the player may see a glass table, and beneath the table is a city. If an apple is not caught, it will fall through the virtual glass table and, being a massive apple, damage the city. The difficulty of this game may be adjustable. The user may adjust the distance the player must reach, the time the player has to catch the apples, how early the ring appears on the table, how fast the apples drop, or how big the apples are. For instance, each time a successful catch is made, that landing position may be removed from the game, which will cause the game to select newer and newer landing positions until the player reaches the edge of how far they can reach on a table top.

Figure 25:
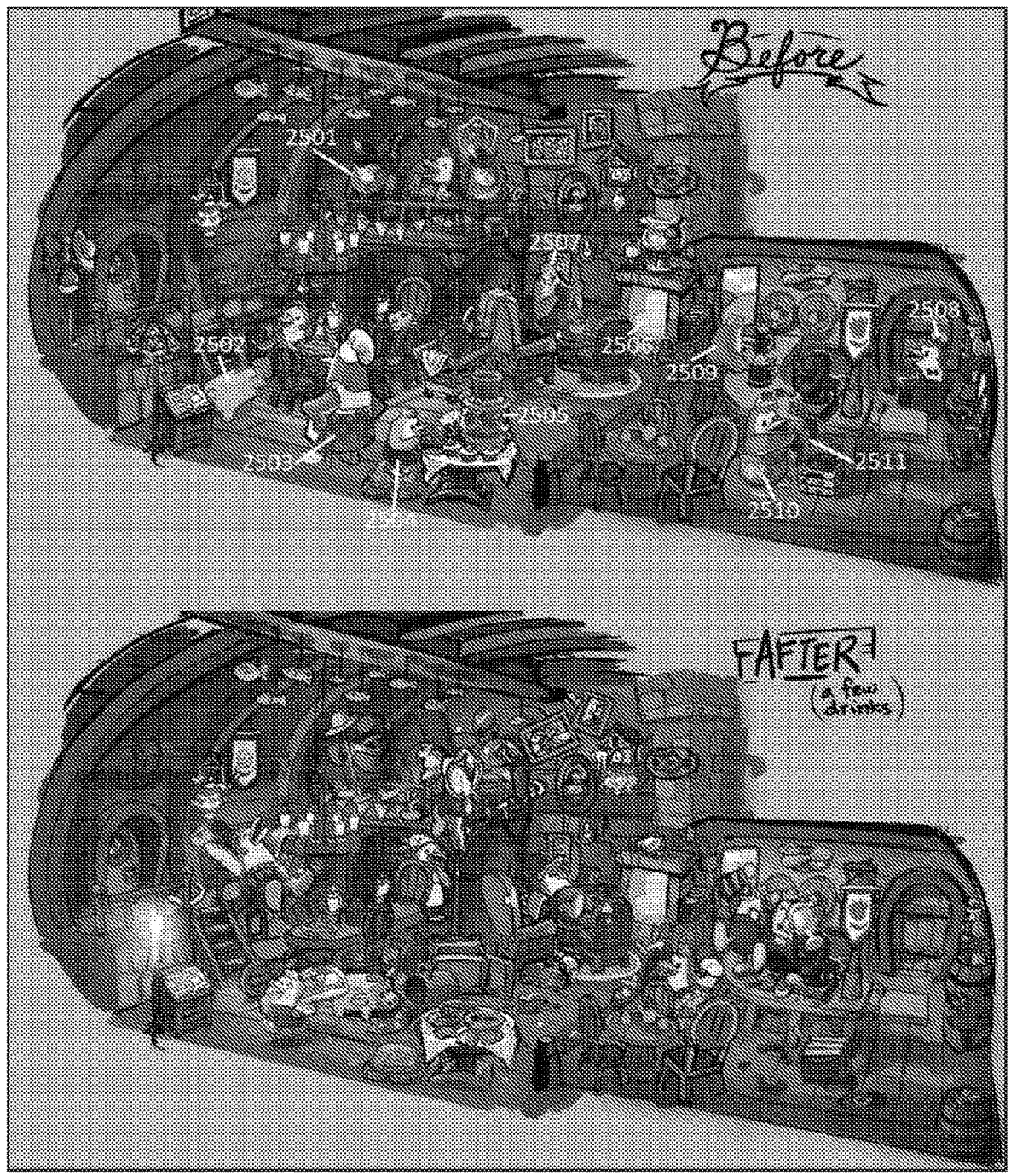
FIG. 25 illustrates a gaze game activity, in accordance with some embodiments.

Gaze Game:

FIG. 25 illustrates an embodiment of a therapeutic exercises centered on directing a player's gaze to various positions in the 360-degree virtual reality environment. In this example, a player finds themselves seated in a room full of energy and vibrance. The room may include a band 2501, a pig 2502, a chef 2503, a kid penguin 2504, a cake 2505, a fire place 2506, a reading penguin 2507, a bartender 2508, a bar patron 2509, and a music penguin 2510 playing a record 2511. At the start, everyone is enjoying the peaceful and relatively relaxed setting. However, as the player gazes at a villager or item, it will spring into action. For instance, gazing at the kid penguin 2504, may cause it to reach for a piece of cake 2505, which it knocks over. If the player next gazes at the pig 2502, the pig may run over and start eating the cake. If the player looks at the chef 2503 next, the chef may chase after the pig 2502 and run into the record 2511 and break it. If the player looks at the bartender 2508 next, it may offer the music penguin 2510 a drink. If the player looks at the music penguin 2510 next, it may climb on the bar with the bartender 2508 and bar patron 2509 and start dancing on the bar. In this manner, the gazing starts a chain of events whose order is determined entirely by the order in which the player gazes at them. By activating different villagers and different objects in different orders the outcome can vary drastically from session to session. Finding the alternate endings and any hidden Easter eggs will encourage continued participation as the players tries to find every combination that leads to a different outcome. In other examples, the player may look at items and the villagers will respond by interacting with that item. For instance, by looking at a tap behind a bar, the bartender 2508 may fill up a glass and place it on the table, and by looking at the filled glass a villager may go over and start drinking it or bring it to the player.

Painting Game

The present invention may include several variations of a therapeutic exercise centered on painting. In one example, the player is situated in a virtual reality environment in front of an easel covered in canvas that includes a paint palate and brushes on a side. The player is prompted to reach for the brushes, dip them into a color of choice from the paint palate, and apply the paint onto the canvas. The game requires both fine motor control and sweeping motions, both of which may be challenging for victims recovering from a stroke.

Water Fall

The present invention may include several variations of a therapeutic exercise centered around a waterfall, series of waterfalls, or waterpark like structure. In one example, the player finds themselves in front of an elaborate array of waterfalls and pools. The water coming out is minimal and the village needs more water for crops, drinking, and fun. The player is prompted to raise a hand and bend their elbows at an angle of around 90-degrees. A practitioner may then hand them an elastic band attached to a stationary object. The player then performs shoulder abductor or adductor exercises by moving their hand side-to-side while maintain the elbow bend of around 90-degress. For each arm, the player may benefit from alternating from an elastic band attached to their right and one attached to their left so they can exercise both sides of the rotator cuff. Each rep of the exercise will cause increased water flow through the waterfalls, which will fill the pools, and eventually disperse into the village. The immediate feedback will be the quantity of flowing water, while the long-term feedback will be the village's response. As more water flows into the valley it will become lush, and the crops of the inhabitants will thrive, and waterwheels will turn and provide additional benefits to the villagers. A stream may grow into a river as the patient progresses through more and more exercises, which serves to provide additional long-term feedback.

Wood Chop

The present invention may include several variations of a therapeutic exercise centered around wood chopping. The player may find themselves situated in front of a large tree or in front of a chopping block topped with a piece of wood. The player will be tasked with chopping the wood, so the villagers can build a structure and/or stay warm. The player will chop wood by performing a shoulder adductor (towards the body's midline) exercise. For example, the player's right arm will be bent at a 90-degree angle, they will grab an elastic band fastened to their right, they will then pull on the band towards their left side, while maintaining the angle in their right elbow. Each rep will chop a piece of wood or take a piece out of a large tree. With additional reps, the tree will grow weaker and weaker, and perhaps through a full exercise cycle the tree will fall down. That will provide the immediate feedback, while the long-term feedback will be the villagers amassing of lumber for their various needs. The villagers may use the player's efforts to clear spaces for new houses, and the wood harvested may be directly tied to the construction of log cabins or other structures that look like they are heavily composed of wood.

Difficulty Adjustments & Scheduling

The various therapeutic exercises of the present invention typically include adjustable difficulty settings. These setting may be manually controlled by a player or user. Alternatively, the difficulty is automatically adjusted by algorithmic difficulty scaling. An algorithm may measure a player's movements to determine range of motion and other various indications of ability while the player performs a selected therapeutic exercise. In one example, an algorithm establishes a window around the detected range of motion. Movements that get within 10% of detected range of the first few reps are counted as full reps. In another example, an algorithm counts the first few reps as full reps and averages those reps to establish what counts as a full rep going forward. Then the algorithm continues to monitor the player, and if their performance increases or decreases, the algorithm may slowly adjust the difficulty so that they more often than not tend to barely complete a rep. This algorithm beneficially keeps the player's effort high, as they barely miss and barely complete rep after rep, but achieve it nonetheless.

In another example, an algorithm is loaded with data on what kind of recovery can reasonably be expected for a given player (e.g. a specific range of motion), and that serves as the upper threshold of achievement for the specific iteration of the game that they play. The algorithm will then monitor the patient's progress and determine a difficulty curve that matches the patient's progress and the expected upper limit. The game may be progressively harder as the player improves. However, if the player regresses, the algorithm may reduce difficulty to keep the player engaged and to keep them motivated to continue. Algorithmic difficulty scaling addresses the issue of boredom and frustration experienced by players when a game is either too easy or too hard.

The rational for adjusting difficulty is that if a game is too easy it becomes boring. If a patient is rewarded for a small movement, and then with further rehab can perform that motion easily, the patient will not be sufficiently challenged. On the other hand, if the game offers no rewards at all when the player first starts, and they see nothing but failure, they will become frustrated and discouraged from continuing. The algorithm's objective is to find the balance between these two extremes.

An algorithm's decision making may be continually updated as the game is implemented over several iterations. The game may capture various parameters, such as repetitions, range of motion, level achieved, environment, and other relevant parameters that can be used in the backend for verifying the efficacy of the treatment, the player's current health, and the player's progress in through the therapeutic exercises of the present invention. Optionally, the present invention will offer exercise suggestions or plans based on exercise analysis.

Themes

The game may implement a variety of different themes that are all designed to transport the player to a different world. The themes may simply offer a different paint on the same general world. However, ideally each exercise or series of exercises comes with a detailed and customized experience, not merely a different background. It is desirable for any theme to be fully integrated with the landscape and the exercises to make the world and the experience fully mesh.

Figures 26A, 26B:
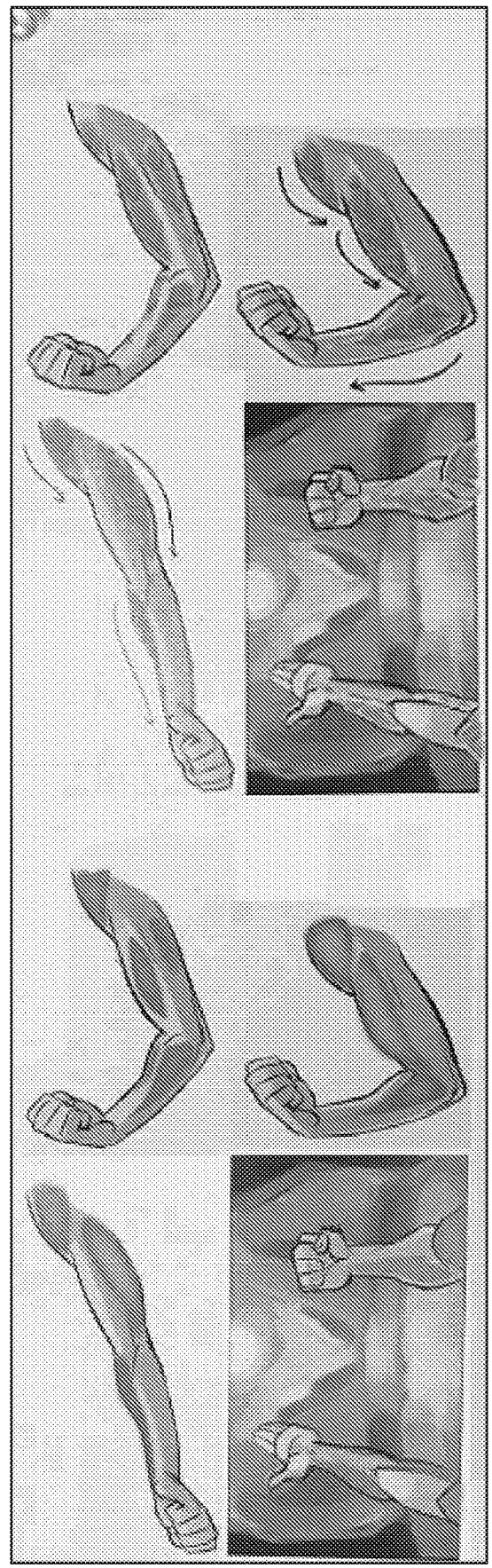
FIGS. 26A and 26B illustrate examples of avatar limbs that light up to show nerve action, in accordance with some embodiments.

The themes of the present invention may include a virtual world like small town USA. The small town will be reminiscent of a kinder, simpler, and slower time. The artwork of the town is inspired by American Regionalist painters, such as Norman Rockwell. The virtual world may be within a space station orbiting earth, where gravity manipulation exercises would be easier to appreciate by the player. The virtual world may be within a homestead/ranch, where the player can chop firewood, light a stove, cook breakfast, or care for animals. The virtual world may also include a Japanese garden, a sort of meditative place, where slow pace and good form receive extra rewards. Architecture is inspired by Japanese gardens but have a "magical" influence. In one embodiment, the theme will be x-rays. Physical therapy isn't strictly about muscles, neural pathways and nerve endings are often what needs rehabilitation the most. To showcase the importance of nerves, the game may show the nerves on the player's avatar. The player will be able to see all of the nerves in their avatar by looking down at their avatar and/or at a mirror in the virtual reality environment. The player's avatar may light up and show how the nerve endings communicate in each step of an exercise. FIGS. 26A and 26B illustrate examples of avatar limbs that light up to show nerve action. FIG. 26A shows a simple glow for the muscles when they are fired and FIG. 26B shows directional arrows for nerve firings when they are fired.

Encouragement

The goal of the present invention is to get people out of the hospital both by virtually transporting them away and by speeding recovery to literally allow them to leave the hospital. The present invention helps patients forget they have a disability and forget they are in a hospital. The present invention shows patients that they are improving with every exercise. The present invention will reveal a beautiful landscape full of possibilities and freedom. Freedom from injury and stagnation. And, importantly, the present invention will encourage therapy participation and reward effort and consistency.

Rewards

A classic form of encouragement or motivation in life and video games alike is a reward system. Post-stroke therapy is painful and challenging, with early progress typically being imperceptible. The first recognizable signs of improvement are slow coming. As such, a problem exists in physical therapy that the present invention satisfies. In the early stages of therapy, the virtual reality environment and the therapeutic exercises performable there offer innumerable signs of progress and improvement. The games and the villagers surrounding the therapeutic exercises makes early physical therapy full of wonder, inspiration, and joy. The game encourages and rewards participation, when a patient may otherwise be discouraged by observing their mobility alone.

Figure 27:
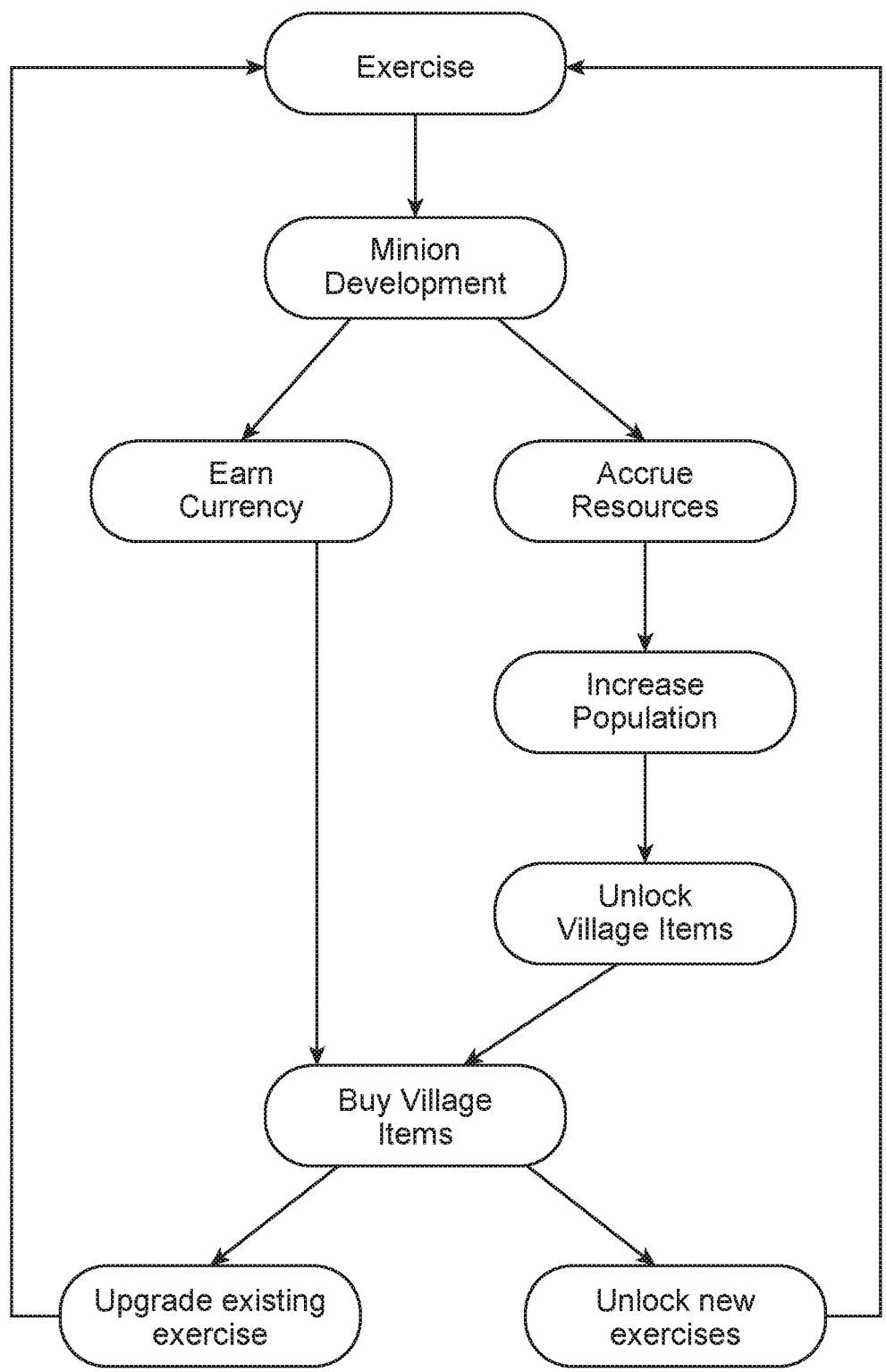
FIG. 27 illustrates an example reward and incentivization pathway, in accordance with some embodiments.

Some rewards may be easily obtained while other rewards may have a more difficult pathway. With each exercise, the player may immediately receive some sort of currency, whether it be coins, experience points, stamps, or levels. Such rewards offer an easily understandable and measurable mark of progression. As the player accumulates coins, they are given a sense of success. They have done something. Their efforts have been translated into something valuable. For instance, coin collection can be a proxy for success and even a proxy for effort absent success. FIG. 27 illustrates a possible reward pathway that may encourage continued participation in the present invention's virtual reality physical therapy.

Other rewards may include cosmetic rewards for the player. These rewards may be for the player's own avatar, such as clothing or jewelry, or for the valley and village, such as a new building or new wildlife. The rewards may be a specific building within the valley, or the reward may unlock a gate into a new area of the valley or a new valley itself. The rewards may also be tied to specific achievements. Such as an award, title, or badge for performing 5 sets of every exercise, for maintaining perfect posture for 5 minutes, for reaching maximum height in the arm raise, for collecting a sufficient number of specific resources for the village, for maintaining their schedule for a specific period of time, or for simply logging in. Any measure of progress, participation, or consistency may be tied to an individual award that the player may then share with others to show their achievements. The rewards may include loot boxes. The player may receive them after achieving certain benchmarks, or they may be purchased using in-game currency. The loot boxes contain a randomly selected reward and play on the addictive quality of gambling. People like receiving boxes with random rewards, it is exciting, and it leaves them wanting more. Utilizing this addictive quality to encourage participation in therapy turns a weakness in the human psyche into a tool for positive change.

The accumulation of these rewards may serve as a proxy for long-term progress. The rewards may also have a social aspect, such as allowing the player to gift rewards to other patients that are also playing. This reward system is purpose built to cause the players to become invested in the game. They will want to reach the next achievement, they will want to collect a specific item, etc. Importantly, the rewards will also be slightly obscured. The players won't know what is coming next. They won't know how the village will grow and progress. They will be invested in seeing what happens at the end, and they will be invested in seeing how their input and efforts affect the outcome.

Social Media

In one embodiment, the present invention has aspects that are shareable or tradeable online, such as through social media. A social media platform may provide physical therapy users something in common aside from injuries. The present invention offers a positive shared experience. The social media platform may display the player's achievements, their village, and/or their residence in the village. The platform may also enable both anonymous and specific gifting. The platform may encourage early players who have accumulated many rewards to help newcomers. They may gift currency or rewards, or simply encouragement. The platform may also announce patient's progress for other players to "like."

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for facilitating physical therapy, comprising:
a wearable visual display;
one or more wearable sensors configured to be disposed at varying positions on a user, wherein real-world movement of the user is tracked by the one or more wearable sensors;
a processor comprising executable instructions configured to provide:
a virtual reality environment on the wearable visual display with one or more virtual characters and an avatar that represents the user;
at least one therapeutic activity within the virtual reality environment, wherein the therapeutic activity is directed to produce a therapeutic outcome based on the real-world movement of the user corresponding to the therapeutic activity;
exercise analytics that characterize compliance between respective real-world movement of a first side of the user and a second side of the user as compared to a respective range of motion corresponding to the therapeutic activity, wherein the exercise analytics are generated based on data collected by the one or more wearable sensors based on the respective real-world movement of each of the first side of the user and the second side of the user; and
a mid-line mirror protocol for the avatar, wherein:
a first deviation between data representing the real-world movement of the first side of the user and its respective range of motion is compared to a second deviation between data representing the respective real-world movement of the second side of the user and its respective range of motion,
the first deviation is determined to be less in magnitude than the second deviation, and
in response to the determination, a first side of the avatar and a second side of the avatar each display respective virtual movements corresponding to the respective real-world movement of the first side of the user, wherein the first side of the user and the second side of the user are a right side of the user and a left side of the user.

2. The system of claim 1, wherein the one or more virtual characters mimics or mirrors the motion of the user.

3. The system of claim 1, wherein the one or more virtual characters solicits help from the user to cause real-world movement of the user corresponding to one or more therapeutic activities.

4. The system of claim 1, wherein the therapeutic activity is selected from a group consisting of: straight arm raises, arm reaches, catching or blocking projectiles, picking up and placing objects, turning and looking, gazing at targets, dodging, cane raise exercises, rotator cuff abductor and adductor exercises, leaning, twisting, core balance exercises, and arm swinging exercises.

5. The system of claim 1, wherein the therapeutic activity is presented as a game and is selected from a group consisting of: a hide-n-seek game, requiring the user to turn and look, a sun rise game, requiring the user to raise their arms, a bird sorting game, requiring the user to reach and place, a fish toss game, requiring the user to block and dodge, a hot air balloon game, requiring the user to balance, lean, or bend.

6. The system of claim 1, wherein:
the one or ene virtual characters are displayed via the wearable visual display as being in virtual danger; and
the user is able to virtually rescue the one or more virtual characters through the performance of the therapeutic activity, whereby the virtual danger provides motivation to perform the therapeutic activity.

7. The system of claim 1, including a tablet computer configured to display at least a portion of a view of the user within the virtual reality environment.

8. The system of claim 1, wherein:
the executable instructions cause the processor to provide an interaction between the one or more virtual characters and the avatar within the virtual reality environment;
the interaction comprises at least one of an indication to change the real-world movement of the user to conform to the therapeutic activity or an indication of successful conformity of the real-world movement of the user with the therapeutic activity; and
the interaction is configured to promote performance of a portion of the therapeutic activity.

9. The system of claim 8, wherein the indication comprises a change to a direction or a speed of motion.

10. The system of claim 8, wherein the indication comprises an indication to correct posture or balance or both.

11. The system of claim 8, wherein the interaction occurs in response to a measured completion of the therapeutic activity by the user.

12. The system of claim 8, wherein the interaction occurs in response to a measured non-completion or partial completion of the therapeutic activity by the user based on the exercise analytics.

13. The system of claim 8, wherein the interaction of the one or more virtual characters comprises cheering, praising, celebrating, or awarding one or more of the therapeutic activities of the user.

14. The system of claim 8, wherein the one or more virtual characters are configured to interact with the user when the user gazes at the one or more virtual reality characters or when the user is idle, as determined by one or more of the processor or the wearable visual display.

15. The system of claim 8, wherein the interaction between the one or more virtual characters and the avatar comprises the one or more virtual characters acknowledging the avatar, gesturing to the avatar, approaching the avatar, or hiding from the avatar.

16. The system of claim 1, wherein at least one sensor of the one or more wearable sensors comprises an emitter, wherein the emitter and the at least one sensor are configured to track movements of the user.

17. The system of claim 16, wherein the processor further comprises instructions to display the avatar, wherein the avatar is configured to display at least a portion of the real-world movement of the user in the virtual reality environment.

18. The system of claim 17, wherein the processor includes executable instructions for an anti-gravity protocol that causes arms and hands of the avatar to float upwards as if at least a portion of the avatar was not restrained by gravity.

19. The system of claim 17, wherein a displayed virtual movement of the avatar is different from the real-world movement of the user, and a difference between the displayed virtual movement of the avatar and the real-world movement of the user is varied to induce the user to perform the therapeutic activity.

20. The system of claim 1, wherein the virtual reality environment changes in response to a measured completion or partial completion of the therapeutic activity.

21. The system of claim 20, wherein the one or more virtual characters respond to one or more of the measured completion or the partial completion of the therapeutic activity by starting a building project, wherein a completed version of the building project appears when the user logs into the virtual reality environment for a subsequent physical therapy session.

22. The system of claim 1, wherein the therapeutic activity is comprised of one or more repetitions, and wherein at least a portion of the one or more repetitions results in a display of visual cues to the user.

23. The system of claim 22, wherein the visual cues include at least one from among: a sun rises or sets, a vegetable grows, a fruit grows, a balloon moves, a bird moves, wind blows, ice melts, water flows, a building is built, or a location is modified based on virtual interaction between the user and one or more elements of the virtual reality environment.

24. The system of claim 22, wherein the visual cues include indications of whether a most recent of the one or more repetitions was executed correctly by the user, and wherein the one or more repetitions are measured for correct posture, correct balance, or both.

25. The system of claim 22, wherein:
the one or more wearable sensors are configured to determine a maximum extension achieved for each of the one or more repetitions;
the display of the visual cues is mediated by the maximum extension; and
the display of the visual cues is complete for a full extension and the display of the visual cues is partial for a partial extension.

26. The system of claim 22, wherein:
the one or more wearable sensors are configured to collect range of motion data for each of the one or more repetitions;

the display of the visual cues are mediated by a respective range of motion of the one or more repetitions;

the display of visual cues is complete for a complete repetitions; and the display of visual cues is partial for a partial repetition.

27. The system of claim 26, wherein the range of motion required for the complete repetition is adjustable by the user or a practitioner.

28. A computer implemented method for facilitating a therapeutic activity of a user, comprising:

providing a virtual reality environment comprising one or more virtual characters and an avatar that represents the user on a visual display worn by the user;

receiving data corresponding to real-world movement of the user from one or more wearable sensors worn by the user;

providing the therapeutic activity within the virtual reality environment, wherein the therapeutic activity is directed to produce a therapeutic outcome based on the real-world movement of the user;

generating exercise analytics that characterize compliance between respective real-world movement of each of a right side and a left side of the user as compared to a range of motion corresponding to the therapeutic activity, wherein the exercise analytics are generated based on data collected by the one or more wearable sensors based on the respective real-world movement of each of the right side and the left side of the user;

performing a protocol to modify display of the avatar in the virtual reality environment, wherein:

a first deviation between the range of motion and data representing the respective real-world movement of the right side of the user is compared to a second deviation between the range of motion and data representing the respective real-world movement of the left side of the user, the first deviation is determined to be less in magnitude than the second deviation, and in response to the determination, a right side of the avatar and a left side of the avatar each display respective virtual movements corresponding to the respective real world movement of the right side of the user.

29. The method of claim 28, further comprising directing the one or more virtual characters provide a user interaction, wherein:

the user interaction is in response to one or more of a measured completion or a partial completion of the therapeutic activity as characterized by the exercise analytics;

the user interaction comprises one or more of an indication to change the real-world movement of the user to conform to the therapeutic activity or an indication of successful conformity; and the user interaction is configured to promote performance of a portion of a treatment plan comprising the therapeutic activity.

30. The method of claim 29, wherein the indication comprises an indication to correct posture, balance, or both of the user in a real-world environment.

31. The method of claim 29, wherein the user interaction occurs in response to a measured completion of the therapeutic activity by the user.

32. The method of claim 29, wherein the user interaction occurs in response to a measured non-completion or partial completion of the therapeutic activity by the user.

33. The method of claim 29, wherein the user interaction comprises the one or more virtual characters mimicking or mirroring the real-world movement of the user.

34. The method of claim 29, wherein the user interaction comprises the one or more virtual characters soliciting help from the user to cause real-world movement of the user corresponding to one or more therapeutic activities.

35. The method of claim 29, wherein the user interaction of the one or more virtual characters comprises cheering, praising, celebrating, or awarding one or more of the therapeutic activities of the user.

36. The method of claim 29, wherein the indication comprises a direction for the user change to a direction or a speed of motion of the real-world movement of the user.

* * * * *